US010590181B2

(12) United States Patent
Boyden et al.

(10) Patent No.: US 10,590,181 B2
(45) Date of Patent: Mar. 17, 2020

(54) MUTANT CHANNELRHODOPSINS WITH ALTERED ION SELECTIVITY

(71) Applicant: Massachusetts Institute of Technology, Cambridge, MA (US)

(72) Inventors: Edward S. Boyden, Cambridge, MA (US); Yongku Peter Cho, Vernon, CT (US); Nathan C. Klapoetke, Ashburn, VA (US); Amy S. Chuong, Ashburn, VA (US); Fei Chen, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 14/653,040

(22) PCT Filed: Apr. 18, 2015

(86) PCT No.: PCT/US2015/026560
§ 371 (c)(1),
(2) Date: Jun. 17, 2015

(87) PCT Pub. No.: WO2015/161308
PCT Pub. Date: Oct. 22, 2015

(65) Prior Publication Data
US 2016/0176933 A1 Jun. 23, 2016

Related U.S. Application Data

(60) Provisional application No. 61/981,689, filed on Apr. 18, 2014.

(51) Int. Cl.
| | | |
|---|---|---|
| *C07K 14/705* | (2006.01) | |
| *C07K 14/405* | (2006.01) | |
| *G01N 33/50* | (2006.01) | |
| *A61K 38/00* | (2006.01) | |

(52) U.S. Cl.
CPC .......... *C07K 14/705* (2013.01); *C07K 14/405* (2013.01); *G01N 33/502* (2013.01); *G01N 33/5076* (2013.01); *A61K 38/00* (2013.01)

(58) Field of Classification Search
None
See application file for complete search history.

(56) References Cited

U.S. PATENT DOCUMENTS

2014/0324134 A1 10/2014 Klapoetke et al.

FOREIGN PATENT DOCUMENTS

| WO | 2011019081 A1 | 2/2011 |
| WO | 2012032103 A1 | 3/2012 |
| WO | 2015161308 A1 | 10/2015 |

OTHER PUBLICATIONS

Openoptogenetics (Jul. 29, 2011) Channelrhodopsins,web.archive.org/web/20110729040602/www.openoptogenetics.org:80/index.php?title=Channelrhodopsins.*
Openoptogenetics (Oct. 22, 2013) Channelrhodopsins,web.archive.org/web/20110729040602/www.openoptogenetics.org:80/index.php?title=Channelrhodopsins.*
Eisenman et al., "An Introduction to Molecular Architecture and Permeability of Ion Channels." Ann. Rev. Biophys. Chem. 1987. 16: 205-26.
Eisenman et al., "Ionic Selectivity Revisited: The Role of Kinetic and Equilibrium Processes in Ion Permeation Through Channels." J. Membrane Biol. 76, 197-225 (1983).
Gradmann et al., "Modeling Light-induced Currents in the Eye of Chlamydomonas reinhardtii." J. Membrane Biol. 189, 93-104 (2002).
Malenka et al. "Postsynaptic Calcium is Sufficient for Potentiation of Hippocampal Synaptic Transmission." Science 242 (4875), 81-84. 11.
Neher, Erwin, "Correction for Liquid Junction Potentials in Patch Clamp Experiments." Methods in Enzymolog, vol. 207, 123-131.
Orrenius et al., "Regulation of Cell Death: The Calcium-Apoptosis Link." www.nature.com/reviews/molcellbio, Jul. 2003 | vol. 4, 552-565.
Ruffert et al., "Glutamate residue 90 in the predicted transmembrane domain 2 is crucial for cation flux through channelrhodopsin 2." Biochemical and Biophysical Research Communications 410 (2011) 737-743.
Agarwal, N. et al., "Multiplex Expression Cloning of Blood-Brain Barrier Membrane Proteins", Proteomics, Feb. 2009, vol. 9, pp. 1099-1108.
Berndt, A. et al., "Two Open States with Progressive Proton Selectivities in the Branched Channelrhodopsin-2 Photocycle", Biophysical Journal, Mar. 3, 2010, vol. 98, pp. 753-761.
Bernstein, J.G. et al., "Optogenetics and thermogenetics: technologies for controlling the activity of targeted cells within intact neural circuits", Current Opinion in Neurobiology, Feb. 2012, vol. 22, pp. 61-71.
Boyden, E.S. et al., "Millisecond-timescale, genetically targeted optical control of neural activity", Nature Neuroscience, Sep. 2005, vol. 8, pp. 1263-1268.
Boyden, E.S., "A history of optogenetics: the development of tools for controlling brain circuits with light", F1000 Biology Reports, May 3, 2011, vol. 3.
Chang, D.C., "Dependence of Cellular Potential on Ionic Concentrations; Data Supporting a Modification of the Constant Field Equation", Biophysical Journal, Aug. 1983, vol. 43, pp. 149-156.
Chesler, M., "Regulation and Modulation of pH in the Brain", Physiological Review, Oct. 2003, vol. 83, pp. 1183-1221.
Chow, B.Y., et al., "High-Performance Genetically Targetable Optical Neural Silencing via Light-Driven Proton Pumps", Nature, Jan. 7, 2010, vol. 463, pp. 98-102.
Chow, B.Y., et al., "Optogenetics and Translational Medicine" Science Transl Med, 2013, vol. 5, pp. 177ps5.
Dolmetsch, R.E., et al., "Calcium oscillations increase the efficiency and specificity of gene expression", Nature, Apr. 30, 1998, vol. 392, pp. 933-936.

(Continued)

*Primary Examiner* — Michael D Pak
(74) *Attorney, Agent, or Firm* — Pierce Atwood LLP

(57) ABSTRACT

The invention, in some aspects relates to compositions and methods for altering cell activity and function and the introduction and use of mutant light-activated ion channels and variants thereof.

19 Claims, 20 Drawing Sheets

Specification includes a Sequence Listing.

(56) References Cited

OTHER PUBLICATIONS

Eisenhauer, K., et al., "In Channelrhodopsin-2 Glu-90 is Crucial for Ion Selectivity and is Deprotonated during the Photocycle", Journal of Biological Chemistry, 2012, vol. 287, pp. 6904-6911.
Ghosh, A. et al., "Calcium signaling in neurons: molecular mechanisms and cellular consequences", Science, Apr. 14, 1995, vol. 268, pp. 239-247.
Giese, K.P., et al., "Autophosphorylation at Thr286 of the alpha calcium-calmodulin kinase II in LTP and learning", Science, Feb. 6, 1998, vol. 279, pp. 870-873.
Gradmann, D., et al., "Rectification of the Channelrhodopsin Early Conductance", Biophysical Journal, Sep. 2011, vol. 101, pp. 1057-1068.
Graef, I.A., et al., "L-type calcium channels and GSK-3 regulate the activity of NF-ATc4 in hippocampal neurons", Nature, Oct. 14, 1999, vol. 401, pp. 703-708.
Hardingham, G.E., et al., "Distinct functions of nuclear and cytoplasmic calcium in the control of gene expression", Nature, Jan. 16, 1997, vol. 385, pp. 260-265.
Hayashi, Y., et al., "Driving AMPA receptors into synapses by LTP and CaMKII: requirement for GluR1 and PDZdomain interaction", Science, Mar. 24, 2000, vol. 287, pp. 2262-2267.
Hess, P., et al., "Calcium Channel Selectivity for Divalent and Monovalent Cations. Voltage and Concentration Dependence of Single Channel Current in Ventricular Heart Cells", The Journal of General Physiology, Sep. 1986, vol. 88, pp. 293-319.
Kato, H.E., et al., "Crystal structure of the channelrhodopsin light-gated cation channel", Nature, 2012, vol. 482, pp. 369-374.
Kleinlogel, S., et al., "Ultra light-sensitive and fast neuronal activation with the Ca(2)+-permeable channelrhodopsin CatCh", Nature Neuroscience, 2011, vol. 14, pp. 513-518.
Krause et al. "Structural differences between the closed and open states of channelrhodopsin-2 observed by EPR spectroscopy." FEBS Letters 587 (2013) 3309-3313.
Lin, J.Y., et al., "Characterization of Engineered Channelrhodopsin Variants with Improved Properties and Kinetics". Biophysical Journal, Mar. 2009, vol. 96, pp. 1803-1814.
Lorenz-Fonfria et al. "Channelrhodopsin unchained: Structure and mechamism of a light-gated cation channel." BBA Biochimica et Biophysica Acta 1837 (2014) 626-642.
Nagel, G., et al., "Channelrhodopsin-2, a directly light-gated cation-selective membrane channel", Proceedings of the National Academy of Science of the United States of America, Nov. 25, 2003, vol. 100, pp. 13940-13945.
Neher, E. et al., "Multiple Roles of Calcium Ions in the Regulation of Neurotransmitter Release", Neuron, Sep. 25, 2008, vol. 59, pp. 861-872.
Nikolic, K., et al., "Photocycles of channelrhodopsin-2", Photochemistry and Photobiology, Jan.-Feb. 2009, vol. 85, pp. 400-411.
Plazzo, A.P., et al., "Bioinformatic and Mutational Analysis of Channelrhodopsin-2 Protein Cation-conducting Pathway", Journal of Biological Chemistry, Feb. 10, 2012, vol. 287, pp. 4818-4125.
Prigge, M., et al., "Color-tuned channelrhodopsins for multiwavelength optogenetics", Journal of Biological Chemistry, Sep. 14, 2012, vol. 287, pp. 31804-31812.
Schneider, F., et al., "Ion selectivity and competition in channelrhodopsins", Biophysical Journal, Jul. 2, 2013, vol. 105, pp. 91-100.
"ChannelrhodopsinsCategory:Microbial Opsins", openoptogenetics, Jul. 29, 2011 Retrieved from the internet: URL: http://web.archive.org/web/20131022120835/http://www.openoptogenetics.org/index.php?title+Channelrhodopsins [retreived on May 29, 2017].
Sugiyama, Y., et al., "Photocurrent attenuation by a single polar-to-nonpolar point mutation of channelrhodopsin-2", Photochemical and Photobiological Sciences, Mar. 2009, vol. 8, pp. 328-336.
Xia, Z., et al., "Calcium influx via the NMDA receptor induces immediate early gene transcription by a MAP kinase/ERK-dependent mechanism", Journal of Neuroscience, Sep. 1, 1996, vol. 16, pp. 5425-5436.
Zhang, F., et al., "Red-shifted optogenetic excitation: a tool for fast neural control derived from Volvox carteri", Nature Neuroscience, Jun. 2008, vol. 11, pp. 631-633.
Zucker, R.S., "Calcium- and activity-dependent synaptic plasticity", Current Opinion in Neurobiology, Jun. 1999, vol. 9, pp. 305-313.
International Search Report and Written Opinion dated Sep. 18, 2015 for International Patent Application No. PCT/US2015/026560, 28 pages.
"ChannelrhodopsinsCategory:Microbial Opsins", openoptogenetics, Oct. 22, 2013, Retrieved from the internet: URL:http://web.archive.org/web/20131022120835/http://www.openoptogenetics.org/index.php?title+Channelrhodopsins [retreived on Jun. 11, 2015].
Bamann, C. et al., "Structural Guidance of the Photocycle of Channelrhodopsin-2 by an Interhelical Hydrogen Bond", Biochemistry, Jan. 19, 2010, vol. 49, pp. 267-278.
Gunaydin, L. et al., "Ultrafast Optogenetic Control", Nature Neuroscience, Jan. 17, 2010, vol. 13, pp. 387-392.
Wang, H. et al., "Moleculare Determinants Differentiating Photocurrent Properties of Tow Channelrhodopsins for Chlamydomonas", Journal of Biological Chemistry, Feb. 27, 2009, vol. 284, pp. 5685-5696.
Yizhar, O. et al., "Neocortical Excitation/Inhibition Balance in Information Processing and Social Dysfunction", Nature, Sep. 8, 2011, p. 171.
Yawo et al., "Optogenetic manipulation of neural and non-neural functions." Developmental, Growth Differentiation (2013), The Japanese Society of Developmental Biologist, pp. 1-17.

* cited by examiner

Figure 1

MDYGGALSAVGRELLFVTNPVVVNGSVLVPEDQCYCAGWIESRGTNGAQTASNVLQWLAAGFSILLLMFYAYQTWK
STCGWEEIYVCAIEMVKVILEFFFEFKNPSMLYLATGHRVQWLRYAEWLLTCPVILIHLSNLTGLSNDYSRRTMGLLVSDI
GTIVWGATSAMATGYVKVIFFCLGLCYGANTFFHAAKAYIEGYHTVPKGRCRQVVTGMAWLFFVSWGMFPILFILGPE
GFGVLSVYGSTVGHTIIDLMSKNCWGLLGHYLRVLIHEHILIHGDIRKTTKLNIGGTEIEVETLVEDEAEAGAVP

Figure 2A

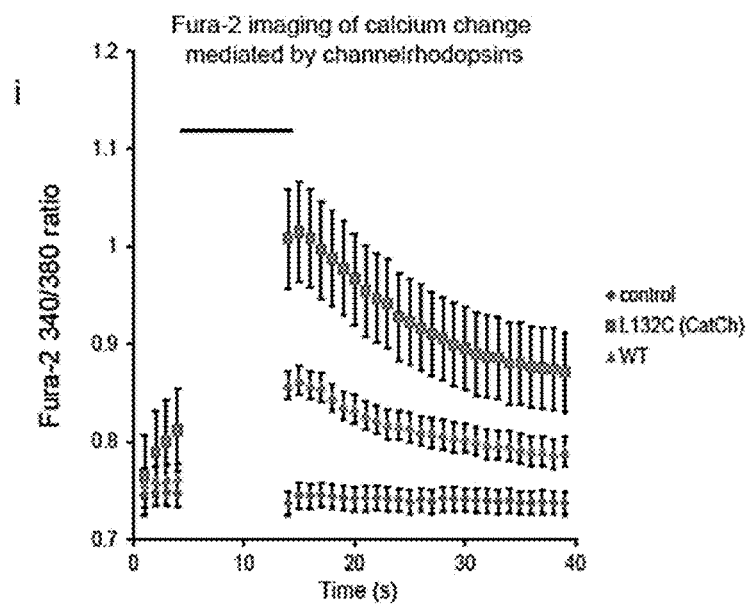

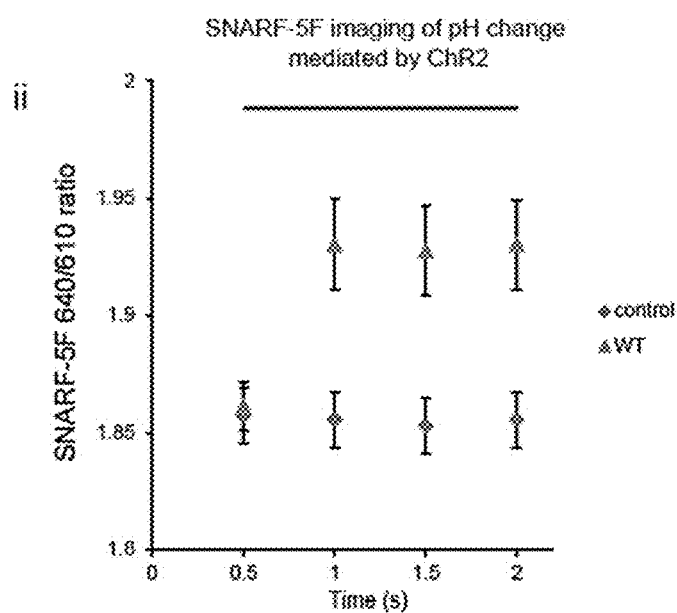

Figure 11A

```
 38   GWIESRGTNGAQTASNVLQWLAAGFSILLLMFYAYQTWKSTCGWEEIYVCAIEMVKVILE    97
 80   AWLHSRGTPGEKIGAQVCQWIAFSIAIALLTFYGFSAWKATCGWEEVYVCCVEVLFVTLE   139

98   FFFEFKNPSMLYLATGHRVQWLRYAEWLLTCPVILIHLSNLTGLSNDYSRRTMGLLVSDI   157
140   IFKEFSSPATVYLSTGNHAYCLRYFEWLLSCPVILIKLSNLSGLKNDYSKRTMGLIVSCV   199

158   GTIVWGATSAMATGYVKVIFFCLGLCYGANTFFHAAKAYIEGYHTVPKGRCRQVVTGMAW   217
200   GMIVFGMAAGLATDWLKWLLYIVSCIYGGYMYFQAAKCYVEANHSVPKGHCRMVVKLMAY   259

218   LFFVSWGMFPILFILGPEGFGVLSVYGSTVGHTIIDLMSKNCWGLLGHYLRVLIHEHILI   277
260   AYFASWGSYPILWAVGFEGLLKLSPYANSIGHSICDIIAKEFWTFLAHHLRIKIHEHILI   319

278   HGDIRKTTKLNIGG   291
320   HGDIRKTTKMEIGG   333
```

Figure 11B

```
 42   SRGTNGAQTASNVLQWLAAGFSILLLMFYAYQTWKSTCGWEEIYVCAIEMVKVILEFFFE   101
 59   NHGTELQHKIAVGLQWFTVIVAIVQLIFYGWHSFKATTGWEEVYVCVIELVKCFIELFHE   118

102   FKNPSMLYLATGHRVQWLRYAEWLLTCPVILIHLSNLTGLSNDYSRRTMGLLVSDIGTIV   161
119   VDSPATVYQTNGGAVIWLRYSMWLLTCPVILIHLSNLTGLHEEYSKRTMTILVTDIGNIV   178

162   WGATSAMATGYVKVIFFCLGLCYGANTFFHAAKAYIEGYHTVPKGRCRQVVTGMAWLFFV   221
179   WGITAAFTKGPLKILFFMIGLFYGVTCFFQIAKVYIESYHTLPKGVCRKICKIMAYVFFC   238

222   SWGMFPILFILGPEGFGVLSVYGSTVGHTIIDLMSKNCWGLLGHYLRVLIHEHILIHGDI   281
239   SWLMFPVMFIAGHEGLGLITPYTSGIGHLILDLISKNTWGFLGHHLRVKIHEHILIHGDI   298

282   RKTTKLNIGGTEIEVETLVEDEAEAG   307
299   RKTTTINVAGENMEIETFVDEEEEGG   324
```

MUTANT CHANNELRHODOPSINS WITH ALTERED ION SELECTIVITY

RELATED APPLICATIONS

This application is a National Stage Filing under U.S.C. § 371 of PCT International Application PCT/US15/26560, filed Apr. 18, 2015, which claims benefit under 35 U.S.C. § 119(e) of U.S. Provisional application Ser. No. 61/981,689 filed Apr. 18, 2014, the contents of each of which is incorporated by reference herein in its entirety.

GOVERNMENT INTEREST

This invention was made with U.S. government support under Grant Numbers 1R01NS075421 and 1R01DA029639, awarded by the National Institutes for Health, HR0011-12-C-0068, awarded by the Department of Defense, and CBET 1053233, awarded by the National Science Foundation. The government has certain rights in this invention.

FIELD OF THE INVENTION

The invention, in some aspects relates to compositions and methods for altering conductance across membranes, altering cell activity, and modulating cell function. The invention also relates to the preparation and use of light-activated ion channels polypeptides in membranes, cells, tissues, and subjects.

BACKGROUND OF THE INVENTION

Microbial opsins are naturally occurring seven-transmembrane proteins that, in response to light, translocate ions into or out of cells, and thus when heterologously expressed in genetically targeted excitable cells, enable their membrane potential to be controlled by light [Bernstein, J. G., et al. Curr Opin Neurobiol, (2011) Vol 22, No. 1, 2012, pp 61-71; Chow, B. Y. and E. S. Boyden, Sci Transl Med, 2013. 5(177): p. 177 p5; and. Boyden, E. S., F1000 Biol Rep. (2011) 3:11. Epub 2011 May 3]. As a result, such "optogenetic" tools have found widespread use in fields such as neuroscience for enabling optical activation or silencing of the electrical activity of cells [Bernstein, J. G., et al. Curr Opin Neurobiol, (2011) Vol 22, No. 1, 2012, pp 61-71], and have even been contemplated as building blocks of new kinds of optical biological control therapeutic [Chow, B. Y. and E. S. Boyden, Sci Transl Med, 2013. 5(177): p. 177 p5]. For example, the light-gated cation channel channelrhodopsin-2 (ChR2), which upon expression in neurons enable them to be electrically depolarized using light [Boyden, E. S., et al., Nat Neurosci, 2005. Vol. 8(9): p. 1263-8; Boyden, E. S., F1000 Biology Reports, 2011 3:11].

The light-activated cation channel ChR2 passes four endogenous species of positively charged ion (sodium, potassium, calcium, hydrogen) into cells, possesses defined on kinetics in response to light and off kinetics after cessation of light, passes current with an amplitude governed by its conductance, and responds to light of specific colors.

Although many users of channelrhodopsins are focusing on short-term optical activation to drive spiking activity, the calcium ions and protons that permeate the channelrhodopsin can in principle drive signaling processes within cells, ranging from kinase and phosphatase activation, to cell survival and death, to receptor trafficking, to synaptic plasticity, to gene transcription (e.g., [Neher, E. and T. Sakaba, Neuron, 2008. 59(6): p. 861-72; Ghosh, A. and M. E. Greenberg, Science, 1995. 268(5208): p. 239-47; Orrenius, S., et. al. Nat Rev Mol Cell Biol, 2003. 4(7): p. 552-65.; Chesler, M., Physiol Rev, 2003. 83(4): p. 1183-22 1.; Graef, I. A., et al., Nature, 1999. 401(6754): p. 703-8.; Hardingham, G. E., et al., Nature, 1997. 3 85(6613): p. 260-5.; Dolmetsch, R. E., et al. Nature, 1998. 392(6679): p. 933-6.; Giese, K. P., et al., Science, 1998. 279(5352): p. 870-3.; Malenka, R. C., et al., Science, 1988. 242(4875): p. 8 1-4.; Hayashi, Y., et al., Science, 2000. 287(546 1): p. 2262-7.; Zucker, R. S., Curr Opin Neurobiol, 1999. 9(3): p. 305-13.; and Xia, Z., et al., J Neurosci, 1996. 16(17): p. 5425-36.]. Thus, for many specific scientific purposes, channelrhodopsins that pass the relatively biochemically inert monovalent sodium and potassium currents might be valued, in order to focus the optical effect on depolarization of the cell.

SUMMARY OF THE INVENTION

The invention, in part, relates to mutant light-activated ion channel polypeptides and methods for their preparation and use. The invention also includes isolated nucleic acid sequences that encode mutant light-driven ion channels of the invention as well as vectors and constructs and cells that comprise such nucleic acid sequences. In addition, the invention in some aspects includes expression of mutant light-activated ion channel polypeptides in cells, tissues, and subjects as well as methods for using the mutant light-activated ion channels to alter conductance across membranes, to alter cell and tissue function, and for use in diagnosis and treatment of disorders.

According to one aspect of the invention, light-activated ion channel polypeptides are provided. The light-activated ion channel polypeptides include an amino acid sequence set forth as SEQ ID NO:1 that includes one or more amino acid modifications, or a variant thereof; wherein the one or more amino acid modifications include 1, 2, 3, 4, 5, 6, 7, or 8 A71S, I84L, I84V, E90A, E90D, E90N, E90P, E90Q, M91L, H114G, R115S, E123A, or K205A amino acid substitutions. In some embodiments, the one or more modifications additionally include one or more amino acid deletions and insertions. In some embodiments, the variant of the light-activated ion channel polypeptide amino acid sequence includes the 1, 2, 3, 4, 5, 6, 7, or 8 A71S, I84L, I84V, E90A, E90D, E90N, E90P, E90Q, M91L, H114G, R115S, E123A, or K205A amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In certain embodiments, the light-activated ion channel polypeptide has at least one of a lower level of an ion flux and a lower level of proton flux compared to a control level of the ion flux and proton flux, respectively, when expressed in a cell membrane and contacted with an ion-channel-polypeptide-activating light under suitable conditions for the ion flux and proton flux through the expressed light-activated ion channel polypeptide. In some embodiments, the control levels of ion flux and proton flux are the level of ion flux and proton flux through a light-activated ion channel polypeptide having an amino acid sequence set forth as SEQ ID NO:1 expressed in a cell membrane and contacted with the activating light under the suitable conditions for the ion flux and proton flux, respectively. In some embodiments, the ion flux includes calcium ion flux. In certain embodiments, the light-activated ion channel polypeptide does not include one or more of the A71S, I84L, I84V, E90A, E90D, E90N, E90P, E90Q, M91L, H114G, R115S, E123A, or K205A amino acid substitutions in positions corresponding to the sequence set forth as SEQ ID NO:1, and optionally does not include a substitution of one or more of the amino acids A71, I84, E90, M91, H114, R115, E123, and K205 in positions corresponding to the sequence set forth as SEQ ID NO:1. In some embodiments, the one or more amino acid modifications include A71S, E90A, and H114G. In some embodiments, the polypeptide has the amino acid sequence set forth as SEQ ID NO:11. In certain embodiments, the one or more amino acid modifications include A71S, E90A, H114G, and R115S. In some embodiments, the polypeptide has the amino acid sequence set forth as SEQ ID NO:12. In some embodiments, the light-activated ion channel polypeptide has the amino acid sequence of SEQ ID NO:1 with an A71S and an E90A substitution. In certain embodiments the light-activated ion channel polypeptide has the amino acid sequence of SEQ ID NO:1 with an E90A and an H114G substitution.

According to another aspect of the invention, a cell that includes one or more light-activated ion channel polypeptides of any of the aforementioned embodiments of light-activated ion channel polypeptides is provided. In some embodiments, the cell is an excitable cell. In some embodiments, the cell is a vertebrate cell, and optionally a mammalian cell. In certain embodiments, the cell is in vitro, ex vivo, or in vivo.

According to another aspect of the invention a nucleic acid sequence that encodes any of the aforementioned embodiments of light-activated ion channel polypeptides is provided. In certain embodiments, the nucleic acid sequence is a mammalian codon-optimized DNA sequence. In some embodiments, the light-activated ion channel encoded by the nucleic acid sequence is expressed in a cell. In aspects of the invention a composition comprising a polynucleotide having a nucleic acid sequence encoding a light activated ion channel polypeptide of the invention is provided. In some embodiments the composition further comprises a carrier.

According to another aspect of the invention vectors comprising any of the aforementioned embodiments of nucleic acids sequences are provided. In some embodiments, the nucleic acid sequence is operatively linked to a promoter sequence. In certain embodiments, the vector also includes one, two, or more nucleic acid signal sequences operatively linked to the nucleic acid sequence encoding the light-activated ion channel polypeptide. In some embodiments, the vector is a plasmid vector, cosmid vector, viral vector, or an artificial chromosome. In some embodiments, the vector also includes a nucleic acid sequence encoding one or more of a trafficking polypeptide and a fluorescent polypeptide. According to another aspect of the invention a cell that includes an embodiment of any of the aforementioned vectors is provided. According to another aspect of the invention, compositions that include any of the aforementioned embodiments of a light-activated ion channel polypeptide or variant thereof are provided. In some embodiments the composition further comprises a carrier.

According to yet another aspect of the invention, methods of changing a conductivity of a membrane are provided. The methods include (a) expressing in a host membrane a light-activated ion channel polypeptide or variant thereof of any of the aforementioned embodiments of light-activated ion channel polypeptides or variants thereof, and (b) contacting the expressed light-activated ion channel polypeptide or variant thereof with a light under suitable conditions to activate the light-activated ion channel and change the conductivity of the membrane. In certain embodiments, the host membrane is a cell membrane. In some embodiments, the cell is a human cell. In some embodiments, the conductivity of the membrane includes one or more of ion flux and proton flux across the light-activated ion channel polypeptide. In some embodiments, the host membrane is a cell membrane of a neuronal cell, a nervous system cell, a cardiac cell, a circulatory system cell, a visual system cell, or an auditory system cell.

According to another aspect of the invention, methods of identifying an effect of a candidate compound on conductivity of a membrane are provided. The methods include (a) contacting a test membrane comprising a light-activated ion channel polypeptide or variant thereof of any of the aforementioned embodiments of light-activated ion channel polypeptides or variants thereof with an ion-channel-polypeptide-activating light under conditions suitable for conductivity of the test membrane; (b) contacting the test membrane with a candidate compound; (c) detecting one or more of the presence or level of conductivity of the test membrane; and (c) identifying the presence or absence of a change in one or more of the presence and the amount of the conductivity of the test membrane contacted with the light and the candidate compound compared to the amount of one or more of the presence and level of the conductivity of a control membrane contacted with the light and not contacted with the candidate compound; wherein a change in the conductivity of the test membrane compared to the control conductivity identifies an effect of the candidate compound on the conductivity of the test membrane. In certain embodiments, the membrane is a cell membrane. In some embodiments, the change in the conductivity is a decrease in conductivity. In certain embodiments, the change in the conductivity is an increase in conductivity. In some embodiments, the conductivity of the membrane includes one or more of ion flux and proton flux across the expressed light-activated ion channel polypeptide or variant thereof.

According to another aspect of the invention, methods of treating a disease or condition in a subject are provided. The methods include (a) administering to a subject in need of such treatment, a therapeutically effective amount of a light-activated ion channel polypeptide or variant thereof of any of the aforementioned embodiments of light-activated ion channel polypeptides or variants thereof to treat the disorder; (b) expressing the light-activated ion channel polypeptide or variant thereof in a cell membrane of the subject; and (c) contacting the light-activated ion channel polypeptide or variant thereof expressed in the cell membrane with an ion-channel-polypeptide-activating light under conditions suitable for conductivity across the light-activated channel polypeptide or variant thereof, wherein the conductivity treats the disease or condition in the subject. In some embodiments, the disease or condition is injury, brain damage, spinal cord injury, epilepsy, a metabolic disorder, cardiac dysfunction, vision loss, blindness, deafness, hearing loss, or a neurological condition. In certain embodiments, the conductivity includes one or more of ion flux and proton flux across the light-activated ion channel polypeptide, or variant thereof.

According to yet another aspect of the invention, a light-activated ion channel polypeptide is provided. The light-activated ion channel polypeptide includes an amino acid sequence set forth as SEQ ID NO:1 that includes one or more amino acid modifications, or a variant thereof, wherein the one or more amino acid modifications include 1, 2, 3, 4, 5, 6, 7, 8, 9, 10, 11, 12, 13, or 14 A71S, I84L, I84V, E90A, E90D, E90N, E90P, E90Q, M91L, F98M, F102S, K103W, T112G, T112N, T112S, H114G, R115S, E123A, H134K, K205A, T250I, or T250Q amino acid substitutions. In some embodiments, the one or more modifications additionally include one or more amino acid deletions and insertions. In some embodiments, the variant of the light-activated ion channel polypeptide amino acid sequence includes the 1, 2, 3, 4, 5, 6, 7, 8, 9, 10, 11, 12, 13, or 14 A71S, I84L, I84V, E90A, E90D, E90N, E90P, E90Q, M91L, F98M, F102S, K103W, T112G, T112N, T112S, H114G, R115S, E123A, H134K, K205A, T250I, or T250Q amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In certain embodiments, the light-activated ion channel polypeptide has a changed level of at least one or more of an ion flux and a proton flux compared to a control level of the ion flux and the proton flux, respectively, when expressed in a cell membrane and contacted with an ion-channel-polypeptide-activating light under suitable conditions for the one or more ion flux and proton flux, across the expressed light-activated ion channel polypeptide. In certain embodiments, the one or more amino acid modifications include 1, 2, 3, or 4 A71S, I84L, I84V, E90A, E90D, E90N, E90P, E90Q, or E123A amino acid substitutions, and optionally also include one or more amino acid deletions and insertions. In some embodiments, the variant of the light-activated ion channel polypeptide amino acid sequence comprises the 1, 2, 3, or 4 A71S, I84L, I84V, E90A, E90D, E90N, E90P, E90Q, or E123A amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In some embodiments, the light-activated ion channel polypeptide has a lower level of ion flux compared to a control level of ion flux when expressed in a cell membrane and contacted with a light-activated ion channel polypeptide activating light under suitable conditions for ion flux across the expressed light-activated ion channel polypeptide. In some embodiments, the control level of the ion flux is the level of ion flux through a light-activated ion channel polypeptide having an amino acid sequence set forth as SEQ ID NO:1 expressed in a cell membrane and contacted with the activating light under the suitable conditions for ion flux across the light-activated ion channel polypeptide. In certain embodiments, the one or more amino acid modifications include 1, 2, 3, 4, or 5 E90A, E90N, M91L, H114G, R115S, or K205A amino acid substitutions and optionally additionally include one or more amino acid deletions and insertions. In some embodiments, the variant of the light-activated ion channel polypeptide amino acid sequence includes the 1, 2, 3, 4, or 5 E90A, E90N, M91L, H114G, R115S, or K205A amino acid substitutions of the light-activated ion channel polypeptide and has at least 80% 85%, 90%, 91%, 92%, 93%, 94%, 95%, 96%, 97%, 98%, or 99% amino acid sequence identity to the amino acid sequence of the light-activated ion channel polypeptide. In some embodiments, the light-activated ion channel polypeptide has a lower level of proton flux compared to a control level of proton flux when expressed in a cell membrane and contacted with the light-activated ion-channel-polypeptide-activating light under suitable conditions for proton flux across the expressed light-activated ion channel polypeptide. In certain embodiments, the control level of proton flux is the level of proton flux across a light-activated ion channel polypeptide having an amino acid sequence set forth as SEQ ID NO:1 expressed in a cell membrane and contacted with the activating light under the suitable conditions for proton flux across the light-activated ion channel polypeptide. In some embodiments, the one or more amino acid modifications include 1, 2, 3, or 4 K103W, T112G, T112N, T112S, H134K, or T250I amino acid substitutions and optionally additionally include one or more amino acid deletions and insertions. In some embodiments, the variant of the light-activated ion channel polypeptide amino acid sequence includes the 1, 2, 3, or 4 K103W, T112G, T112N, T112S, H134K, or T250I amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In certain embodiments, the light-activated ion channel polypeptide has a higher level of ion flux compared to a control level of the ion flux when expressed in a cell membrane and contacted with an light-activated ion channel polypeptide-activating light under suitable conditions for ion flux across the expressed light-activated ion channel polypeptide. In some embodiments, the control level of ion flux is the level of ion flux across a light-activated ion channel polypeptide having an amino acid sequence set forth as SEQ ID NO:1 expressed in a cell membrane and contacted with the activating light under the suitable conditions for ion flux across the light-activated ion channel polypeptide. In some embodiments, the one or more amino acid modifications include 1, 2, 3, 4, or 5 I84L, E90D, F98M, F102S, or T250Q amino acid substitutions and optionally additionally include one or more amino acid deletions and insertions. In certain embodiments, the variant of the light-activated ion channel polypeptide amino acid sequence includes the 1, 2, 3, 4, or 5 I84L, E90D, F98M, F102S, or T250Q amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In some embodiments, the light-activated ion channel polypeptide has a higher level of proton flux compared to a control level of proton flux when expressed in a cell membrane and contacted with an light-activated ion channel polypeptide-activating light under suitable conditions for proton flux across the expressed light-activated ion channel polypeptide. In some embodiments, the control level of proton flux is the level of proton flux across a light-activated ion channel polypeptide having an amino acid sequence set forth as SEQ ID NO:1 expressed in a cell membrane contacted with the activating light under the suitable conditions for proton flux in the light-activated ion channel polypeptide. In some embodiments, the light-activated ion channel polypeptide does not include one or more of the substitutions A71S, I84L, I84V, E90A, E90D, E90N, E90P, E90Q, M91L, F98M, F102S, K103W, T112G, T112N, T112S, H114G, R115S, E123A, H134K, K205A, T250I, and T250Q in positions corresponding to the sequence set forth as SEQ ID NO:1. In certain embodiments, the light-activated ion channel polypeptide does not include a substitution of one or more of the amino acids: A71, I84, E90, M91, F98, F102, K103, T112, H114, R115, E123, H134, K205, and T250 in positions corresponding to the sequence set forth as SEQ ID NO:1. In some embodiments, the cell is an excitable cell. In certain embodiments, the ion flux comprises calcium ion flux.

According to another aspect of the invention, compositions are provided that include any of the aforementioned embodiments of a light-activated ion channel polypeptide or variant thereof.

According to another aspect of the invention, light-activated ion channel polypeptides are provided. The light-activated ion channel polypeptides include an amino acid sequence set forth as SEQ ID NO:5 that includes one or more amino acid modifications, or a variant thereof, wherein the one or more amino acid modifications include 1, 2, 3, 4, 5, 6, 7, 8, 9, 10, 11, 12, 13, or 14 G113S, V126L, E132A, E132D, E132N, E132P, E132Q, V133L, V133L, I140M, F144S, S145W, T154G, N156G, H157S, E165A, L174C, K247A, S292I, S292Q amino acid substitutions. In some embodiments, the one or more modifications also include one or more amino acid deletions and insertions. In some embodiments, the variant of the light-activated ion channel polypeptide amino acid sequence includes the 1, 2, 3, 4, 5, 6, 7, 8, 9, 10, 11, 12, 13, or 14 G113S, V126L, E132A, E132D, E132N, E132P, E132Q, V133L, V133L, I140M, F144S, S145W, T154G, N156G, H157S, E165A, L174C, K247A, S292I, S292Q amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In certain embodiments, the light-activated ion channel polypeptide has a changed level of at least one or more of an ion flux and a proton flux compared to a control level of the ion flux and the proton flux, respectively, when expressed in a cell membrane and contacted with an ion-channel-polypeptide-activating light under suitable conditions for the one or more ion flux and proton flux, across the expressed light-activated ion channel polypeptide. In some embodiments, the light-activated ion channel polypeptide does not include one or more of the substitutions G113S, V126L, E132A, E132D, E132N, E132P, E132Q, V133L, V133L, I140M, F144S, S145W, T154G, N156G, H157S, E165A, L174C, K247A, S292I, S292Q in positions corresponding to the sequence set forth as SEQ ID NO:5. In some embodiments, the light-activated ion channel polypeptide does not include a substitution of one or more of the amino acids: G113, V126, E132, V133L, I140, F144, S145, T154, N156, H157, E165, L174, K247, and S292 in positions corresponding to the sequence set forth as SEQ ID NO:5. In certain embodiments, the cell is an excitable cell. In some embodiments, the ion flux includes calcium ion flux. According to another aspect of the invention, compositions that include any of the aforementioned embodiments of a light-activated ion channel polypeptide or variant thereof are provided.

According to yet another aspect of the invention, light-activated ion channel polypeptides are provided. The light-activated ion channel polypeptides include an amino acid sequence set forth as SEQ ID NO:8 that includes one or more amino acid modifications, or a variant thereof, wherein the one or more amino acid modifications include 1, 2, 3, 4, 5, 6, 7, 8, 9, 10, 11, 12, or 13 G88S, V101L, E107A, E107D, E107N, E107P, E107Q, L115M, V119S, D120W, N129G, A132S, M140A, L149C, H151K, K222A, L267I, L267Q amino acid substitutions. In some embodiments, the one or more modifications additionally include one or more amino acid deletions and insertions. In certain embodiments, the variant of the light-activated ion channel polypeptide amino acid sequence includes the 1, 2, 3, 4, 5, 6, 7, 8, 9, 10, 11, 12, or 13 G88S, V101L, E107A, E107D, E107N, E107P, E107Q, L115M, V119S, D120W, N129G, A132S, M140A, L149C, H151K, K222A, L267I, L267Q amino acid substitutions of the light-activated ion channel polypeptide and has at least 80%, 85%, 90%, 91%, 92%, 93%, 94%, 95%, 96%, 97%, 98%, or 99% amino acid sequence identity to the amino acid sequence of the light-activated ion channel polypeptide. In some embodiments, the light-activated ion channel polypeptide has a changed level of at least one or more of an ion flux and a proton flux compared to a control level of the ion flux and the proton flux, respectively, when expressed in a cell membrane and contacted with an ion-channel-polypeptide-activating light under suitable conditions for the one or more ion flux and proton flux, across the expressed light-activated ion channel polypeptide. In some embodiments, the light-activated ion channel polypeptide does not include one or more of the substitutions G88S, V101L, E107A, E107D, E107N, E107P, E107Q, L115M, V119S, D120W, N129G, A132S, M140A, L149C, H151K, K222A, L267I, L267Q in positions corresponding to the sequence set forth as SEQ ID NO:8. In some embodiments, the light-activated ion channel polypeptide does not include a substitution of one or more of the amino acids: G88, V101, E107, L115, V119, D120, N129, A132, M140, L149, H151, K222, L267 in positions corresponding to the sequence set forth as SEQ ID NO:8. In certain embodiments, the cell is an excitable cell. In some embodiments, the ion flux includes calcium ion flux. According to another aspect of the invention, compositions that include any of the aforementioned embodiments of a light-activated ion channel polypeptide or variant thereof or polynucleotide haven the encoding nucleic acid sequence are provided.

According to yet another aspect of the invention, methods of changing an conductivity of a membrane is provided. The methods include (a) expressing in a host membrane a light-activated ion channel polypeptide or variant thereof of any of the aforementioned embodiments of light-activated ion channel polypeptides or variants thereof, and (b) contacting the expressed light-activated ion channel polypeptide or variant thereof with a light under suitable conditions to activate the light-activated ion channel and change the conductivity of the membrane. In some embodiments, the host membrane is a cell membrane. In some embodiments, the cell is a human cell. In certain embodiments, the conductivity of a membrane comprises one or more of ion flux and proton flux across the light-activated ion channel polypeptide. In some embodiments, the host membrane is a cell membrane of a neuronal cell, a nervous system cell, a cardiac cell, a circulatory system cell, a visual system cell, or an auditory system cell. In some embodiments, the ion flux includes calcium ion flux.

According to another aspect of the invention, methods of identifying an effect of a candidate compound on conductivity of a membrane are provided. The methods include (a) contacting a test membrane that includes a light-activated ion channel polypeptide or variant thereof of any of the aforementioned embodiments of light-activated ion channel polypeptides or variants thereof with an ion-channel-polypeptide-activating light under conditions suitable for conductivity across the test membrane; (b) contacting the test membrane with a candidate compound; and (c) detecting one or more of the presence and level of conductivity of the membrane; (d) identifying the presence or absence of a change in one or more of the presence or the amount of the conductivity across the test membrane contacted with the light and the candidate compound compared to one or more of the presence and the amount of the conductivity across a control membrane contacted with the light and not contacted with the candidate compound; wherein a change in the amount of the conductivity across the test membrane compared to the control amount of conductivity identifies an effect of the candidate compound on the conductivity across the test membrane. In certain embodiments, the membrane is a cell membrane. In some embodiments, the change in the conductivity is a decrease in conductivity. In some embodiments, the change in the conductivity is an increase in conductivity. In some embodiments, the conductivity of the membrane includes one or more of ion flux and proton flux across the light-activated ion channel polypeptide or variant thereof. In certain embodiments the ion flux includes calcium ion flux.

According to another aspect of the invention, methods of treating a disease or condition in a subject are provided. The methods include (a) administering to a subject in need of such treatment, a therapeutically effective amount of a light-activated ion channel polypeptide or variant thereof of any of the aforementioned embodiments of light-activated ion channel polypeptides or variants thereof to treat the disorder; (b) expressing the light-activated ion channel polypeptide or variant thereof in a cell membrane of the subject; and (c) contacting the light-activated ion channel polypeptide or variant thereof expressed in the cell membrane with an ion-channel-polypeptide-activating light under conditions suitable for conductivity across the light-activated channel polypeptide or variant thereof, wherein the conductivity treats the disease or condition in the subject. In some embodiments, the disease or condition is injury, brain damage, spinal cord injury, epilepsy, a metabolic disorder, cardiac dysfunction, vision loss, blindness, deafness, hearing loss, or a neurological condition. In some embodiments, the conductivity includes one or more of ion flux and proton flux across the light-activated ion channel polypeptide, or variant thereof. In some embodiments, the conductivity includes calcium conductivity. According to another aspect of the invention, a cell that includes a light-activated ion channel polypeptide of any of the aforementioned embodiments of light-activated ion channel polypeptides is provided. In certain embodiments, the cell is an excitable cell. In some embodiments, the cell is a vertebrate cell, and optionally a mammalian cell. In some embodiments, the cell is in vitro, ex vivo, or in vivo.

According to another aspect of the invention a nucleic acid sequence that encodes any of the aforementioned embodiments of a light-activated ion channel polypeptide is provided. In certain embodiments, the nucleic acid sequence is a mammalian codon-optimized DNA sequence. In some embodiments, the light-activated ion channel encoded by the nucleic acid sequence is expressed in a cell. According to another aspect of the invention vectors that include any of the aforementioned embodiments of nucleic acids sequences are provided. In some embodiments, the nucleic acid sequence is operatively linked to a promoter sequence. In certain embodiments, the vector also includes one, two, or more nucleic acid signal sequences operatively linked to the nucleic acid sequence encoding the light-activated ion channel polypeptide. In some embodiments, the vector is a plasmid vector, cosmid vector, viral vector, or an artificial chromosome. In certain embodiments, the vector also includes a nucleic acid sequence encoding one or more of a trafficking polypeptide and a fluorescent polypeptide. According to another aspect of the invention a cell that includes an embodiment of any of the aforementioned vectors is provided. According to another aspect of the invention, compositions that include any of the aforementioned embodiments of a light-activated ion channel polypeptide or variant thereof or a polynucleotide having an encoding nucleic acid sequence are provided, and optionally include a carrier.

BRIEF DESCRIPTION OF THE DRAWINGS

Other aspects, advantages and novel features of the invention will become more apparent from the following detailed description of the invention when considered in conjunction with the accompanying drawings wherein:

FIG. 1 is the amino acid sequence of wild-type ChR2 (SEQ ID NO:1).

FIGS. 2A-E graphically depict results of physiological screening for calcium and proton selectivity. FIG. 2A is a graph showing the change in Fura-2 340/380 nm emission ratio (i) and SNARF-5F 640/610 nm emission ratio (ii) mediated by previously described channelrhodopsins. Cells expressing fluorophores only were used as controls [mCherry in FIG. 2A(i) and EGFP in FIG. 2A(ii)] (n=20-35 cells each). Black bar, illumination period, 470 nm, 10 s, irradiance 4.6 mW/mm$^2$ (i), 500 nm, 1.5 s, irradiance 4 mW/mm$^2$ (ii). FIGS. 2B and 2C are histograms showing outcome of the calcium and proton selectivity of the screen for channelrhodopsins. FIG. 2Bi shows the Fura-2 340/380 ratio and FIG. 2Ci shows calcium concentration after blue light illumination (delivered as in FIG. 2A) in HEK cells expressing indicated ChR2 mutants (n=12-69 cells), and FIG. 2Bii shows the SNARF-5F 640/610 ratio and FIG. 2Cii shows pH after green light illumination (delivered as in FIG. 2A, but with is pulses) in HEK cells that were expressing the indicated ChR2 mutants (n=8-35 cells). FIGS. 2D and 2E are graphs showing population data for photocurrent density ratios, measured using whole-cell patch clamp in HEK cells in ion-specific extracellular solutions, for calcium photocurrent (I_calcium) measured in 90 mM CaCl$_2$, pH 7.4 divided by sodium photocurrent (I_sodium) measured in 145 mM NaCl, pH 7.4 (FIG. 2D), and proton photocurrent (I_proton) measured in 135 mM NMDG, pH 6.4 divided by sodium photocurrent (I_sodium) (FIG. 2E), of wild-type ChR2 and mutants with improved ion selectivity identified from FIGS. 2B and 2C, using illumination conditions 470 nm, 1 s, 10 mW/mm$^2$ (n=5-10 HEK293FT cells each). In FIGS. 2D and 2E, peak and steady-state photocurrent ratios for wild-type ChR2 are indicated by dashed lines and dotted lines, respectively. Statistics for the panels of FIG. 2Bi-ii and FIGS. 2D and 2E: *, P<0.05; , P<0.01, *, P<0.001, non-Bonferroni corrected t-test comparing mutant vs. wild-type.

FIG. 3A depicts population data for proton-to-sodium photocurrent ratio vs. calcium-to-sodium photocurrent ratio of ChR2 mutants, measured using whole-cell patch clamp in HEK cells in ion-selective extracellular solutions (see Examples for details), using 470 nm, 1 s illumination, 10 mW/mm$^2$ irradiance (n=6-12 HEK293FT cells each). FIGS. 3B and 3C show population data for photocurrent density ratios measured using whole-cell patch clamp, for peak (filled bars) and steady-state (open bars) calcium photocurrent (I_calcium) divided by sodium photocurrent (I_sodium) (FIG. 3B), and peak (filled bars) and steady-state (open bars) proton photocurrent (I_proton) divided by sodium photocurrent (I_sodium) (FIG. 3C), of wild-type ChR2 and triple mutant A71S/E90A/H114G (n=7-10 HEK293FT cells each), aka Chrome, measured using the same illumination as in FIG. 3A. FIG. 3D provides representative traces of photocurrent density, measured using whole-cell voltage clamp for the mutants in FIG. 3A, using the same illumination conditions. FIGS. 3E-H provide population data for peak photocurrent density (FIG. 3E), steady-state photocurrent density (FIG. 3F), steady-state to peak photocurrent ratio (FIG. 3G) (measured using 470 nm, 1 s illumination, 10 mW/mm$^2$ irradiance), and channel closing rate $e$ (T$_{off}$) (FIG. 3H) (measured using 470 nm, 2 ms illumination, 10 mW/mm$^2$ irradiance), of mutants and mutant combinations in FIG. 3A (n=4-11 HEK293FT cells each). Statistics for the panels of FIGS. 3B-C and FIGS. 3E-H: *, P<0.05; , P<0.01, *, P<0.001, non-Bonferroni corrected t-test comparing mutant vs. wild-type.

FIGS. 4A-C show population data for reversal potentials, measured using whole-cell patch clamp in HEK cells in ion-specific extracellular solutions (see Examples for method details), with peak (filled bars) and steady-state (open bars) reversal potentials, for wild-type ChR2 and the 10 ion selectivity mutants shown in FIGS. 2D-E (n=3-6 HEK293FT cells each), for: sodium (E_rev_sodium) measured in 145 mM NaCl, pH 7.4 (FIG. 4A), calcium (E_rev_calcium) measured in 90 mM $CaCl_2$, pH 7.4 (FIG. 4B), and proton (E_rev_proton) measured in 135 mN NMDG, pH 6.4 (FIG. 4C). FIGS. 4D-E provide population data for peak (filled bars) and steady-state (open bars) reversal potentials, relative to sodium reversal (n=3-6 HEK293FT cells each), for: calcium (E_rev_calcium–E_rev_sodium) (FIG. 4D), and proton (E_rev_proton–E_rev_sodium) (FIG. 4E). Illumination conditions: 470 nm, 1 s, 10 mW/mm$^2$ in all panels. Indicated are peak (dashed lines) and steady-state (dotted lines) reversal potentials for wild-type ChR2. Statistics for all panels: *, P<0.05; , P<0.01, *, P<0.001, non-Bonferroni corrected t-test comparing mutant vs. wild-type.

FIGS. 5A and 5B show I_proton/I_sodium vs. I_calcium/I_sodium for both peak (FIG. 5A) and steady-state (FIG. 5B) photocurrents, for wild-type ChR2 and 10 mutants with improved ion selectivity shown in FIG. 2D, e (n=5-12 HEK293FT cells each). (FIGS. 5C, 5D) E_rev_proton–E_rev_sodium vs. E_rev_calcium–E_rev_sodium, for both peak (FIG. 5C) and steady-state (FIG. 5D) photocurrents, for wild-type ChR2 and the 10 mutants in FIGS. 5A and 5B. Lines are linear regression fits.

FIGS. 6A-C show population data for peak (filled bars) and steady-state (open bars) photocurrent densities, measured using whole-cell patch clamp in HEK cells in ion-specific extracellular solutions, for wild-type ChR2 and 10 mutants with improved ion selectivity shown in FIGS. 2D, 2E (n=5-12 HEK293FT cells each), for: sodium (I_sodium) measured in 145 mM NaCl, pH 7.4 (FIG. 6A), calcium (I_calcium) measured in 90 mM $CaCl_2$, pH 7.4 (FIG. 6B), and proton (I_proton) measured in 135 mM NMDG, pH 6.4 (FIG. 6C). Illumination conditions: 470 nm, 1 s, 10 mW/mm$^2$ in all panels. Indicated are peak (dashed lines) and steady-state (dotted lines) photocurrent densities for wild-type ChR2. Statistics for all panels: *, P<0.05; , P<0.01, *, P<0.001, non-Bonferroni corrected t-test comparing mutant vs. wild-type.

FIGS. 7A-C provide population data for peak (filled bars) and steady-state (open bars) photocurrent densities, measured using whole-cell patch clamp in HEK cells in ion-specific extracellular solutions, for wild-type ChR2 and mutant combinations shown in FIG. 3A (n=4-12 HEK293FT cells each), for: sodium (I_sodium) measured in 145 mM NaCl, pH 7.4 (FIG. 7A), calcium (I_calcium) measured in 90 mM $CaCl_2$, pH 7.4 (FIG. 7B), and proton (I_proton) measured in 135 mM NMDG, pH 6.4 (FIG. 7C). FIGS. 7D-E provide population data for peak (filled bars) and steady-state (open bars) photocurrent density ratios, measured using whole-cell patch clamp in HEK cells in ion-specific extracellular solutions, for wild-type ChR2 and mutant combinations shown in FIGS. 7A-C (n=4-12 HEK293FT cells each), for: calcium photocurrent (I_calcium) divided by sodium photocurrent (I_sodium) (FIG. 7D), and proton photocurrent (I_proton) divided by sodium photocurrent (I_sodium) (FIG. 7E). Illumination conditions: 470 nm, 1 s, 10 mW/mm$^2$ in all panels. Indicated are peak (dashed lines) and steady-state (dotted lines) photocurrent densities (FIGS. 7A-C) and photocurrent ratios (FIGS. 7D, 7E) for wild-type ChR2. Statistics for all panels: *, P<0.05; , P<0.01, *, P<0.001, non-Bonferroni corrected t-test comparing mutant vs. wild-type.

FIGS. 8A-C provide population data for peak (filled bars) and steady-state (open bars) reversal potentials, measured using whole-cell patch clamp in HEK cells in ion-specific extracellular solutions (see Examples for method details), for wild-type ChR2 and mutant combinations shown in FIG. 3A (n=4-8 HEK293FT cells each), for: sodium (E_rev_sodium) measured in 145 mM NaCl, pH 7.4 (FIG. 8A), calcium (E_rev_calcium) measured in 90 mM CaCl2, pH 7.4 (FIG. 8B), and proton (E_rev_proton) measured in 135 mM NMDG, pH 6.4 (FIG. 8C). FIGS. 8D and 8E provide population data for peak (filled bars) and steady-state (open bars) reversal potentials, relative to sodium reversal, for ChR2 mutant combinations shown in FIGS. 8A-C (n=4-8 HEK293FT cells each), for: calcium (E_rev_calcium–E_rev_sodium) (FIG. 8D), and proton (E_rev_proton–E_rev_sodium) (FIG. 8E). Illumination conditions: 470 nm, 1 s, 10 mW/mm$^2$ in all panels. Indicated are peak (dashed lines) and steady-state (dotted lines) reversal potentials for wild-type ChR2. Statistics for all panels: *, P<0.05; , P<0.01, *, P<0.001, non-Bonferroni corrected t-test comparing mutant vs. wild-type.

FIGS. 9A and 9B provide estimated permeability ratios, calculated using a modified Goldman-Hodgkin-Katz equation, between calcium and -sodium (P*_calcium/P*_sodium) (FIG. 9A), and between protons and sodium (P*_proton/P*_sodium) (FIG. 9B), for ChR2, and mutants thereof.

FIG. 10A provides population data for peak (filled bars) and steady-state (open bars) photocurrent density measured in Tyrode's solution divided by the total fluorescence of each cell, of wild-type ChR2 and Chrome using 470 nm, is illumination, 10 mW/mm$^2$ irradiance (n=6-10 HEK293FT cells each). FIGS. 10B-C provide population data for peak (filled bars) and steady-state (open bars) potassium photocurrent properties measured using illumination conditions as in (a), including density measured in 145 mM KCl, pH 7.4 (FIG. 10B), as well as peak (filled bars) and steady-state (open bars) potassium photocurrent (I_potassium) divided by sodium photocurrent (I_sodium) (FIG. 10C), of wild-type ChR2 and Chrome (n=6 HEK293FT cells each). Statistics for all panels: *, P<0.05; , P<0.01, *, P<0.001, non-Bonferroni corrected t-test comparing mutant vs. wild-type.

FIGS. 11A-B are sequence alignments of ChR2 amino acid sequences with sequences from Chrimson and Chronos. FIG. 11A shows alignment of ChR2 polypeptide (SEQ ID NO:4) (top sequence, which includes amino acids 38-291 of SEQ ID NO:1) with Chrimson polypeptide (SEQ ID NO:7) (lower sequence, which includes amino acids 80-333 of SEQ ID NO:5). FIG. 11B shows alignment of ChR2 polypeptide (SEQ ID NO:4) (top sequence, which includes amino acids 42-307 of SEQ ID NO:1) with Chronos polypeptide (SEQ ID NO:10) (lower sequence, which includes amino acids 59-324 of SEQ ID NO:8).

BRIEF DESCRIPTION OF THE SEQUENCES

Figure 2B:
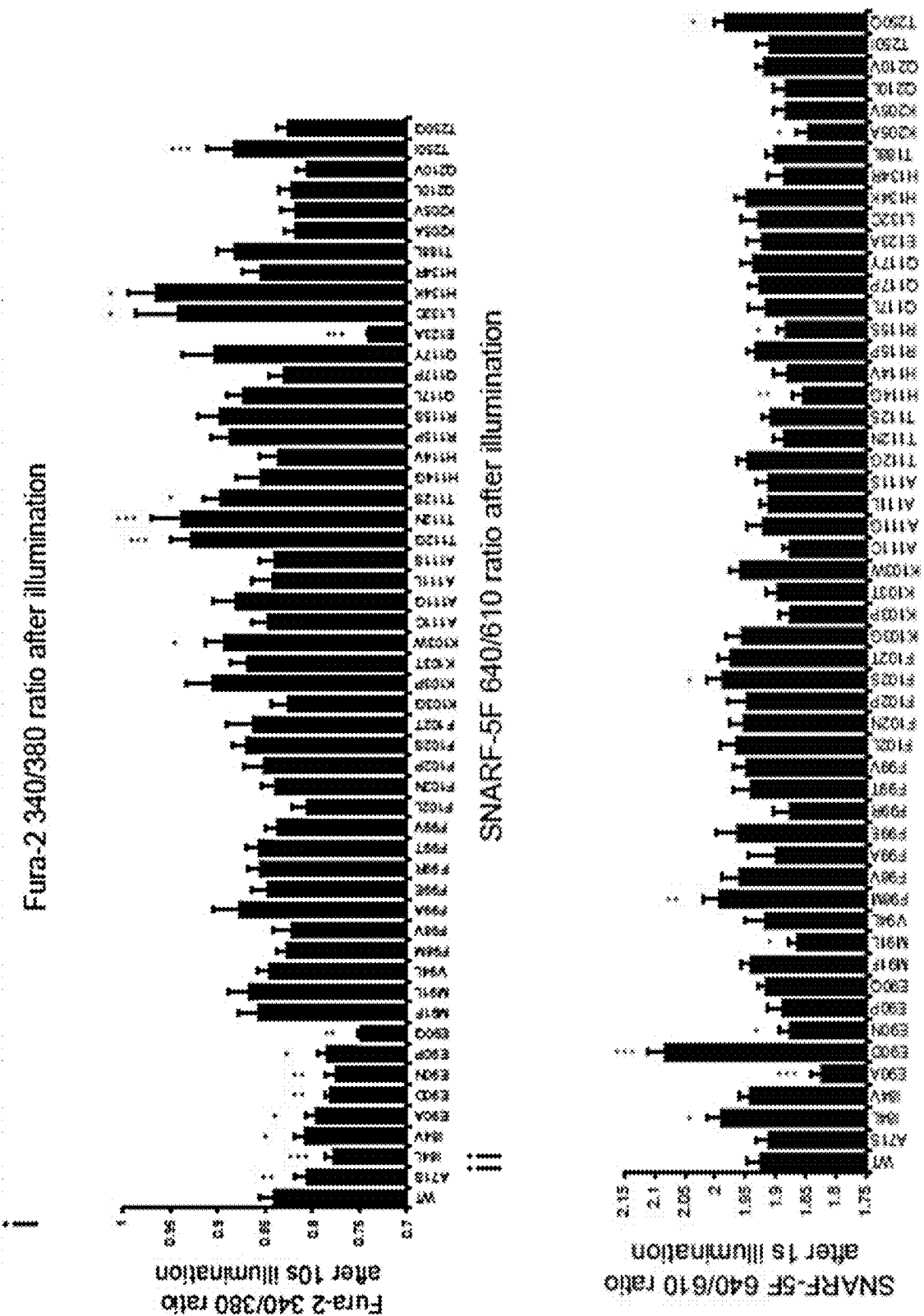

SEQ ID NO:1 ChR2 polypeptide amino acid sequence

MDYGGALSAVGRELLFVTNPVVVNGSVLVPEDQCYCAGWIESRGTNGAQT

ASNVLQWLAAGFSILLLMFYAYQTWKSTCGWEEIYVCAIEMVKVILEFFF

EFKNPSMLYLATGHRVQWLRYAEWLLTCPVILIHLSNLTGLSNDYSRRTM

GLLVSDIGTIVWGATSAMATGYVKVIFFCLGLCYGANTFFHAAKAYIEGY

HTVPKGRCRQVVTGMAWLFFVSWGMFPILFILGPEGFGVLSVYGSTVGHT

IIDLMSKNCWGLLGHYLRVLIHEHILIHGDIRKTTKLNIGGTEIEVETLV

EDEAEAGAVP.

SEQ ID NO:2 is the mammalian codon-optimized DNA sequence that encodes the wild-type Channelrhodopsin-2 (ChR2), (Boyden, E. et al., *Nature Neuroscience* 8, 1263-1268 (2005) and Nagel, G., et al. *PNAS* Nov. 25, 2003 vol. 100 no. 24 13940-13945)

atggactatggcggcgctttgtctgccgtcggacgcgaacttttgttcg ttactaatcctgtggtggtgaacgggtccgtcctggtccctgaggatca atgttactgtgccggatggattgaatctcgcggcacgaacggcgctcag accgcgtcaaatgtcctgcagtggcttgcagcaggattcagcatttttgc tgctgatgttctatgcctaccaaacctggaaatctacatgcggctggga ggagatctatgtgtgcgccattgaaatggttaaggtgattctcgagttc tttttttgagtttaagaatccctctatgctctaccttgccacaggacacc gggtgcagtggctgcgctatgcagagtggctgctcacttgtcctgtcat ccttatccacctgagcaacctcaccggcctgagcaacgactacagcagg agaaccatgggactccttgtctcagacatcgggactatcgtgtgggggg ctaccagcgccatggcaaccggctatgttaaagtcatcttcttttgtct tggattgtgctatggcgcgaacacatttttttcacgccgccaaagcatat atcgagggttatcatactgtgccaaagggtcggtgccgccaggtcgtga ccggcatggcatggctgttttttcgtgagctggggtatgttcccaattct cttcatttttggggcccgaaggttttggcgtcctgagcgtctatggctcc accgtaggtcacacgattattgatctgatgagtaaaaattgttggggggt tgttgggacactacctgcgcgtcctgatccacgagcacatattgattca cggagatatccgcaaaaccaccaaactgaacatcggcggaacggagatc gaggtcgagactctcgtcgaagacgaagccgaggccggagccgtg.

SEQ ID NO:3 includes amino acids 39-291 of SEQ ID NO:1

GWIESRGTNGAQTASNVLQWLAAGFSILLLMFYAYQTWKSTCGWEEIYV

CAIEMVKVILEFFFEFKNPSMLYLATGHRVQWLRYAEWLLTCPVILIHLS

NLTGLSNDYSRRTMGLLVSDIGTIVWFATSAMATGYVKVIFFCLGLCYG

ANTFFHAAKAYIEGYHTVPKGRCRQVVTGMAWLFFVSWGMFPILFILGP

EGFGVLSVYGSTVGHTIIDLMSKNCWGLLGHYLRVLIHEHILIHGDIRK

TTKLNIGG.

SEQ ID NO:4 includes amino acids 42-307 of SEQ ID NO:1

SRGTNGAQTASNVLQWLAAGFSILLLMFYAYQTWKSTCGWEEIYVCAIE

MVKVILEFFFEFKNPSMLYLATGHRVQWLRYAEWLLTCPVILIHLSNLT

GLSNDYSRRTMGLLVSDIGTIVWGATSAMATGYVKVIFFCLGLCYGANT

FFHAAKAYIEGYHTVPKGRCRQVVTGMAWLFFVSWGMFPILFILGPEGF

GVLSVYGSTVGHTIIDLMSKNCWGLLGHYLRVLIHEHILIHGDIRKTTK

LNIGGTEIEVETLYVEDEAEAG.

SEQ ID NO:5 is amino acid sequence of Chrimson polypeptide (ChR88)

MAELISSATRSLFAAGGINPWPNPYHHEDMGCGGMTPTGECFSTEWWCD

PSYGLSDAGYGYCFVEATGGYLVVGVEKKQAWLHSRGTPGEKIGAQVCQ

WIAFSIAIALLTFYGFSAWKATCGWEEVYVCCVEVLFVTLEIFKEFSSP

ATVYLSTGNHAYCLRYFEWLLSCPVILIKLSNLSGLKNDYSKRTMGLIV

SCVGMIVFGMAAGLATDWLKWLLYIVSCIYGGYMYFQAAKCYVEANHSV

PKGHCRMVVKLMAYAYFASWGSYPILWAVGPEGLLKLSPYANSIGHSIC

DIIAKEFWTFLAHHLRIKIHEHILIHGDIRKTTKMEIGGEEVEVEEFVE

EEDEDTV.

SEQ ID NO:6 is a mammalian-codon optimized DNA sequence encoding ChR88 light-activated ion channel polypeptide atggctgagctgatcagcagcgccaccagatctctgtttgccgccggag gcatcaaccctggcctaaccctaccaccacgaggacatgggctgtgg aggaatgacacctacaggcgagtgcttcagcaccgagtggtggtgtgac ccttcttacggactgagcgacgccggatacggatattgcttcgtggagg ccacaggcggctacctggtcgtgggagtggagaagaagcaggcttggct gcacagcagaggcacaccaggagaaaagatcggcgcccaggtctgccag tggattgctttcagcatcgccatcgccctgctgacattctacggcttca gcgcctggaaggccacttgcggttgggaggaggtctacgtctgttgcgt cgaggtgctgttcgtgaccctggagatcttcaaggagttcagcagcccc gccacagtgtacctgtctaccggcaaccacgcctattgcctgcgctact tcgagtggctgctgtcttgccccgtgatcctgatcaagctgagcaacct -continued

```
gagcggcctgaagaacgactacagcaagcggaccatgggcctgatcgtg
tcttgcgtgggaatgatcgtgttcggcatggccgcaggactggctaccg
attggctcaagtggctgctgtatatcgtgtcttgcatctacggcggcta
catgtacttccaggccgccaagtgctacgtggaagccaaccacagcgtg
cctaaaggccattgccgcatggtcgtgaagctgatggcctacgcttact
tcgcctcttggggcagctaccccaatcctctgggcagtgggaccagaagg
actgctgaagctgagcccttacgccaacagcatcggccacagcatctgc
gacatcatcgccaaggagttttggaccttcctggcccaccacctgagga
tcaagatccacgagcacatcctgatccacggcgacatccggaagaccac
caagatggagatcgaggcgaggaggtggaagtggaagagttcgtggag
gaggaggacgaggacacagtg
```

SEQ ID NO:7 a Chrimson polypeptide sequence that includes amino acids 80-333 of SEQ ID NO:5

```
AWLHSRCGTPGEKIGAQVCQWIAFSIAIALLTFYGFSAWKATCGWEEVYV
CCVEVLFVTLEIFKEFSSPATVYLSTGNHAYCLRYFEWLLSCPVILIKLS
NLSGLKNDYSKRTMGLIVSCVGMIVFGMAAGLATDWLKWILLYIVSCIYG
GYMYFQAAKCYVEANHSVPKGHCRMVVKLMAYAYFASWGSYPILWAVGPE
GLLKLSPYANSIGHSICDIIAKEFWTFLAHHLRIKIHEHILIHGDIRKTT
KMEIGG.
```

SEQ ID NO:8 is a Chronos (ChR90) coding amino acid sequence

```
METAATMTHAFISAVPSAEATIRGLLSAAAVVTPAADAHGETSNATTAG
ADHGCFPHINHGTELQHKIAVGLQWFTVIVAIVQLIFYGWHSFKATTGW
EEVYVCVIELVKCFIELFHEVDSPATVYQTNGGAVIWLRYSMWLLTCPV
ILIHLSNLTGLHEEYSKRTMTILVTDIGNIVWGITAAFTKGPLKILFFM
IGLFYGVTCFFQIAKVYIESYHTLPKGVCRKICKIMAYVFFCSWLMFPV
MFIAGHEGLGLITPYTSGIGHLILDLISKNTWGFLGHHLRVKIHEHILI
HGDIRKTTTINVAGENMEIETFVDEEEGGV.
```

SEQ ID NO:9 is a mammalian-codon optimized DNA sequence encoding ChR90

```
atggaaacagccgccacaatgacccacgcctttatctcagccgtgccta
gcgccgaagccacaattagaggcctgctgagcgccgcagcagtggtgac
accagcagcagacgctcacggagaaacctctaacgccacaacagccgga
gccgatcacggttgcttccccacatcaaccacggaaccgagctgcagc
acaagatcgcagtgggactccagtggttcaccgtgatcgtggctatcgt
gcagctcatcttctacggttggcacagcttcaaggccacaaccggctgg
gaggaggtctacgtctgcgtgatcgagctcgtcaagtgcttcatcgagc
tgttccacgaggtcgacagcccagccacagtgtaccagaccaacggagg
agccgtgatttggctgcggtacagcatgtggctcctgacttgccccgtg
atcctgatccacctgagcaacctgaccggactgcacgaagagtacagca
```
```
agcggaccatgaccatcctggtgaccgacatcggcaacatcgtgtgggg
gatcacagccgcctttacaaagggccccctgaagatcctgttcttcatg
atcggcctgttctacggcgtgacttgcttcttccagatcgccaaggtgt
atatcgagagctaccacaccctgcccaaaggcgtctgccggaagatttg
caagatcatggcctacgtcttcttctgctcttggctgatgttccccgtg
atgttcatcgccggacacgagggactgggcctgatcacaccttacacca
gcggaatcggccacctgatcctggatctgatcagcaagaacacttgggg
cttcctgggccaccacctgagagtgaagatccacgagcacatcctgatc
cacggcgacatccggaagacaaccaccatcaacgtggccggcgagaaca
tggagatcgagaccttcgtcgacgaggaggaggagggaggagtg.
```

SEQ ID NO:10 is a Chronos polypeptide sequence that includes amino acids 59-324 of SEQ ID NO:8

```
NHGTELQHKIAVGLQWFTVIVAIVQLIFYGWHSFKATTGWEEVYVCVIE
LVKCFIELFHEVDSPATVYQTNGGAVIWLRYSMWLLTCPVILIHLSNLT
GLHEEYSKRTMTILVTDIGNIVWGITAAFTKGPLKILFFMIGLFYGVTC
FFQIAKVYIESYHTLPKGVCRKICKIMAYVFFCSWLMFPVMFIAGHEGL
GLITPYTSGIGHLILDLISKNTWGFLGHHLRVKIHEHILIHGDIRKTTT
INVAGENMEIETFVDEEEEGG.
```

SEQ ID NO:11 is amino acid sequence of Chrome polypeptide

```
MDYGGALSAVGRELLFVTNPVVVNGSVLVPEDQCYCAGWIESRGTNGAQT
ASNVLQWLAAGFSILLLMFYSYQTWKSTCGWEEIYVCAIAMVKVILEFFF
EFKNPSMLYLATGGRVQWLRYAEWLLTCPVILIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDEAEAGAVP.
```

SEQ ID NO:12 is amino acid sequence of ChromeQ polypeptide

```
MDYGGALSAVGRELLFVTNPVVVNGSVLVPEDQCYCAGWIESRGTNGAQT
ASNVLQWLAAGFSILLLMFYSYQTWKSTCGWEEIYVCAIAMVKVILEFFF
EFKNPSMLYLATGGSVQWLRYAEWLLTCPVILIHLSNLTGLSNDYSRRTM
GLLVSDIGTIVWGATSAMATGYVKVIFFCLGLCYGANTFFHAAKAYIEGY
HTVPKGRCRQVVTGMAWLFFVSWGMFPILFILGPEGFGVLSVYGSTVGHT
IIDLMSKNCWGLLGHYLRVLIHEHILIHGDIRKTTKLNIGGTEIEVETLV
EDEAEAGAVP.
```

DETAILED DESCRIPTION

ChR2 mutants have now been identified, prepared, expressed, and tested that have order-of-magnitude reductions in calcium and proton photocurrent, without sacrificing sodium and potassium photocurrent, or kinetics. Two of the new molecules identified are named Chrome (for CHannel-Rhodopsin that OMits cErtain ions), which is set forth herein as SEQ ID NO:11 and ChromeQ (for Chrome with Quadruple mutations), which is set forth herein as SEQ ID NO:12, are triple and quadruple mutants respectively of ChR2 that were identified through several systematic screening steps. Additional mutant light-activated ion channel polypeptides have also been identified, including, but not limited to a mutant light-activated ion channel polypeptide having the amino acid sequence of SEQ ID NO:1 with an A71S and an E90A substitution; a mutant light-activated ion channel polypeptide having the amino acid sequence of SEQ ID NO:1 with an E90A and an H114G substitution; and mutants of Chrimson and Chronos light-activated ion channel polypeptides and variants thereof that include one or more amino acid substitutions described herein.

The invention, in part, also relates to methods for adjusting the voltage potential of cells, subcellular regions, or extracellular regions. Some aspects of the invention include methods of incorporating one or more mutant light-activated ion channel or variant thereof of the invention into at least one target cell, subcellular region, or extracellular region, the ion channel functioning to change transmembrane passage of ions in response to a specific wavelength of light. Exposing an excitable cell that includes an expressed light-driven ion channel of the invention to a wavelength of light that activates the channel, may result in depolarization of the excitable cell.

In some embodiments, the invention comprises a method for the expression of newly identified sequences that encode a mutant light-activated ion channel or variant thereof of the invention, in genetically targeted cells, to allow millisecond-timescale generation of current in response to pulses of light. The mutant light-activated channels of the invention can be genetically expressed in specific cells (e.g., using a virus or other means for delivery) and then used to control cells in intact organisms (including humans) as well as cells in vitro, in response to contact with pulses of light.

The ability to optically perturb, modify, or control cellular function offers many advantages over physical manipulation mechanisms, such as speed, non-invasiveness, and the ability to easily span vast spatial scales from the nanoscale to macroscale. One such approach is an opto-genetic approach, in which mutant light-activated ion channels of the invention, including but not limited to mutant ChR2, Chrimson, and Chronos light-activated ion channels or variants thereof of the invention, are used to alter the movement of ions and protons across cell membranes in which one or more mutant light-activated ion channel polypeptides of the invention is expressed.

Using screening steps as described herein, it was found that about 15% of the amino acid positions of ChR2 (SEQ ID NO:1), [amino acid sequence shown in FIG. 1, identified mutations listed in Table 1] could be mutated to increase the magnitude of light-driven responses, validating homology- and structure-based predicted amino acid positions (see for example Sugiyama, Y., et al., Photochem Photobiol Sci, 2009. 8(3):328-36; Ruffert, K., et al., Biochem Biophys Res Commun, 2011. 410(4):737-43; Kato, H. E., et al., Nature, 2012. 482(7385):369-74), but also revealing many novel regions of the protein, scattered throughout its backbone, that contribute to photocurrent amplitude. One quarter of the mutations that increased light-driven responses also decreased light-driven calcium or proton fluxes. Some of these mutants had additive properties, in the sense that combining multiple mutants that each make ion conductance more selective resulted in a cumulatively even more ion selective opsin.

Table 1 lists amino acid positions and mutations identified from the screen. In order to prioritize residues to screen, amino acid positions were selected from the residue map stage with the highest improvement (A88, E90, M91, F98, F99, F102, K103, T112, H114, R115, Q117, H134, N187, T188, T202, K205, G206, Q210, T250; normalized mean>1.5) as well as those that were near the 1.5-fold changed residues (A71, I84, V94, F100, A111, E123, L132) to screen for target mutations. '-' indicates that the amino acid position has not been selected according to this criteria. 'Not found' indicates amino acid positions that have been screened but mutations with statistically significant improvement have not been identified

TABLE 1

Amino acid positions and mutations identified from the screen using ChR2

| Amino acid positions identified from residue map stage | Wild-type sequence | Target mutation stage | Target checking stage |
| --- | --- | --- | --- |
| 3 | Y | — | — |
| 18 | T | — | — |
| 19 | N | — | — |
| 47 | G | — | — |
| 60 | A | — | — |
| 62 | F | — | — |
| 71 | A | S | S |
| 74 | T | — | — |
| 75 | W | — | — |
| 77 | S | — | — |
| 84 | I | L V | L V |
| 88 | A | L S T V | not found |
| 90 | E | A D F N P Q T | A D N P Q |
| 91 | M | F I L S T | F L |
| 93 | K | — | — |
| 94 | V | L T | L |
| 95 | I | — | — |
| 98 | F | A M R V | M V |
| 99 | F | A E M R T V | A E R T V |
| 100 | F | not found | — |
| 102 | F | G L N P S T | L N P S T |
| 103 | K | A G H I P R T W | G P T W |
| 111 | A | C G H L S | C G L S |
| 112 | T | D G N P R S W | G N S |
| 114 | H | A G V | G V |
| 115 | R | P S | P S |
| 117 | Q | L P Y | L P Y |
| 123 | E | A | A |
| 132 | L | A C G | C |
| 133 | I | C L P | not found |
| 134 | H | K R | K R |
| 136 | S | — | — |
| 151 | G | — | — |
| 173 | V | — | — |
| 181 | G | — | — |
| 185 | G | — | — |
| 187 | N | not found | — |
| 188 | T | L V | L |
| 202 | T | A L R S | not found |
| 205 | K | A E P Q R S T V | A V |
| 206 | G | not found | — |
| 210 | Q | L V | L V |
| 214 | G | — | — |
| 246 | T | — | — |
| 250 | T | I Q | I Q |
| 251 | I | — | — |
| 269 | V | — | — |
| 272 | H | — | — |
| 273 | E | — | — |

The invention in some aspects relates to novel mutant light-activated ion channel polypeptides and nucleic acid sequences that encode the polypeptides. Mutant light-activated ion channel polypeptides, and variants thereof of the invention can be expressed in cell membranes and can be activated by contact with one or more pulses of light, which results in ion and proton flux across the channel and thus, across the membrane in which the mutant light-activated ion channels of the invention are expressed.

Light-activated ion channel polypeptides of the invention, which are also referred to herein as mutant light-activated ion polypeptides can be expressed in specific cells, tissues, and/or organisms and used to control ion flux, proton flux, and/or excitation in cells in vivo, ex vivo, and in vitro in response to contact with one or more pulses of light of a suitable wavelength. In certain aspects of the invention, a mutant light-activated ion channel polypeptide of the invention is a mutant ChR2 light-activated ion channel polypeptide, a mutant Chrimson light-activated ion channel polypeptide, a mutant Chronos light-activated ion channel polypeptide. Non-limiting examples of mutant light-activated ion channels of the invention are Chrome, which has the amino acid sequence set forth herein as SEQ ID NO:11, and ChromeQ, which has an amino acid sequence set forth herein as SEQ ID NO:12.

Some embodiments of the invention include additional mutant light-activated ion channel polypeptides. For example, sequence alignment of an additional light-activated ion channel polypeptide sequence with a ChR2, Chrimson, or Chronos polypeptide sequence can be used to identify one or more positions for substitution with a replacement amino acid residue that corresponds to an amino acid substituted into a mutated ChR2, Chrimson, or Chronos sequence as described herein. Examples of additional art-known light-activated ion channel polypeptides, whose amino acid sequence may be aligned with the sequence of ChR2, Chrimson, or Chronos for identification of corresponding positions for one or more amino acid substitutions, include but are not limited to: ChIEF, C1V1, and ReaChR.

Some aspects of the invention include methods of preparing and using polynucleotide molecules (which may also be referred to herein as "genes") having nucleic acid sequences that encode a mutant light-activated ion channel or variant thereof of the invention. The invention, in part, also includes nucleic acid sequences that encode mutated light-activated ion channel polypeptides or variants thereof of the invention and also may include vectors and constructs that comprise such nucleic acid sequences. A construct of the invention may also include nucleic acid sequences that encode a trafficking molecule, a fluorescent molecule, or other label. Non-limiting examples of trafficking molecules include, ER2, KGC, etc. Non-limiting examples of florescent molecules that may be included in a vector or construct of the invention include GFP, Venus, etc. Additional art-known trafficking sequences and labeling molecule sequences, including but not limited to fluorescent molecule sequences, may be included in constructs and vectors of the invention. Some embodiments of the invention include expression of one or more mutant light-activated ion channel polypeptide of the invention encoded by the nucleic acid sequences, in cells, tissues, and organisms. As used herein, the phrases: "light-activated ion channel" and "light-activated channel" are used interchangeably.

A light-activated ion channel of the invention may also be referred to herein as a "Mutant" light-activated ion channel of the invention. Mutant light-activated ion channels and variants thereof of the invention can be expressed in a membrane of a cell and are activated by contact with light.

An ion channel is an integral membrane protein that forms a pore through a membrane and assists in establishing and modulating the small voltage gradient that exists across the plasma membrane of all cells. Ion channels are also located in subcellular membranes of organelles such as the endoplasmic reticulum (ER), mitochondria, etc. When a light-activated ion channel such as ChR2, Chronos, Chrimson is activated by contacting the cell under suitable conditions, such as with appropriate light, the pore opens and permits conductance of ions such as sodium, potassium, calcium, and protons etc. through the pore. Inclusion of one or more amino acid substitutions that are present in a mutant light-activated ion channel polypeptide of the invention may change the conductivity across the mutant channel, compared to the non-mutant channel. In some embodiments of the invention ion flux is $Ca^{++}$ flux.

Conduction of ions and/or protons across the pore of a wild-type light-activated ion channel polypeptide or a mutant light-activated ion channel polypeptide or variant thereof of the invention may also be referred to herein as the conductivity of the membrane that includes the pore. As used herein, an increase in conductivity of a membrane means an increase in conduction of one or more of ions and protons through an ion channel pore in the membrane; and a decrease in conductivity of a membrane means a decrease in conduction of one or more of ions and protons through an ion channel pore in the membrane. In certain embodiments of the invention, a mutant light-activated ion channel polypeptide or variant thereof that is present in a membrane may be contacted with a suitable dose of light to activate the ion channel, and a change in the conductivity of the membrane may result. In certain embodiments of the invention, a mutant light-activated ion channel or variant thereof may be expressed in a cell membrane and contacted with a suitable dose of light to alter conductivity across the membrane. As used herein, with respect to conductivity, the terms "alter", "modify", and "change" may be used interchangeably. In some embodiments of the invention altering conductivity may include decreasing conductivity of one or more of an ion and a proton across a membrane as compared to conductivity across a normal, non-mutant, or control membrane, and in certain embodiments of the invention altering conductivity may include increasing conductivity of one or more of an ion and a proton across a membrane as compared to conductivity across a normal, non-mutant membrane, or control membrane.

In some embodiments of the invention, mutant light-activated channels may be used to modify the transmembrane potential (and/or ionic composition) of cells (and/or their sub-cellular regions, and their local environment). For example, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration). In some embodiments, the presence of mutant light-activated ion channels of the invention in a membrane of one, two, three, or more (e.g. a plurality) of cells in a tissue or organism, can result in depolarization of the single cell or the plurality of cells by contacting the light-activated ion channels with light of suitable wavelength to activate the channel and increase conductivity of the membrane(s). The terms "conductance" and "conductivity" may be used interchangeably herein in reference to the movement of ions across a membrane.

Mutant Light-Activated Ion Channels

Mutant light-activated ion channels and variants thereof of the invention are transmembrane channel polypeptides that use light energy to open, permitting ion conductance through their pore across the membrane, thus altering the potential of the membrane in which they are expressed. Mutant light-activated ion channels of the invention have been found to be suitable for expression and use in mammalian cells without need for any kind of chemical supplement, and in normal cellular environmental conditions and ionic concentrations. Mutant light-activated ion channels of the invention have been found to differ from many previously identified channels in that the mutant light-activated ion channels have altered ion flux and/or proton flux compared to non-mutant light-activated ion channels from which they were derived.

A mutant light-activated ion channel of the invention may be activated by contacting the mutant channel with an appropriate wavelength of light. For example, mutant ChR2 light-activated ion channels of the invention can be contacted with light that activates non-mutant ChR2 light-activated ion channel. Suitable activation conditions, including but not limited to appropriate wavelengths of light, timing of illumination, pulse length, and other illumination parameters are known in the art for the non-mutant light-activated ion channels such as ChR2, Chrimson, Chronos, and additional light-activated ion channel polypeptides. [See for example, Boyden, E. et al., Nature Neuroscience 8, 1263-1268 (2005) and Nagel, G., et al. PNAS Nov. 25, 2003 vol. 100 no. 24 pp. 13940-13945; Klapoetke N C, et al., (March 2014). Nature Methods 11 (3): 338-46; US Patent Application Publication US2014/0324134, the contents of each of which is incorporated by reference herein in its entirety.]

Contacting an excitable cell that includes a mutant light-activated ion channel or functional variant thereof of the invention with a light in the activating range of wavelengths may strongly depolarize the cell. Suitable wavelengths of light that may be used to depolarize a cell expressing a mutant light-activated ion channel or variant thereof of the invention are known in the art in reference to the non-mutant versions of the mutant light-activated ion channels of the invention. As a non-limiting example, contacting a cell expressing a mutant ChR2 light-activated ion channel or variant thereof of the invention with illumination conditions that include one or more pulses of a wavelength of blue light that activates a non-mutant ChR2 light-activated ion channel may be used to activate a mutant ChR2 light-activated ion channel or variant thereof of the invention. In another non-limiting example, illumination conditions using a red light that activates a non-mutant Chrimson light-activated ion channel may be used to activate a mutant Chrimson light-activated ion channel or variant thereof of the invention.

Mutant light-activated ion channels or variants thereof of the invention may permit ion conductance and depolarization when contacted under suitable conditions with an appropriate wavelength of light. As will be understood by those in the art that the term: "depolarized" used in the context of cells means an upward change in the cell voltage. For example, in an excitable cell at a baseline voltage of about −65 mV, a positive change in voltage, e.g., up to 5, 10, 15, 20, 30, 40, or more millivolts (mV) is a depolarization of that cell. When the change in voltage is sufficient to reach the cell's spike initiation voltage threshold an action potential (e.g. a spike) results. When a cell is depolarized by activating a mutant light-activated ion channel of the invention with an appropriate wavelength of light, the cell voltage becomes more positive than the baseline level, and an incoming signal may more easily raise the cell's voltage sufficiently to reach the threshold and trigger an action potential in the cell. It has been discovered that by contacting a cell expressing a mutant light-activated ion channel or variant thereof of the invention with light in a suitable wavelength range to activate the mutant light-activated ion channel or variant thereof of the invention, the voltage of the cell becomes less negative and may rise by at least about 20, 30, 40, 50, 60, 70, 80, 90, 100, mV (depending on the cell type) thus, depolarizing the cell. As used herein, the term "activate" when used in reference to a mutant light-activated ion channel of the invention or a non-mutant light-activated ion channel, means to open the channel making it permissive to ion and/or proton flux (also referred to as: conduction) through the channel.

Specific ranges of wavelengths of light that in some embodiments of the invention are useful to activate a mutant light-activated ion channel or variant thereof of the invention are known in the art. It will be understood that a light of appropriate wavelength for activation and will have a power and intensity appropriate for activation. It is well known in the art that light pulse duration, intensity, and power are parameters that can be altered when activating a channel with light. Thus, a skilled artisan will be able to adjust power, intensity appropriately when using an art-known wavelength to activate a mutant light-activated ion channel, or variant thereof of the invention. A dose of light that contacts a mutant light-activated ion channel or variant thereof of the invention may be determined based on the wavelength, pulse length, and power of the light that contacts the mutant light-activated ion channel. Thus, as a non-limiting example, a dose may have a wavelength of 470 nm, a 4 ms pulse length, and a 0.5 mW/mm$^2$ power and another light dose may have a wavelength of 470 nm, a 3 ms pulse length and a 0.5 mW/mm$^2$ power. Those skilled in the art can utilize art-known methods to select a dose of light by independently selecting a wavelength, a pulse length, and a power for the light with which a mutant light-activated ion channel of the invention is contacted. In some embodiments, wavelength and pulse length may be held steady, and power incrementally increased to examine activation parameters of a mutant light-activated ion channel of the invention. Similarly, certain embodiments of the invention may include incremental wavelength increases while pulse length and power are held steady; or incremental pulse length increases while wavelength and power are held steady. In some embodiments of the invention two or more of wavelength, pulse length, and power of a light may be incrementally altered to examine the effect on activation of a mutant light-activated ion channel of the invention.

A benefit of a mutant light-activated ion channel of the invention is the ability to "tune" the mutant light-activated ion channel's response using appropriate illumination variables (e.g., wavelength, intensity, duration, etc.), which are also referred to herein as "dose", to activate the channel. Methods of adjusting illumination variables are well known in the art and representative methods can be found in publications such as: Lin, J., et al., Biophys. J. 2009 Mar. 4; 96(5):1803-14; Wang, H., et al., 2007 Proc Natl Acad Sci USA. 2007 May 8; 104(19):8143-8. Epub 2007 May 1, each of which is incorporated herein by reference. Thus, it is possible to utilize a narrow range of one or more illumination characteristics to activate a mutant light-activated ion channel of the invention.

Non-limiting examples of ions that can be moved through a mutant light-activated ion channel or pore of the invention include sodium ions, potassium ions, calcium ions, protons, etc. In some embodiments, a mutant light-activated ion channel of the invention has a lower level (e.g., amount) of ion flux and/or proton flux through its pore compared to the level of flux in a non-mutant control light-activated ion channel when under essentially the same conditions. In some embodiments, a mutant light-activated ion channel of the invention has a higher level, also referred to herein as "amount" of ion flux and/or proton flux through its pore versus a non-mutant control light-activated ion channel when under essentially the same conditions. In some aspects of the invention an activated mutant light-activated ion channel or variant thereof has an altered level of calcium ion flux than the level of calcium ion flux across an activated non-mutant version of the mutant light-activated ion channel. In some embodiments the level of flux of calcium ions and/or protons is lower than in the non-mutant version essentially the same conditions. In certain embodiments the level of flux of calcium ions and or protons is higher than in the mon-mutant version under essentially the same conditions.

Routine methods may be used to measure different ion currents for mutant light-activated ion channels of the invention. Mutant light-activated ion channels of the invention can be activated by sustained light and/or by light pulses and by permitting ion conductance upon activation, light-activated ion channels of the invention can depolarize cells and alter, (which may also be referred to herein as "change"), the voltage in cells and organelles in which they are expressed.

Certain embodiments of the invention include nucleic acid sequences that encode a mutant light-activated ion channel or variant thereof and methods that utilize such nucleic acids. Certain embodiments of the invention include mutant light-activated ion channel polypeptides or variants thereof and methods of use of the same. Mutant light-activated ion channel nucleic acid sequences and amino acid sequences used in aspects and methods of the invention may be "isolated" sequences. As used herein, the term "isolated" used in reference to a polynucleotide, nucleic acid sequence, polypeptide, or amino acid sequence means a polynucleotide, nucleic acid sequence, or polypeptide, amino acid sequence that is separate from its native environment and present in sufficient quantity to permit its identification or use. Thus, a nucleic acid or amino acid sequence that makes up a mutant light-activated ion channel polynucleotide or polypeptide molecule (or variant thereof) that is present in a vector, in a cell, tissue, or organism, etc., may be considered to be an isolated sequence if it did not originate in that cell, tissue, or organism. As used herein the term "host" used in reference to a membrane, cell, or organism means a membrane, cell, or organism in which a mutant light-activated ion channel or variant thereof of the invention is expressed. Examples of a host membrane, cell, tissue, or organism include, but are not limited to vertebrate membranes, invertebrate membranes, mammalian (including but not limited to non-human primate, human, dog, cat, horse, mouse, rat, etc.), insect (including but not limited to *Drosophila*, etc.), fish and avian membranes, cells, tissues, and organisms. In certain embodiments of the invention a membrane may be a plant membrane.

Mutant light-activated ion channels and variants thereof of the invention can be used to depolarize excitable cells in which one or more light-activated ion channels of the invention are expressed. In some embodiments, a mutant light-activated ion channel or a variant thereof of the invention, can be expressed in a sub-population of cells in a cell population that also includes one or more additional sub-populations of cells that express one or more mutant light-activated ion channels, which in some embodiments may be activated by the same or different wavelengths of light than the other mutant light-activated ion channels expressed. The expression of mutant light-activated ion channels that are activated by different wavelengths of light in distinct, separate, subpopulations in a cell population can permit application of different illumination parameters to the population with an effect of differentially activating the different subpopulations through the use specific wavelengths of light, thus permitting controlled activation of a mixed population of light-activated channels.

In some embodiments of the invention, mutant light-activated channels are used to modify the transmembrane potential (and/or ionic composition) of cells (and/or their sub-cellular regions, and their local environment). In particular, the use of inwardly rectifying cationic channels will depolarize cells by moving positively charged ions from the extracellular environment to the cytoplasm. Under certain conditions, their use can decrease the intracellular pH (and/or cation concentration) or increase the extracellular pH (and/or cation concentration).

In a non-limiting example of a combined expression strategy, a mutant Chrimson light-activated channel polypeptide can be expressed in a set of cells in a tissue and a mutant Chronos light-activated channel polypeptide can be expressed in another set of cells in the tissue. The mutant chronos light-activated channel may have photocurrent generation at all illumination wavelengths except for red wavelength illumination. For example, non-mutant Chronos can depolarize cells in response to <5 ms pulse of 50-100 $\mu$W $mm^{-2}$ of blue or green light with sufficient spectral independence from non-mutant Chrimson. Illuminating the tissue expressing a mutant Chrimson light-activated channel and a mutant Chronos light-activated channel with 630 nm light would preferentially depolarize the first set of cells, and illuminating the tissue with 470 nm light at low powers (<5 mW $mm^{-2}$) preferentially depolarizes the second set of cells, thus permitting multiple colors of light to be used to activate the different mutant light-activated channels different sets of cells in the same tissue.

Sequences

The present invention, in part, includes mutant novel light-activated ion channels, their expression in cell membranes, and their use to alter ion and/or proton flux across membrane in which they are expressed. The amino acid sequence of a ChR2 light-activated channel polypeptide is set forth herein as SEQ ID NO:1, a Chrimson light-activated ion channel polypeptide is set forth herein as SEQ ID NO:5, and a Chronos light-activated channel polypeptide is set forth herein as SEQ ID NO:8. Addition sequences of the invention are described herein. Mutant light-activated ion channel molecules of the invention include mutant ChR2, Chrimson, Chronos, and other mutant light-activated ion channel molecules and in some embodiments also include variants of the mutant light-activated ion channel molecules disclosed herein.

A mutant light-activated ion channel polypeptide of the invention or variant thereof comprises a modified sequence of the light-activated ion channel polypeptide of the invention from which is it is derived. As used herein the term "modified" or "modification" in reference to a polypeptide sequence refers to a change of one, two, three, four, five, six, or more amino acids in the sequence as compared to the sequence from which it was derived. For example, the polypeptide sequence of a mutant ChR2 light-activated ion channel polypeptide of the invention may be identical to a wild-type ChR2 polypeptide except that the mutant it has one, two, three, four, five, or more amino acid substitutions, deletions, insertions, or combinations thereof. Similarly, the sequence of a variant of a mutant light-activated ion channel polypeptide of the invention may be identical to the sequence of the mutant light-activated ion channel polypeptide from which it was derived, but may also have one, two, three, four, five, or more amino acid substitutions, deletions, insertions, or combinations thereof not present in the mutant light-activated ion channel polypeptide.

It will be understood that sequences of mutant light-activated ion channel polypeptides and variants thereof of the invention may be derived from various light-activated ion channel polypeptides, including but not limited to ChR2, Chrimson, Chronos, ChIEF, C1V1, ReaChR, or from other art-known channelrhodopsin sequences that correspond, at least in part, to light-activated ion channel polypeptide sequences disclosed herein. For example, SEQ ID NO:1, the wild-type amino acid sequence of ChR2 is shown in FIG. 1. Amino acid sequences of portions of ChR2, Chrimson, and Chronos are shown in FIG. 11A-B, which show Chr2 aligned with Chrimson (FIG. 11A), and Chr2 aligned with Chronos (FIG. 11B). Using standard sequence alignment methods one of ordinary skill in the art is able to align additional light-activated ion channel polypeptide sequences to determine the correspondence of a residue in one sequence with a residue in an aligned sequence. Thus, as a non-limiting example, one skilled in the art can ascertain that the residue at position 71 in the ChR2 sequence set forth as SEQ ID NO:3; corresponds to the residue at position 113 in the Chrimson sequence set forth as SEQ ID NO:7 and that residue at position 71 in the ChR2 sequence set forth as SEQ ID NO:4; corresponds to the residue at position 88 in the Chronos sequence set forth as SEQ ID NO:10.

Routine sequence alignment methods and techniques can be used to align two or more similar light-activated ion channel polypeptide sequences, including but not limited to wild-type and previously modified/mutated light-activated ion channel polypeptide sequences, thus providing a means by which a corresponding location of a modification made in one mutant light-activated ion channel polypeptide can be identified in another light-activated ion channel polypeptide sequence. For example, the corresponding position(s) of one or more substitutions such as A71S, E90A, H114G in the Chrome sequence set forth as SEQ ID NO:11 can be identified in aligned sequences including but not limited to: Chrimson, Chronos, etc. Similarly, the corresponding position(s) of modifications such as A71S, E90A, H114G, and R115S in the ChromeQ sequence set forth as SEQ ID NO:12 can be identified in aligned sequences including but not limited to: Chrimson, Chronos, etc. The mutated light-activated ion channel polypeptide sequences of the invention can be aligned with one or more other light-activated ion channel polypeptide sequences that are substantially similar in amino acid sequence to a mutated light-activated ion channel polypeptide sequence of the invention as set forth herein, to identify corresponding positions for the substitutions in the aligned sequences.

In some embodiments of the invention, certain substituted light-activated ion channel polypeptides are excluded as mutant light-activated ion channel polypeptides or variants thereof of the invention. For example, known light-activated ion channel polypeptides such as ChR2 having a H134R substitution, but not having one or more other newly identified substitutions disclosed herein, and polypeptides having certain E90 substitutions that are not in combination with one or more other newly identified substitutions disclosed herein, are in some embodiments, not included in the mutant light-activated ion channel polypeptides of the invention. For example, in certain embodiments of the invention a mutant light-activated ion channel polypeptide or variant thereof does not include one or more specific substitutions independently selected from the list of the A71S, I84L, I84V, E90A, E90D, E90N, E90P, E90Q, M91L, F98M, F102S, K103W, T112G, T112N, T112S, H114G, R115S, E123A, H134K, K205A, T250I, and T250Q amino acid substitutions in positions corresponding to the sequence set forth as SEQ ID NO:1 and certain embodiments of the invention, a mutant light-activated ion channel polypeptide or variant does not include a substitution in one or more of A71, I84, E90, M91, F98, F102, K103, T112, H114, R115, E123, H134, K205, and T250 in positions corresponding to the sequence set forth as SEQ ID NO:1. In non-limiting examples, in certain embodiments of the invention, a mutant light-activated ion channel of the invention does not include a E90 substitution and in certain embodiments, a mutant light-activated ion channel of the invention does not include an H134 substitution, and in some embodiments of the invention, a mutant light-activated ion channel of the invention does not include an E90P substitution, and in certain embodiments of the invention, a mutant light-activated ion channel of the invention thereof does not include an H134R substitution, etc., in positions corresponding to the sequence set forth as SEQ ID NO:1.

As another non-limiting example, in certain embodiments of the invention, a mutant light-activated ion channel polypeptide of the invention or variant thereof, does not include one or more of a G113S, V126L, E132A, E132D, E132N, E132P, E132Q, V133L, V133L, I140M, F144S, S145W, T154G, N156G, H157S, E165A, L174C, K247A, S292I, and S292Q amino acid substitution in a position corresponding to the sequence set forth as SEQ ID NO:5 and in certain embodiments of the invention, a mutant light-activated ion channel polypeptide or variant thereof does not include a substitution of one or more of the amino acids G113, V126, E132, V133L, I140, F144, S145, T154, N156, H157, E165, L174, K247, and S292 in positions corresponding to the sequence set forth as SEQ ID NO:5. In non-limiting examples, in certain embodiments of the invention, a mutant light-activated ion channel of the invention does not include a E132 substitution, in certain embodiments, a mutant light-activated ion channel of the invention does not include a K247 substitution, in some embodiments of the invention, a mutant light-activated ion channel of the invention does not include an E133Q substitution, and in certain embodiments of the invention, a mutant light-activated ion channel of the invention, does not include an K176R substitution, etc., in positions corresponding to the sequence set forth as SEQ ID NO:5.

As another non-limiting example, in certain embodiments of the invention, a mutant light-activated ion channel polypeptide of the invention or variant thereof, does not include one or more of a G88S, V101L, E107A, E107D, E107N, E107P, E107Q, L115M, V119S, D120W, N129G, A132S, M140A, L149C, H151K, K222A, L267I, L267Q in positions corresponding to the sequence set forth as SEQ ID NO:8 and in certain embodiments of the invention, a mutant light-activated ion channel polypeptide or variant thereof does not include a substitution of one or more of the amino acids G88, V101, E107, L115, V119, D120, N129, A132, M140, L149, H151, K222, L267 in positions corresponding to the sequence set forth as SEQ ID NO:8. In non-limiting examples, in certain embodiments of the invention, a mutant light-activated ion channel of the invention does not include a E107 substitution, in certain embodiments, a mutant light-activated ion channel of the invention does not include a H151 substitution, in some embodiments of the invention, a mutant light-activated ion channel of the invention does not include an E107D substitution, and in certain embodiments of the invention, a mutant light-activated ion channel of the invention, does not include an H151K substitution, etc, in positions corresponding to the sequence set forth as SEQ ID NO:8.

Mutant light-activated ion channel and variants thereof can be identified based on sequence similarity to the sequence of the ChR2, Chrimson, Chronos, or other sequences and in view of teaching provided herein regarding activity and function of mutant light-activated ion channels of the invention, additional sequences (mutants or variants of mutants) can be identified. The presence of functionality, e.g., activation of a channel by contact with suitable light can be determined using methods described herein and art-known methods, and functional mutant light-activated ion channel polypeptides or variants thereof can be used in methods described herein. It is understood that that the level of sequence identity with a mutant light-activated ion channel of the invention, or variant thereof, plus functionality with respect to activation by suitable light contact can be characteristics used to identify additional light-activated ion channels using standard procedures for sequence alignment, comparisons, and assays for ion channel activity. Additional mutant light-activated ion channel polypeptides and variants thereof having one or more substitutions or other modifications can be identified and tested for characteristics including, but not limited to: expression, cell localization, activation and silencing in response to contact with light using methods and sequences disclosed herein in conjunction with art-known methods.

In some embodiments of the invention, the amino acid sequence of a variant mutant light-activated ion channel polypeptide of the invention has at least 80%, 85%, 90%, 91%, 92%, 93%, 94%, or 95% amino acid sequence identity to the amino acid sequence of the mutant light-activated ion channel polypeptide. In certain aspects of the invention a variant of a mutant light-activated ion channel polypeptide has at least 95% identity, at least 96% identity, at least 97% identity, at least 98% identity, or at least 99% identity to the mutant light-activated ion channel polypeptide of the invention. In certain embodiments of the invention, a mutant light-activated ion channel polypeptide of the invention or variant thereof has at least 80%, 85%, 90%, 95%, 96%, 97%, 98%, 99%, or 100% identity to the polypeptide sequence of the light-activated ion channel polypeptide sequence from which it was derived. As a non-limiting example, a variant of Chrome set forth herein as SEQ ID NO: 11, or a variant of ChromeQ, set forth herein as SEQ ID NO:12, may have at least 80%, 85%, 90%, 95%, 96%, 97%, 98%, or 99% identity to the sequence from which it was derived, in this example, the sequence of Chrome or ChromeQ, respectively.

Additional amino acid substitutions, deletions, and/or insertions in the sequence of a mutant light-activated ion channel polypeptide of the invention that result in a variant of the mutant light-activated ion channel polypeptide may be constrained with respect to the extent of permissible modifications from the amino acid sequence of mutant light-activated ion channel polypeptide in order to permit the mutant light-activated ion channel polypeptide variant to have all, or at least a portion of the level of function of the mutant light-activated ion channel polypeptide from which is was derived, when the variant is contacted with light under suitable conditions to activate the channel. In some aspects of the invention, a variant of a mutant light-activated ion channel polypeptide of the invention has at least 10%, 20%, 30%, 40%, 50%, 60%, 70%, 80%, 90%, or 100% of the level of light-activated function of the mutant light-activated ion channel polypeptide from which the variant was derived.

As used herein, the term "identity" refers to the degree of relatedness or similarity between two or more polypeptide sequences (or nucleic acid sequences), which may be determined by the alignment and match between the sequences. The percentage is obtained as the percentage of identical amino acids in two or more sequences taking account of gaps and other sequence features. The identity between polypeptide sequences can be determined by means of art-known procedures. Algorithms and programs are available and routinely used by those in the art to determine identity between polypeptide sequences and to determine identity between nucleic acid sequences. Non-limiting examples of programs and algorithms include BLASTP, BLASTN and FASTA (Altschul et al., NCB NLM NIH Bethesda Md. 20894; Altschul et al., 1990), Online BLAST programs from the National Library of Medicine are available, for example, at blast.ncbi.nlm.nih.gov/Blast.cgi.

A mutant light-activated ion channel polypeptide of the invention may be shorter or longer than the light-activated ion channel polypeptide from which it was derived. In some aspects of the invention, a mutant light-activated ion channel polypeptide or variant thereof may be a full-length mutant variant of the sequence from which it was derived, or may be a functional fragment of the sequence from which it was derived.

Sequence modifications can be one or more of substitutions, insertions, and deletions and any combination thereof. Modified sequences, (which may also be referred to as variants) ordinarily are prepared by site specific mutagenesis of nucleic acids in the DNA encoding a light-activated ion channel polypeptide, using cassette or PCR mutagenesis or other techniques known in the art, to produce DNA encoding the modified light-activated ion channel polypeptide and thereafter expressing the DNA in recombinant cell culture. Amino acid sequence variants are characterized by the predetermined nature of the variation, a feature that sets them apart from naturally occurring allelic or interspecies variation of light-activated ion channel polypeptides. Mutant light-activated ion channel polypeptides and variants thereof of the invention can be identified and tested for characteristics including, but not limited to: expression, cell localization, activation and depolarization and depolarization effects in response to contact with light using methods disclosed herein. Mutant light-activated ion channel polypeptides and variants thereof may exhibit the same qualitative biological activity as the polypeptide from which they are derived, although mutants and variants can also be selected which have modified characteristics.

A site or region for introducing an amino acid sequence modification may be predetermined, and the mutation per se need not be predetermined. For example, to optimize the performance of a mutation at a given site, random mutagenesis may be conducted at the target codon or region and the expressed mutant light-activated ion channel polypeptide or variant thereof screened for the optimal combination of desired activity. Techniques for making substitution mutations at predetermined sites in DNA having a known sequence are well known, for example, M13 primer mutagenesis and PCR mutagenesis.

Function or activity of a mutant light-activated ion channel polypeptide or variant thereof of the invention can be tested using methods described herein for characteristics including, but not limited to: expression, cell localization, activation and depolarization in response to contact with light using methods disclosed herein. Types of sequence modifications that may be included in a mutant light-activated ion channel polypeptide or variant thereof include, but are not limited to conservative amino acid substitutions, which will produce molecules having functional characteristics similar to those of the polypeptide from which the mutant or variant sequence was derived. Conservative amino acid substitutions are substitutions that do not result in a significant change in the activity or tertiary structure of a selected polypeptide. Such substitutions typically involve replacing a selected amino acid residue with a different residue having similar physico-chemical properties. For example, substitution of Glu for Asp is considered a conservative substitution because both are similarly sized, negatively charged amino acids. Groupings of amino acids by physico-chemical properties are known to those of skill in the art. The following groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

Amino acid substitutions may made to 1, 2, 3, 4, 5, 6, 7, 8, 9, 10, 11, 12, 13, 14, 15, or more single residues; and insertions may be on the order of from about 1, 2, 3, 4, 5, 6, 7, 8, 9, 10, 11, 12, 13, 14, 15, or more amino acids, and larger insertions may be tolerated. Deletions may range from about 1, 2, 3, 4, 5, 6, 7, 8, 9, 10, 11, 12, 13, 14, 15, or more. Substitutions, deletions, insertions or any combination thereof may be used to arrive at a final mutant light-activated ion channel polypeptide or variant thereof of the invention. Generally these changes are done on a few amino acids to minimize the alteration of the molecule. However, larger changes may be tolerated in certain circumstances.

Mutant light-activated ion channel polypeptides or variants thereof of the invention may exhibit the same qualitative light-activated ion channel activity as the light-activated ion channel polypeptide from which they were derived, and/or may show one or more altered characteristics such as altered photocurrent, stability, speed, compatibility, and toxicity, or a combination thereof. For example, the a mutant light-activated ion channel polypeptide of the invention may modified with additional substitutions, insertions or deletions such that the resulting variant has an increased photocurrent and/or has less toxicity than the mutant light-activated ion channel polypeptide from which it was derived.

A mutant light-activated ion channel polypeptide or variant thereof of the invention may in some embodiments, incorporate unnatural amino acids as well as natural amino acids. An unnatural amino acid can be included in a mutant light-activated ion channel polypeptide or variant thereof of the invention to enhance a characteristic such as photocurrent, stability, speed, compatibility, or to lower toxicity, etc.

Specific amino acid locations and/or residues for substitution have now been identified that alone, or in combination of two or more have been demonstrated to be particularly effective at altering one or more of ion flux and proton flux across membranes in which mutant light-activated ion channel polypeptides or variants thereof of the invention have been expressed. For example, nine mutants (A71S, I84L, I84V, E90A, E90D, E90N, E90P, E90Q, and E123A) of ChR2 showed reduced calcium flux compared to the non-mutated ChR2 from which they were derived. Six mutants (E90A, E90N, M91L, H114G, R115S, and K205A) showed reduced proton flux compared to the non-mutated ChR2 from which they were derived. In addition to mutant light-activated ion channel polypeptides of the invention with decreased ion flux and/or proton flux, some mutants were found to have increased calcium or proton flux. In addition to the previously known mutant ChR2 having an L132C, six mutants (K103W, T112G, T112N, T112S, H134K, and T250I) were found that showed increased calcium flux compared to the non-mutated ChR2 from which they were derived. Five mutants showed increased proton flux (I84L, E90D, F98M, F102S, T250Q) compared to the non-mutated ChR2 from which they were derived. Some aspects of the invention include mutant light-activated ion channel polypeptides derived from Chrimson or Chronos polypeptide sequences comprising one or more substitutions at positions corresponding to those described for mutant ChR2 light-activated ion channel polypeptides. A description of such substitutions is provided in Table 2.

TABLE 2

Identified ChR2 substitutions of embodiments the invention are shown in column 1. Columns 2 and 3 indicate the number/position of the residue in the Chrimson and Chronos polypeptides that correspond to the ChR2 substitution positions. The original and substituted amino acids at each substitution position are identified for Chrimson, and Chronos, in columns 2 and 3, respectively. The amino acid numbers correspond to the amino acid positions in SEQ ID NO: 1 for ChR2, SEQ ID NO: 5 for Chrimson, and SEQ ID NO: 8 for Chronos.

| ChR2 | Chrimson | Chronos |
|---|---|---|
| A71S | G113S | G88S |
| I84L, I84V | V126L | V101L |
| E90A, E90D, | E132A, E132D, | E107A, E107D, |
| E90N, E90P, E90Q | E132N, E132P, E132Q | E107N, E107P, E107Q |
| M91F, M91L | V133F, V133L | L108F |
| V94L | V136L | C111L |
| F98M, F98V | I140M, I140V | L115M, L115V |
| F99A, F99E, | F141A, F141E, | F116A, F116E, |
| F99R, F99T, F99V | F141R, F141T, F141V | F116R, F116T, F116V |
| F102L, F102N, | F144L, F144N, | V119L, V119N, |
| F102P, F102S, F102T | F144P, F144S, F144T | V119P, V119S, V119T |
| K103G, K103P, | S145G, S145P, | D120G, D120P, |
| K103T, K103W | S145T, S145W | D120T, D120W |
| A111C, A111G, | S153C, S153G, | T128C, T128G, |
| A111L, A111S | S153L | T128L, T128S |
| T112G, T112N, T112S | T154G, T154N, T154S | N129G, N129S |
| H114G, H114V | N156G, N156V | G131V |
| R115P, R115S | H157P, H157S | A132P, A132S |
| Q117L, Q117P, Q117Y | Y159L, Y159P | I134L, I134P, I134Y |
| E123A | E165A | M140A |
| L132C | L174C | L149C |
| H134K, H134R | K176R | H151K, H151R |
| T188L | M230L | C205L |
| K205A, K205V | K247A, K247V | K222A, K222V |
| Q210L, Q210V | M252L, M252V | K227L, K227V |
| T250I, T250Q | S292I, S292Q | L267I, L267Q |

It will be understood that such identifications of corresponding residues in aligned sequences may also be made based on the alignment of ChR2 with C1V1, ChIEF, ReaChR or other suitable light-activated ion channel polypeptide. In certain aspects of the invention, a mutant light-activated ion channel polypeptide or variant thereof of the invention may include an independently selected combination of substitutions disclosed herein. Thus, a mutant light-activated ion channel polypeptide or variant thereof may have 1, 2, 3, 4, 5 or more of the disclosed amino acid substitutions. In certain embodiments of the invention, inclusion of a two, three, four or more substitutions identified herein in a mutant light-activated ion channel polypeptide or variant thereof expressed in a membrane, may result in a synergistic effect of the substitutions on one or more of the ion flux and proton flux across the mutant light-activated ion channel and membrane in which it is expressed.

Another aspect of the invention provides nucleic acid sequences that code for a mutant light-activated ion channel polypeptide or variant thereof of the invention. It will be understood by a person of skill in the art that the mutant light-activated ion channel polypeptides and variants thereof of the present invention can be coded for by various nucleic acids. Each amino acid in the protein is represented by one or more sets of 3 nucleic acids (codons). Because many amino acids are represented by more than one codon, there is not a unique nucleic acid sequence that codes for a given protein. It is well understood by those of skill in the art how to make a nucleic acid that can code for mutant light-activated ion channel polypeptides and variants thereof of the invention by knowing the amino acid sequence of the polypeptide. A nucleic acid sequence that codes for a polypeptide or protein is the "gene" of that polypeptide or protein. A gene can be RNA, DNA, or other nucleic acid than will code for the polypeptide or protein.

It is understood in the art that the codon systems in different organisms can be slightly different, and that therefore where the expression of a given protein from a given organism is desired, the nucleic acid sequence can be modified for expression within that organism. Thus, in some embodiments, a mutant light-activated ion channel or variant thereof of the invention is encoded by a mammalian-codon-optimized nucleic acid sequence, which may in some embodiments be a human-codon optimized nucleic acid sequence.

Delivery of Mutant Light-Activated Ion Channels and Variants Thereof

Delivery of a mutant light-activated ion channel polypeptide or variant thereof of the invention, to a cell and/or expression of a mutant light-activated ion channel polypeptide or variant thereof of the invention, in a cell can be done using art-known delivery means. (see, for example Chow et al. Nature 2010 Jan. 7; 463(7277):98-102.)

In some embodiments of the invention a mutant light-activated ion channel polypeptide of the invention is included in a fusion protein. It is well known in the art how to prepare and utilize fusion proteins that comprise a polypeptide sequence. In certain embodiments of the invention, a fusion protein can be used to deliver a mutant light-activated ion channel, or variant thereof, to a cell and can also in some embodiments be used to target a mutant light-activated ion channel or variant thereof, of the invention to specific cells or to specific cells, tissues, or regions in a subject. Targeting and suitable targeting sequences for delivery to a desired cell, tissue or region can be performed using art-known procedures.

It is an aspect of the invention to provide a mutant light-activated ion channel polypeptide or variant thereof of the invention that is non-toxic, or substantially non-toxic in cells in which it is expressed. In the absence of light, a light-activated ion channel of the invention does not significantly alter cell health or ongoing electrical activity in the cell in which it is expressed.

In some embodiments of the invention, a mutant light-activated ion channel, or variant thereof, of the invention is genetically introduced into a cellular membrane, and reagents and methods are provided for genetically targeted expression of mutant light-activated ion channel polypeptides and variants thereof. Genetic targeting can be used to deliver mutant light-activated ion channel polypeptides and variants of the invention to specific cell types, to specific cell subtypes, to specific spatial regions within an organism, and to sub-cellular regions within a cell. Genetic targeting also relates to the control of the amount of a mutant light-activated ion channel polypeptide, or variant thereof, that is expressed, and the timing of the expression.

Some embodiments of the invention include a reagent for genetically targeted expression of a mutant light-activated ion channel polypeptide or variant thereof, wherein the reagent comprises a vector that contains the gene for the mutant light-activated ion channel polypeptide or variant thereof.

As used herein, the term "vector" refers to a nucleic acid molecule capable of transporting between different genetic environments another nucleic acid to which it has been operatively linked. The term "vector" also refers to a virus or organism that is capable of transporting the nucleic acid molecule. One type of vector is an episome, i.e., a nucleic acid molecule capable of extra-chromosomal replication. Some useful vectors are those capable of autonomous replication and/or expression of nucleic acids to which they are linked. Vectors capable of directing the expression of genes to which they are operatively linked are referred to herein as "expression vectors". Other useful vectors, include, but are not limited to viruses such as lentiviruses, retroviruses, adenoviruses, and phages. Vectors useful in some methods of the invention can genetically insert a mutant light-activated ion channel polypeptides and variants thereof of the invention, into dividing and non-dividing cells and can insert mutant light-activated ion channel polypeptides and variants thereof of the invention to cells that are in vivo, in vitro, or ex vivo cells.

Vectors useful in methods of the invention may include additional sequences including, but not limited to one or more signal sequences and/or promoter sequences, or a combination thereof. Expression vectors and methods of their use are well known in the art. Non-limiting examples of suitable expression vectors and methods for their use are provided herein. In certain embodiments of the invention, a vector may be a lentivirus comprising the gene for a mutant light-activated ion channel or variant thereof of the invention. A lentivirus is a non-limiting example of a vector that may be used to create stable cell line. The term "cell line" as used herein is an established cell culture that will continue to proliferate given the appropriate medium.

Promoters that may be used in methods and vectors of the invention include, but are not limited to, cell-specific promoters or general promoters. Methods for selecting and using cell-specific promoters and general promoters are well known in the art. A non-limiting example of a general purpose promoter that allows expression of a mutant light-activated ion channel polypeptide or variant thereof in a wide variety of cell types—thus a promoter for a gene that is widely expressed in a variety of cell types, for example a "housekeeping gene" can be used to express a mutant light-activated ion channel polypeptide, or variant thereof, in a variety of cell types. Non-limiting examples of general promoters are provided elsewhere herein and suitable alternative promoters are well known in the art.

In certain embodiments of the invention, a promoter may be an inducible promoter, examples of which include, but are not limited to tetracycline-on or tetracycline-off, or tamoxifen-inducible Cre-ER.

Methods of Use of Mutant Light Activated Ion Channels and Variants Thereof

Mutant light activated ion channels, and variants thereof of the invention are well suited for targeting cells and specifically altering voltage-associated cell activities. In some embodiments of the invention, light-activated ion channels of the invention can be utilized to change one or more of ion flux and proton flux across cell membranes, thus activating endogenous signaling pathways (such as calcium dependent signaling, etc.), and then drugs can be applied that modulate the response of the cell (using a calcium or voltage-sensitive dye). This allows drug screening using just light to activate the channels of interest, and using just light to read out the effects of a drug on the channels of interest.

The performance of the above-described molecules can be tuned for optimal use, particularly in context of their use in conjunction with other molecules or optical apparatus. Such tuning can be done using standard methods known in the art. For example, in order to achieve optimal contrast for multiple-color stimulation, one may desire to either improve or decrease the performance of one molecule with respect to one another, by the appendage of trafficking enhancing sequences (non-limiting examples of which include ER2, KGC, etc.) or creation of genetic variants by site-directed mutagenesis, directed evolution, gene shuffling, or altering codon usage. Different mutant light-activated ion channel molecules, or variants thereof, may have inherently varying spectral sensitivity from each other. This may be used to advantage in vivo (where scattering and absorption will vary with respect to wavelength, coherence, and polarization), by tuning the linearity or non-linearity of response to optical illumination with respect to time, power, and illumination history.

Cells and Subjects

Some aspects of the invention include cells used in conjunction with one or more mutant light-activated ion channels-encoding-nucleic acids and mutant light-activated ion channel polypeptides (and variants thereof). A cell in which a mutant light-activated ion channel of the invention or variant may be expressed and may be used in methods of the invention include prokaryotic and eukaryotic cells. In certain embodiments of the invention, useful cells may be mammalian cells; including but not limited to cells of humans, non-human primates, dogs, cats, horses, rodents, etc. In some embodiments of the invention, useful cells may be non-mammalian cells; including but not limited to insect cells, avian cells, fish cells, plant cells, etc. Examples of cells in which a mutant light-activated ion channel or variant thereof of the invention may be expressed are non-excitable cells and excitable cells, the latter of which includes cells able to produce and respond to electrical signals. Examples of excitable cell types include, but are not limited, to neurons, muscles, cardiac cells, and secretory cells (such as pancreatic cells, adrenal medulla cells, pituitary cells, etc.).

Non-limiting examples of cells that may be used in methods of the invention include: neuronal cells, nervous system cells, cardiac cells, circulatory system cells, visual system cells, auditory system cells, secretory cells, endocrine cells, or muscle cells. In some embodiments, a cell used in conjunction with methods and ion channels of the invention may be a healthy normal cell, which is not known to have a disease, disorder or abnormal condition. In some embodiments, a cell used in conjunction with methods and mutant light-activated ion channels of the invention may be an abnormal cell, for example, a cell that has been diagnosed as having a disorder, disease, or condition, including, but not limited to a degenerative cell, a neurological disease-bearing cell, a cell model of a disease or condition, an injured cell, etc. In some embodiments of the invention, a cell may be a control cell.

Mutant light-activated ion channels and variants thereof of the invention may be expressed in cells from culture, cells in solution, cells obtained from subjects, and/or cells in a subject (in vivo cells). Mutant light-activated ion channels and variants thereof of the invention may be expressed and activated in cultured cells, cultured tissues (e.g., brain slice preparations, etc.), and in living subjects, etc. As used herein, a the term "subject" may refer to a human, non-human primate, cow, horse, pig, sheep, goat, dog, cat, bird, rodent, insect, or other vertebrate or invertebrate organism. In certain embodiments, a subject is a mammal and in certain embodiments a subject is a human.

Controls and Candidate Compound Testing and Drug Screening

Mutant light-activated ion channels and variants thereof of the invention and methods using mutant light-activated ion channels and variants thereof of the invention can be utilized to assess changes in cells, tissues, and subjects in which they are expressed. Some embodiments of the invention include use of mutant light-activated ion channels and variants thereof of the invention to identify effects of candidate compounds on cells, tissues, and subjects. Results of testing a mutant light-activated ion channel or variant thereof of the invention can be advantageously compared to a control. In some embodiments of the invention one or more mutant light-activated ion channels or variant thereof of the invention, may be expressed in a cell population and used to test the effect of candidate compounds on the cells. A "test" cell, membrane, tissue, or organism may be a cell, tissue, or organism in which activity of a light-activated ion channel of the invention may be tested or assayed. Results obtained using assays and tests of a test cell, membrane, tissue, or organism may be compared results obtained from the assays and tests performed in other test cells, membranes, tissues or organisms or assays and tests performed in control cells, membranes, tissues, or organisms.

As used herein a control value may be a predetermined value, which can take a variety of forms. It can be a single cut-off value, such as a median or mean. It can be established based upon comparative groups, such as cells or tissues that include the mutant light-activated ion channel or variant thereof and are contacted with light, but are not contacted with a candidate compound and the same type of cells or tissues that under the same testing condition are contacted with the candidate compound. Another example of comparative groups may include cells or tissues that have a disorder or condition and groups without the disorder or condition. Another example of comparative groups may include cells or tissues in which a light-activated ion channel from which the mutant light-activated ion channel of the invention was derived, is expressed. Another comparative group may be cells from a group with a family history of a disease or condition and cells from a group without such a family history. A predetermined value can be arranged, for example, where a tested population is divided equally (or unequally) into groups based on results of testing. Those skilled in the art are able to select appropriate control groups and values for use in comparative methods of the invention.

As a non-limiting example of use of a mutant light-activated ion channel or variant thereof to identify a candidate therapeutic agent or compound, a mutant light-activated ion channel or variant thereof of the invention may be expressed in an excitable cell in culture or in a subject and the excitable cell may be contacted with a light that activates the mutant light-activated ion channel or variant thereof and with a candidate therapeutic compound. In one embodiment, a test cell that includes a mutant light-activated ion channel or variant thereof of the invention can be contacted with a light that depolarizes the cell and also contacted with a candidate compound. A control cell in such an example may be a cell that includes the mutant light-activated ion channel or variant thereof that is not contacted with the activating light and/or the candidate compound or a light-activated ion channel from which the mutant light-activated ion channel of the invention was derived, etc. The cell, tissue, and/or subject that include the cell can be monitored for the presence or absence of a change that occurs in the test conditions versus the control conditions. For example, in a cell, a change may be a change in the depolarization or in a depolarization-mediated cell characteristic in the test cell versus a control cell, and a change in depolarization or the depolarization-mediated cell characteristic in the test cell compared to the control may indicate that the candidate compound has an effect on the test cell or tissue that includes the cell. In some embodiments of the invention, a depolarization-mediated cell characteristic may be a an action potential, pH change in a cell, release of a neurotransmitter, etc. and may in come embodiments, include a downstream effect on one or more additional cells, which occurs due to the depolarization of the cell that includes the mutant light-activated ion channel, or variant thereof of the invention. Art-known methods can be used to assess depolarization and depolarization-mediated cell characteristics and changes to the depolarization or depolarization-mediated cell characteristics upon activation of a mutant light-activated ion channel or variant thereof of the invention, with or without additional contact with a candidate compound.

Candidate-compound identification methods of the invention that are performed in a subject, may include expressing a mutant light-activated ion channel or variant thereof in a subject, contacting the subject with a light under suitable conditions to activate the light-activated ion channel and depolarize the cell, and administering to the subject a candidate compound. The subject is then monitored to determine whether any change occurs that differs from a control effect in a subject. In addition, for example, a cell in culture can be contacted with a light appropriate to activate a mutant light-activated ion channel or variant thereof of the invention in the presence of a candidate compound. A result of such contact with the candidate compound can be measured and compared to a control value as a determination of the presence or absence of an effect of the candidate compound on the cell.

Methods of identifying effects of candidate compounds using mutant light-activated ion channels, and variants thereof, of the invention may also include additional steps and assays to further characterizing an identified change in the cell, tissue, or subject when the cell is contacted with the candidate compound.

In a non-limiting example of a candidate drug identification method of the invention, cells that include a mutant light-activated ion channel, or variant thereof of the invention are depolarized, thus triggering release of a neurotransmitter from the cell, and then drugs are applied that modulate the response of the cell to depolarization (determined for example using patch clamping methods or other suitable art-known means). Such methods enable drug screening using light to activate the channels of interest, and using light to read out the effects of a drug on the channels and channel-containing cells of interest.

In some embodiments, a mutant light-activated ion channel polypeptide or variant thereof of the invention can be used in test systems and assays for assessing membrane protein trafficking and physiological function in heterologously expressed systems and the use of use of light-activated channels to depolarize a cell.

In some embodiments of the invention, testing in a cell, tissue, or subject can also include one or more cells that has a mutant light-activated ion channel or variant thereof of the invention, and that also has one, two, three, four or more additional different light-activated ion channels, wherein at least one, two, three, four or more of the additional light-activated ion channels is activated by contact with light having a different wavelength than used to activate the mutant light-activated ion channel, or variant thereof of the invention. Thus, in some aspects of the invention, two-color assays (or assays utilizing 3, 4, 5, or more wavelength colors) can be performed.

It will be understood that combinations of 2, 3, 4, or more light-activated ion channels including but not limited to mutant light-activated ion channels and variants thereof of the invention may be expressed in separate subpopulations of a population of cells and then exposed to doses of light in a manner as described here to optimize their use in assays and treatments of the invention. A non-limiting example of a process to prepare and use a multi-light activated population of cells is as follows. A first light-activated ion channel is expressed in a first subpopulation of a population of cells; a second light-activated ion channel is expressed in a second subpopulation of the population of cells, wherein the first and second subpopulations are non-overlapping subpopulations, and the first light-activated ion channel and second light activated ion channel are have ranges of activating light wavelengths that do not entirely overlap. The population of cells is contacted with a plurality of first light test doses comprising combinations of wavelength, pulse width, and power that activate the first subpopulation, and the transmembrane voltage deflection is measured in a cell of the second subpopulation of cells contacted with the first light test doses. The first light test dose that includes a maximum light power that activates the light activated ion channel in first subpopulation of cells and results in a minimum sub-threshold transmembrane voltage deflection in the second subpopulation of cells is determined. The population of cells is then contacted with a plurality of first light test doses comprising a lower power than the maximum first light power that was determined, and a first light test doses that activate the first light activated ion channel (at the lower powers) are determined. The population of cells is then contacted with a plurality of second light test doses that include combinations of light wavelength, pulse width, and power that activate the second subpopulation, and a second light test dose comprising a second light power that activates the second subpopulation of cells is determined. Assays can be performed using such a population of cells, that includes contacting the population of cells with the first light test dose and the second light test dose determined using the steps above. The above-described process of optimizing light dose parameters for multi-light activated ion channels can be used to design and implement assays that include light-activated ion channels of the invention, as well as other light-activated ion channels that are known in the art.

A non-limiting example of a procedure for optimizing the use of two-color activated populations of cells is provided as follows. A population that has mutant light-activated ion channel or variants thereof of the invention that are derived from Chronos and Chrimson expressed in different subpopulations is contacted with blue light having a wavelength between 400 nm and 500 nm, or between 450 nm to 500 nm, and having a pulse width of between 1 and 5 ms for activation. A pulse width of 5 ms provides for minimum sub-threshold crosstalk in the blue light, which is defined as <15 mV, <10 mV, and optimally as <5 mV. The maximum blue light power that can be used is determined using by patch clamping Chrimson-derived mutant light-activated ion channel-expressing cells, illuminating with blue light and measuring voltage deflection. Optimally using blue light power such that maximum voltage deflection is <10 mV, which in some embodiments may be 0.4 to 0.6 mW/mm$^2$. The optimal blue light power that can be used to drive the Chronos-derived mutant light-activated ion channel of the invention is determined using the same conditions as above, except using lower light power, such as 50 µW/mm$^2$ to 0.4 mW/mm$^2$, which in some embodiments may be 0.2 mW/mm$^2$. Power depends on expression system and cell type used to prepare the population. The population can be contacted with red light having a wavelength, for example, of between 600 nm and 735 nm, 620 nm and 640 nm, or 570 nm and 650 nm, and with a pulse width of between 1 and 5 ms for activation, which in some embodiments may be optimized at 5 ms. In certain embodiments of the invention, the optimal light power to drive the Chrimson-derived mutant light-activated ion channel of the invention in the red may be determined by ramping light powers from for example, 0.1 mW/mm$^2$ to 100 mW/mm$^2$, or from 0.5 mW/mm$^2$ to 10 mW/mm$^2$.

Methods of Treatment Using Mutant Light-Activated Ion Channel and Variant Thereof Some aspects of the invention include methods of treating a disorder or condition in a cell, tissue, or subject using mutant light-activated ion channels or variants thereof of the invention. Treatment methods of the invention may include administering to a subject in need of such treatment, a therapeutically effective amount of a mutant light-activated ion channel or variant thereof of the invention to treat the disorder. It will be understood that a treatment may be a prophylactic treatment or may be a treatment administered following the diagnosis of a disease or condition. A treatment of the invention may reduce or eliminate a symptom or characteristic of a disorder, disease, or condition or may eliminate the disorder, disease, or condition itself. It will be understood that a treatment of the invention may reduce or eliminate progression of a disease, disorder or condition and may in some instances result in the regression of the disease, disorder, or condition. A treatment need not entirely eliminate the disease, disorder, or condition to be effective. In some embodiments of the invention one or more mutant light-activated ion channels or variants of the invention may be expressed in a cell population and used in methods to treat a disorder or condition.

Administration of a mutant light-activated ion channel or variant thereof of the invention may include administration of a pharmaceutical composition that includes a cell, wherein the cell expresses the mutant light-activated ion channel, or variant thereof. Administration of a mutant light-activated ion channel or variant thereof, of the invention may include administration of a pharmaceutical composition that includes a vector, wherein the vector comprises a nucleic acid sequence encoding the mutant light-activated ion channel or variant thereof, and the administration of the vector results in expression of the mutant light-activated ion channel, or variant thereof in a cell in the subject. A composition of the invention optionally includes a carrier, which may be a pharmaceutically acceptable carrier.

A mutant light-activated ion channel molecule (polypeptide or encoding polynucleotide) of the invention may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. According to methods of the invention, the compound may be administered in a composition, which in some embodiments may be a pharmaceutical composition. In general, a pharmaceutical composition comprises the compound of the invention and a pharmaceutically-acceptable carrier. Pharmaceutically acceptable carriers are well known to the skilled artisan and may be selected and utilized using routine methods. As used herein, a pharmaceutically-acceptable carrier means a non-toxic material that does not interfere with the effectiveness of the biological activity of the active ingredients.

Pharmaceutically acceptable carriers may include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention.

An effective amount of a mutant light-activated ion channel or variant thereof of the invention is an amount that increases the level of the mutant light-activated ion channel or variant thereof, in a cell, tissue, or subject to a level that is beneficial for the subject. An effective amount may also be determined by assessing physiological effects of administration on a cell or subject, such as a decrease in symptoms following administration. Other assays will be known to those skilled in the art and can be employed for measuring the level of the response to a treatment. The amount of a treatment may be varied for example by increasing or decreasing the amount of the mutant light-activated ion channel or variant thereof that is administered, by changing the therapeutic composition in which the mutant light-activated ion channel is administered, by changing the route of administration, by changing the dosage timing, by changing the activation amounts and parameters of a light-activated ion channel of the invention, and so on. The effective amount will vary with the particular condition being treated, the age and physical condition of the subject being treated; the severity of the condition, the duration of the treatment, the nature of the concurrent therapy (if any), the specific route of administration, and the like factors within the knowledge and expertise of the health practitioner. For example, an effective amount may depend upon the location and number of cells in the subject in which the mutant light-activated ion channel is to be expressed. An effective amount may also depend on the location of the tissue to be treated.

Effective amounts will also depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. In general, for therapeutic use, a maximum dose of a composition to increase the level of a mutant light-activated ion channel or variant thereof, and/or to alter the length or timing of activation of a mutant light-activated ion channel or variant thereof in a subject (alone or in combination with other therapeutic agents) may be used, that is the highest safe dose or amount according to sound medical judgment. It will be understood by those of ordinary skill in the art, however, that a health-care provider or patient may insist upon a lower dose or tolerable dose for medical reasons, psychological reasons or for virtually any other reasons.

A mutant light-activated ion channel or variant thereof of the invention may be administered using art-known methods. In some embodiments a nucleic acid that encodes a mutant light-activated ion channel polypeptide of the invention is administered to a subject and in certain embodiments a light-activated ion channel polypeptide is administered to a subject. The manner and dosage administered may be adjusted by the individual physician or veterinarian, particularly in the event of any complication. The absolute amount administered will depend upon a variety of factors, including the material selected for administration, whether the administration is in single or multiple doses, and individual subject parameters including age, physical condition, size, weight, and the stage of the disease or condition. These factors are well known to those of ordinary skill in the art and can be addressed with no more than routine experimentation.

Pharmaceutical compositions that deliver mutant light-activated ion channels or variants thereof of the invention may be administered alone, in combination with each other, and/or in combination with other drug therapies, or other treatment regimens that are administered to subjects. A pharmaceutical composition used in the foregoing methods preferably contain an effective amount of a therapeutic compound that will increase the level of a mutant light-activated ion channel polypeptide or variant thereof to a level that produces the desired response in a unit of weight or volume suitable for administration to a subject.

The dose of a pharmaceutical composition that is administered to a subject to increase the level of the mutant light-activated ion channel or variant thereof in cells of the subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The amount and timing of activation of a mutant light-activated ion channel of the invention (e.g., light wavelength, length of light contact, etc.) that has been administered to a subject can also be adjusted based on efficacy of the treatment in a particular subject. Parameters for illumination and activation of mutant light-activated ion channels that have been administered to a subject can be determined using art-known methods and without requiring undue experimentation.

Various modes of administration will be known to one of ordinary skill in the art that can be used to effectively deliver a pharmaceutical composition to increase the level of a mutant light-activated ion channel or variant thereof of the invention in a desired cell, tissue or body region of a subject. Methods for administering such a composition or other pharmaceutical compound of the invention may be topical, intravenous, oral, intracavity, intrathecal, intrasynovial, buccal, sublingual, intranasal, transdermal, intravitreal, subcutaneous, intramuscular, and/or intradermal administration. The invention is not limited by the particular modes of administration disclosed herein. Standard references in the art (e.g., Remington's Pharmaceutical Sciences, 18th edition, 1990) provide modes of administration and formulations for delivery of various pharmaceutical preparations and formulations in pharmaceutical carriers. Other protocols which are useful for the administration of a therapeutic compound of the invention will be known to one of ordinary skill in the art, in which the dose amount, schedule of administration, sites of administration, mode of administration (e.g., intra-organ) and the like vary from those presented herein.

Administration of a cell or vector to increase a level of a mutant light-activated ion channel or variant thereof, in a mammal other than a human; and administration and use of mutant light-activated ion channels or variants thereof of the invention, e.g. for testing purposes or veterinary therapeutic purposes, is carried out under substantially the same conditions as described above. It will be understood by a skilled artisan that this invention is applicable to both human and animals. Thus, in certain embodiments, this invention is intended to be used in husbandry and veterinary medicine as well as in human therapeutics.

In some aspects of the invention, methods of treatment using a mutant light-activated ion channel or variant thereof of the invention are applied to cells including but not limited to a neuronal cell, a nervous system cell, a neuron, a cardiac cell, a circulatory system cell, a visual system cell, an auditory system cell, a muscle cell, or an endocrine cell, etc.

Disorders, Diseases and Conditions for Treatment with Mutant Light-Activated Ion Channels and Variants Thereof Disorders and conditions that may be treated using methods of the invention to express mutant light-activated ion channels or variants thereof of the invention in a cell, tissue, and/or subject may include, but are not limited to: injury, brain damage, spinal cord injury, epilepsy, metabolic disorders, cardiac dysfunction, vision loss, blindness, deafness, hearing loss, and neurological conditions (e.g., Parkinson's disease, Alzheimer's disease, seizure), degenerative neurological conditions, etc. In some embodiments of the invention, a disorder or condition may be treated by expressing a mutant light-activated ion channel or variant thereof in at least one cell and contacting the at least one cell with a wavelength of light suitable to increase ion conductance in the cell. In some embodiments of the invention, such treatments include restoring function in a cell that has a disease or condition, by contacting one or more cells that expresses a mutant light-activated ion channel or variant thereof with a suitable wavelength of light to drive activity patterns in the cell to restore a function in the cell and to ameliorate one or more symptoms of the disorder or condition.

Mutant light-activated ion channels or variants thereof of the invention may be used to target cells and membranes, and to alter voltage-associated cell activities. In some aspects of the invention, a mutant light-activated ion channel or variant thereof of the invention may be used to increase or decrease the pH of a cell in which it is expressed. Such a technique may be used to treat alkalosis in a cell, tissue or subject.

Another aspect of the invention includes methods of using light-activated proton pumps in conjunction with the use of mutant light-activated ion channels or variants thereof of the invention for the coupled effect of hyperpolarization and intracellular alkalinization. For example, both phenomena can induce spontaneous spiking in neurons by triggering hyperpolarization-induced cation currents or pH-dependent hyper-excitability. Another aspect of the invention is to express mutant light-activated ion channels or variants thereof of the invention into cell membranes and then to activate the light-activated ion channels and generate subcellular voltage or pH gradients, particularly at synapses and in synaptic vesicles to alter synaptic transmission, and mitochondria to improve ATP synthesis in a cell, tissue, or subject.

Another aspect of the invention is the use mutant light-activated ion channels of the invention with light to perform non-invasive transcranial and/or transdural stimulation to modulate neural circuits. Another aspect of the invention is the various compositions of matter that have now been reduced to practice, for example: plasmids encoding for the above genes have been prepared; lentiviruses carrying payloads encoding for the above genes have been prepared; adeno-associated viruses carrying payloads encoding for the above genes have been prepared; cells expressing the above genes have been prepared.

Working operation of a prototype of this invention was demonstrated by genetically expressing a mutant light-activated ion channel molecule of the invention in excitable cells, illuminating the cells with suitable wavelengths of light and demonstrating changes in one or more of ion flux and proton flux across the channel. Depending on the particular implementation, methods of the invention allow light control of cellular functions in vivo, ex vivo, and in vitro.

In non-limiting examples of methods of the invention, mutant light-activated ion channels of the invention may be used in mammalian cells without need for any kind of chemical supplement, and in normal cellular environmental conditions and ionic concentrations. For example, genes encoding mutant light-activated ion channels of the invention have been used in implementations of the invention. These sequences in humanized or mouse-optimized form allow depolarization at wavelengths described herein.

In some embodiments of the invention, treatment methods utilizing mutant light-activated ion channels or variants thereof may be used for the treatment of visual system disorders, for example to treat vision reduction or loss. A mutant light-activated ion channel of the invention may be administered to a subject who has a vision reduction or loss and the expressed light-activated ion channel can function as light-sensitive cells in the visual system, thereby permitting a gain of visual function in the subject.

The present invention in some aspects, includes one or more of preparing nucleic acid sequences that encode mutant light-activated ion channel polypeptides and variants thereof; expressing in cells and membranes polypeptides encoded by the prepared nucleic acid sequences; illuminating the cells and/or membranes with suitable light, and demonstrating rapid depolarization of the cells and/or a change in conductance (one or more of ion flux and proton flux) across the membrane in response to light, as well as rapid release from depolarization upon cessation of light. The ability to controllably alter voltage across membranes and cell depolarization with light has been demonstrated. The present invention enables light-control of cellular functions in vivo, ex vivo, and in vitro, and the mutant light activated ion channels of the invention and their use, have broad-ranging applications for drug screening, treatments, and research applications, some of which are describe herein.

EXAMPLES

Example 1

Methods
Molecular Cloning.
Mammalian codon-optimized ChR2 (1-310) that constitutes the light-activated channel function [Prigge, M., et al., J Biol Chem, 2012. 287(38):31804-12; Schneider, F., D. et al., Biophys J, 2013. 105(1):91-100] from C. reinhardtii was cloned into pEGFP-N3 vector (Clontech) as a BamHI-AgeI fragment, with mCherry as the fluorophore.
Culture and Transfection of HEK293FT Cells.
HEK293FT cells (Invitrogen) were cultured in phenol red-free high-glucose DMEM (Gibco) supplemented with 10% heat-inactivated fetal bovine serum (HyClone) and 1 mM sodium pyruvate, maintained in a 5% $CO_2$ humidified incubator. The cells were plated on optical bottom 24 or 96-well plates (Greiner Bio-One) coated with 2% Growth Factor Reduced Matrigel (BD Biosciences) in DMEM for 1 h at 37° C. at a density of 20,000 cells per well or 6,000 cells per well respectively, which resulted in a confluent layer of cells that allowed the center of the wells to be consistently imaged. 24 h after plating cells, the media was replaced with fresh media (500 μL for 24-well and 50 μL for 96-well) and placed in the incubator for 1-2 h at 37° C. before transfection.

For transfection, each library plasmid was diluted in pUC18 plasmid that does not replicate in mammalian cells at a mass ratio of 1:100 to reduce uptake of multiple plasmids by a cell as described previously [Zhang, F., et al., Nat Neurosci, 2008. 11(6):63 1-3]; having on average a single copy of a library plasmid per cell allows the detection of activity from each mutant. 625 ng of total plasmid DNA mixed with 1.563 μL of 2M $CaCl_2$ (250 mM final concentration) in 12.5 μL $ddH_2O$ was mixed rapidly and thoroughly with 12.5 μL of 2×HEPES buffered-saline (2×HBS) (50 mM HEPES, 280 mM NaCl, 1.5 mM $Na_2HPO_4$, pH 7.0) to obtain a transfection mix (for a 4 well transfection; for larger or smaller numbers of well, the recipes were scaled accordingly). The transfection mix was incubated 30 s at room temperature and 5 μL was added to each well. The plates were placed in the incubator for 16-18 hrs, and the media in each well was replaced with 100 μL of prewarmed culture media containing 2 μM all-trans retinal (Sigma). While the addition of all-trans retinal is not required for ChR2 to achieve photocurrent in HEK cells, it was desired to prototype a screen that could be of general use in screening for opsins, even those that had smaller affinities for all-trans retinal. For transfecting cells in 24-well plates, all steps were identical as above except the DNA mix for each well contained 1.25 μg total plasmid DNA, 3.125 μL 2M $CaCl_2$ in 25 μL $ddH_2O$ and mixed with 25 μL of 2×HBS.
Intracellular Calcium and pH Imaging.
The image acquisition protocols (filter cubes, exposure times, etc.) were largely based on previous publications that quantified intracellular calcium and pH change due to channelrhodopsin photocurrent using Fura-2 and SNARF 5-AM [Lin, J. Y., et al., Biophys J, 2009. 96(5):1803-14], in addition to previous experience in imaging pH change in Arch-expressing cells [Agarwal, N. & E. V. Shusta, Proteomics, 2009. 9(4):1099-108].

For intracellular calcium imaging, 15,000 HEK293FT cells were plated in glass-bottom 24-well plates (Greiner Bio-one) per well, transfected using the same procedure as in the voltage imaging. The cells were washed with Tyrode's solution, and stained with 5 mM Fura-2 AM (Invitrogen) in Tyrode's solution at room temperature for 30 min. After dye loading, the cells were incubated in Tyrode's solution for 10 min for recovery. The cells were washed twice and imaged in an extracellular solution composed of 80 mM $CaCl_2$, 20 mM glucose, 23 mM N-methyl-D-glucamine, 5 mM NaCl, 3 mM KCl, 1 mM $MgCl_2$, and 10 mM HEPES, pH 7.3.

Channelrhodopsin expression was detected by mCherry fluorescence using DG-4 (Semrock 575/15) and imaged using a dichroic (600 LP Chroma) paired with an emission filter (640/50 Chroma). Fura-2 was excited with DG-4 using emission filters (Semrock 340/26 at 0.25 $mW/mm^2$ and 387/11 at 0.40 $mW/mm^2$; light powers at this level did not result in significant activation of wild-type ChR2) and imaged using a filter cube (Chroma, 495 dichroic paired with 500 long pass emission filter) with a CMOS camera (Hamamatsu Orca Flash 2.8) with 250 ms and 300 ms of exposure time for 340 and 380 nm emission, respectively. Images were taken with 1 s interval for 4 s to measure baseline calcium levels, followed by a 10 s illumination with DG-4 (Chroma 470/22 at 6.8 $mW/mm^2$) to activate channelrhodopsins. Following channelrhodopsin activation, images were taken every 1 s for 30 s. Ratio of fluorescence at 340/380 was used as an indicator of intracellular calcium concentration. The 340/380 fluorescence ratio was calibrated to a known intracellular calcium concentration using a calcium calibration buffer kit (Invitrogen) and ionomycin (Invitrogen) following manufacturer's instructions with solutions provided (free calcium concentrations between 0 to 1.35 mM) containing Fura-2 and fitted to the calibration curve ($R^2$=0.986)

$$\log[Ca^{2+}]_{free} = \log K_d + \log\left[\left(\frac{R - R_{min}}{R_{max} - R}\right) \times \frac{F_{max}380}{F_{min}380}\right]$$

where R indicates the ratio of 340/380 nm emission, F380 indicates 380 nm emission, subscripts min and max indicates measurements at $[Ca^{2+}]_{free}$ of 0 and 1.35 µM, respectively.

For intracellular pH imaging, channelrhodopsin constructs were cloned into pN3-EGFP vector (Clontech) as EGFP fusions to avoid spectral overlap between fluorophore and dye emission. HEK293FT cells transfected in glass-bottom 24-well plates (Nunc) were stained with 5 mM SNARF-5F AM (Invitrogen) at room temperature for 30 min. After loading, the cells were washed with Tyrode's solution and incubated for 10 min for recovery. The cells were washed twice and imaged in an extracellular solution that consisted of 1 mM CaCl2, 20 mM glucose, 145 mM NaCl, 3 mM KCl, 1 mM MgCl2, and 10 mM HEPES, pH 7.35. SNARF-5F and channelrhodopsins were simultaneously excited with DG-4 (Semrock 500/15 nm, at 4 $mW/mm^2$), then SNARF-5F emissions were imaged at 640 nm (Chroma, 600 LP dichroic, 640/50 nm filter; 200 ms exposure) and 610 nm (Chroma, 565 LP dichroic, 610/70 nm filter, 300 ms exposure), for a total illumination period of 1 s. Finally, EGFP expression was imaged (Chroma, 535/30 nm filter, 100 ms exposure, using 470/22 nm at 2.5 $mW/mm^2$). The 640/610 nm emission ratio after 1 s illumination was used as the parameter to monitor intracellular pH change. A small amount of residual bleed-through of EGFP fluorescence in the 610 nm and 640 nm channel was corrected by quantifying images of cytosolic EGFP expressing cells acquired under the same setting, and plotting the bleed-through of EGFP vs the EGFP emission measured at 535 nm, which yielded a linear curve ($R^2$=0.897). The ratio of 640/610 nm emission to intracellular pH was calibrated according to manufacturer's protocol with solutions (pH 6.5-8) containing 110 mM K-gluconate, 10 mM NaCl, 25 mM KCl, 1 mM $MgCl_2$, 10 mM HEPES, and 20 mM nigericin (Invitrogen) and fitted to the calibration curve ($R^2$=0.984)

$$pH = pK_A - \log\left[\left(\frac{R - R_B}{R_A - R}\right) \times \frac{F_B 640}{F_A 640}\right]$$

where R indicates the ratio of 640/610 nm emission, F640 indicates 640 nm emission, subscripts A and B indicates measurements at pH 6.5 and 8, respectively.

Electrophysiology Recording.

Whole-cell patch clamp recordings were performed in isolated HEK293FT cells. All recordings were performed on an inverted microscope (Leica DMI6000B) using an Axopatch 200B amplifier and Digidata 1440 digitizer (Molecular Devices) at room temperature. In order to allow isolated cell recording, cells were plated at a density of 15,000 cells per well in 24-well plates that contained round glass coverslips (0.15 mm thick, 25 mm in diameter, coated with 2% Growth Factor Reduced Matrigel in DMEM for 1 h at 37° C.). In order to make accurate measurements, data from cells with access resistance less than 25 MΩ, holding current less than ±50 pA were used. Typical membrane resistance was between 500 MΩ-2 GΩ and pipette resistance was between 4-10 MΩ.

For comparing (peak and steady-state) photocurrents, and channel closing rate, recordings were performed using Tyrode's solution as the extracellular solution, and an intracellular solution consisting of (in mM) 125 K-Gluconate, 8 NaCl, 0.1 $CaCl_2$, 0.6 $MgCl_2$, 1 EGTA, 10 HEPES, 4 MgATP, 0.4 NaGTP, pH 7.3 (KOH adjusted), with 295-300 mOsm (sucrose adjusted).

For assessing ion selectivity in channelrhodopsins, the extracellular and intracellular solutions shown in Table 3 were used with extracellular osmolarity of 290-300 mOsm (sucrose adjusted) and intracellular osmolarity of 285 mOsm (sucrose adjusted).

TABLE 3

| Solution | [Na] (mM) | [K] (mM) | [Ca] (mM) | [H] (mM) | pH | Other (mM) |
|---|---|---|---|---|---|---|
| Intracellular | 0 | 140 | 0 | 5.10E−05 | 7.40 | 5 EGTA, 2 $MgCl_2$, 10 HEPES |
| 145 mM NaCl | 145 | 5 | 1 | 5.10E−05 | 7.40 | 10 HEPES, 5 glucose, 2 $MgCl_2$ |
| 145 mM KCl | 0 | 145 | 1 | 5.10E−05 | 7.40 | 10 HEPES, 5 glucose, 2 $MgCl_2$ |
| 90 mM $CaCl_2$ | 0 | 5 | 90 | 5.10E−05 | 7.40 | 10 HEPES, 5 glucose, 2 $MgCl_2$ |
| 135 mM NMDG | 5 | 5 | 1 | 5.10E−04 | 6.40 | 135 NMDG, 10 HEPES, 5 glucose, 2 $MgCl_2$ |

Photostimulation of patch clamped cells was conducted by a 470 nm LED (Thorlabs) at 10 $mW/mm^2$ unless otherwise stated. 1 s illumination was delivered for measuring peak and steady-state components of the photocurrent, and 2 ms illumination was delivered and the decay of photocurrent was fitted to a monoexponential curve using Clampfit (Molecular Devices) to determine the channel closing rate $e_{(Toff)}$.

Fluorescence from patch clamped cells was quantified by drawing a line around the patched cell manually using ImageJ and calculating the average intensity over the entire area. Background fluorescence was calculated by averaging the intensity in an area within the same image without any cell, and subtracted from the cell fluorescence. All statistical comparisons were performed using JMP (SAS) unless mentioned otherwise.

In order to measure reversal potentials, liquid junction potentials were determined for each intracellular-extracellular solution pair as previously described [Neher, E., Methods Enzymol, 1992. 207:123-3 1]. Using the intracellular solutions in the methods, the liquid junction potentials were 5.8 mV, and 4.9 mV, for 90 mM $CaCl_2$ and 135 mM NMDG, respectively, and were corrected during recording; the others were <1 mV in liquid junction potential. Reversal potential for each mutant was determined by first measuring photocurrents at holding potentials between −80 to +80 mV in 20 mV steps to get a rough estimate, and then in 5 mV steps near the reversal, which allowed linear fits (typical $R2=0.98$). Reversal potentials were calculated from equations for the linear fits in Excel (Microsoft). In order to calculate reversal potential for the steady-state photocurrents, photocurrents were averaged over the final 300 ms of a 1 s illumination. In order to estimate permeability ratios, the reversal potential measurements were fitted to a modified Goldman-Hodgkin-Katz equation with a correction for divalent cations [Chang, D. C., Biophys J, 1983. 43(2):149-56] as has been done previously for ChR2 [Lin, J. Y., et al., Biophys J, 2009. 96(5):1803-14] using MATLAB.

Results.
Channelrhodopsin-2 Mutants with Altered Calcium and Proton Selectivity.

Figure 2C:
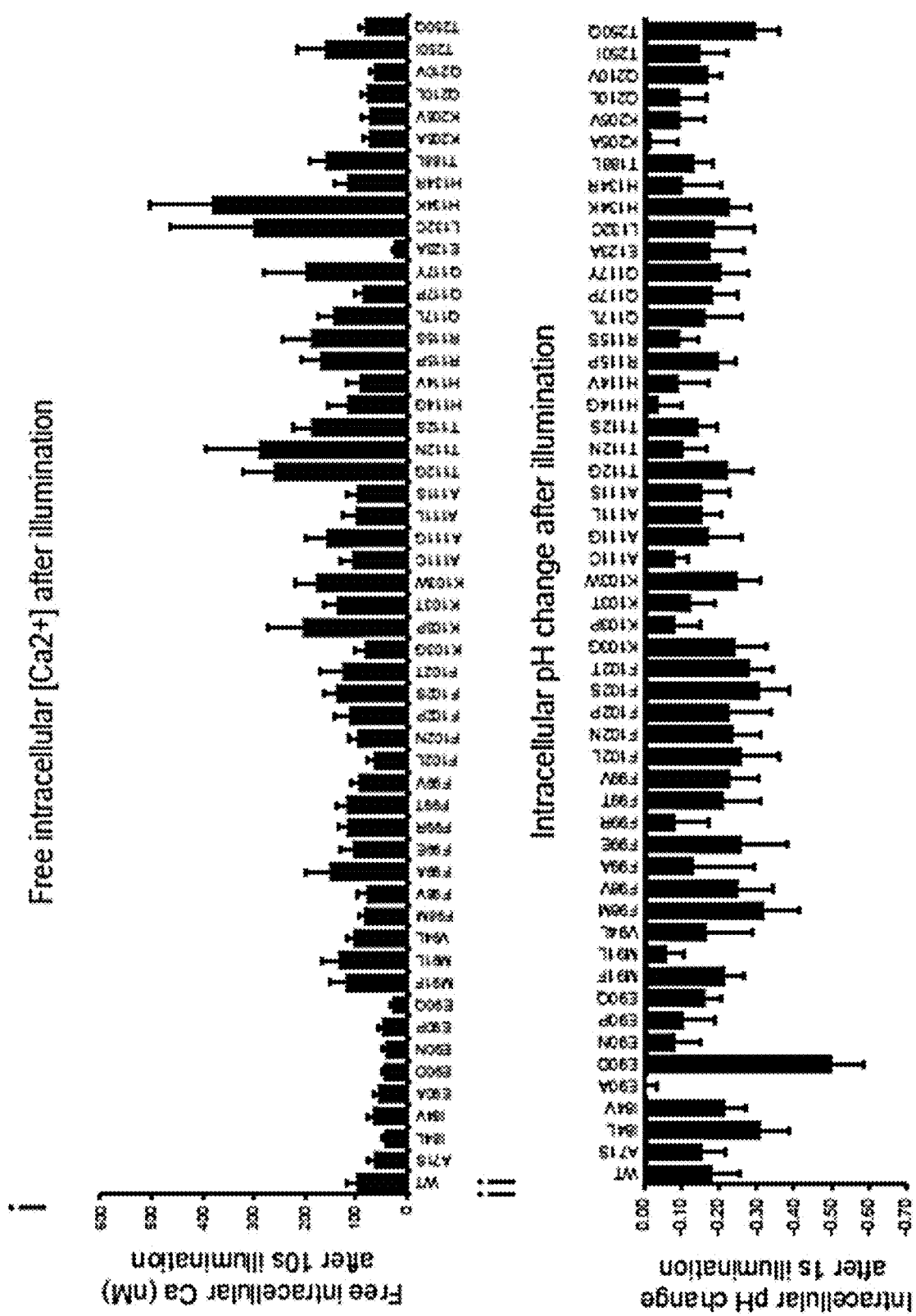

Mutants of ChR2 were screened for reduced calcium and proton flux, using fura-2 [Lin, J. Y., et al., Biophys J, 2009. 96(5): p. 1803-14; Kleinlogel, S., et al., Nat Neurosci, 2011. 14(4): p. 5 13-8.] to measure calcium flux (FIG. 2Ai), and SNARF-5F [21] to measure proton flux (FIG. 2Aii). Mutants were screened according to the appropriate calculated fluorescence ratios for fura-2 (FIG. 2Bi) and SNARF-5F (FIG. 2Bii), and also calculated intracellular free calcium (FIG. 2Ci) and pH change (FIG. 2Cii) in the screening conditions. Nine mutants (A71S, I84L, I84V, E90A, E90D, E90N, E90P, E90Q, and E123A) showed reduced calcium flux compared to ChR2 (FIG. 2Bi; n=12-69 HEK293FT cells, P<0.05 non Bonferroni-corrected t-test comparing 340/380 emission ratio after 10 s illumination to that of ChR2). Six mutants (E90A, E90N, M91L, H114G, R115S, and K205A) showed reduced proton flux (FIG. 2Bii, n=8-35 HEK293FT cells, P<0.05 non Bonferroni-corrected t-test comparing pH change after 1 s illumination to that of wild-type ChR2). In addition, a few had increased calcium or proton flux: in addition to the previously known mutant L132C, Six mutants (K103W, T112G, T112N, T112S, H134K, and T250I) were found that showed increased calcium flux (FIG. 2Bi; n=21-46 HEK293FT cells, P<0.05 non Bonferroni-corrected t-test comparing 340/3 80 emission ratio after 10 s illumination to that of wild-type ChR2), and five that increased proton flux (I84L, E90D, F98M, F102S, T250Q) (FIG. 2Bii, n=9-16 HEK293FT cells, P<0.05 non Bonferroni-corrected t-test comparing pH change after 1 s illumination to that of wild-type ChR2). These latter mutants may provide residues for future constructs with greater calcium or proton conducting properties.

Figure 2D:
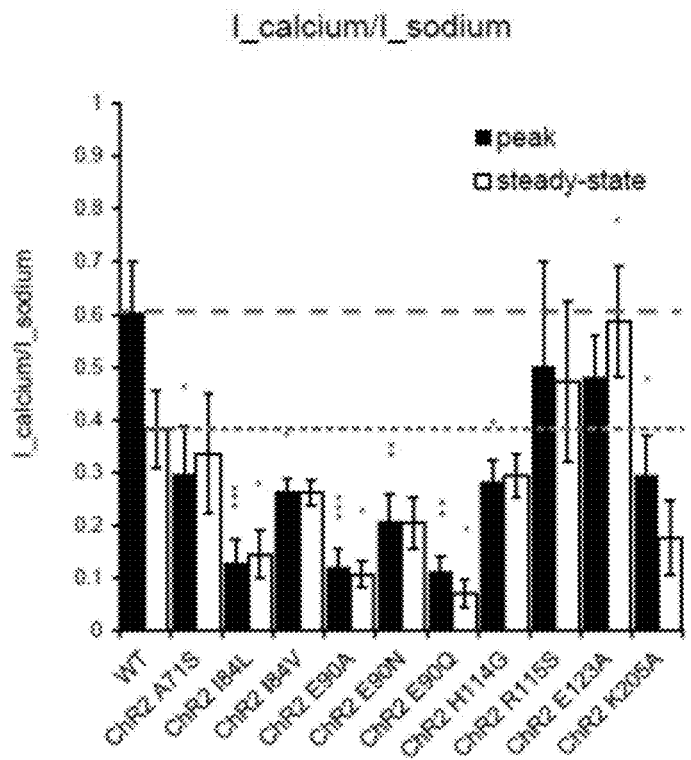
Figure 2E:
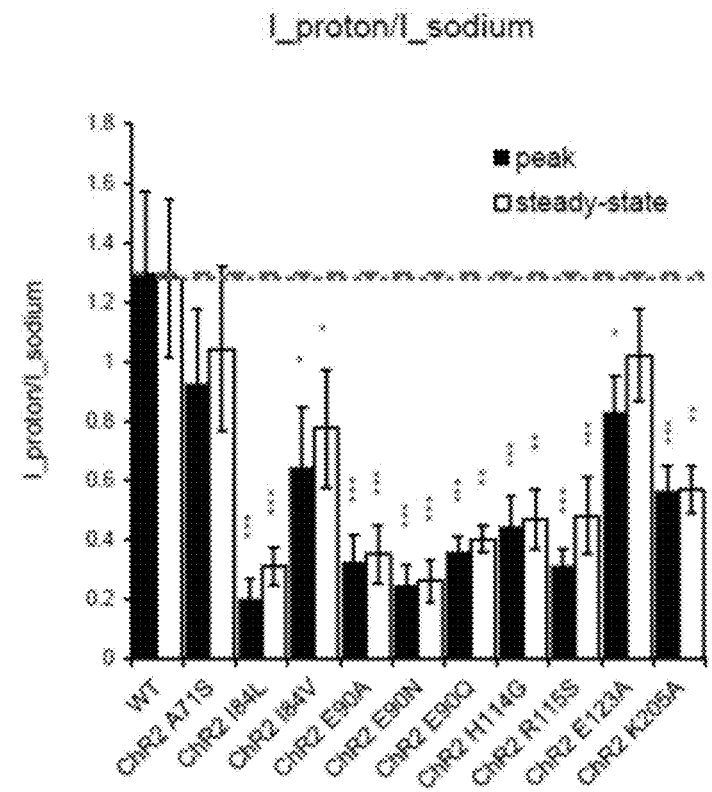

FIGS. 2A-E graphically depict results of physiological screening for calcium and proton selectivity. (FIG. 2A) Change in Fura-2 340/380 nm emission ratio (i) and SNARF-5F 640/610 nm emission ratio (ii) mediated by previously described channelrhodopsins. Cells expressing fluorophores only were used as controls (mCherry in (i) and EGFP in (ii)) (n=20-35 cells each). (FIGS. 2B, 2C) Outcome of the calcium and proton selectivity of the screen for channelrhodopsins, showing the Fura-2 340/380 ratio (FIG. 2Bi) and calcium concentration (FIG. 2Ci) after blue light illumination (delivered as in FIG. 2A) in HEK cells expressing indicated ChR2 mutants (n=12-69 cells), and the SNARF-5F 640/610 ratio (FIG. 2Bii) and pH (FIG. 2Cii) after green light illumination (delivered as in FIG. 2A, but with is pulses) in HEK cells expressing indicated ChR2 mutants (n=8-35 cells). (FIGS. 2D, 2E) Population data for photocurrent density ratios, measured using whole-cell patch clamp in HEK cells in ion-specific extracellular solutions, for calcium photocurrent (I_calcium) measured in 90 mM $CaCl_2$, pH 7.4 divided by sodium photocurrent (I_sodium) measured in 145 mM NaCl, pH 7.4 (FIG. 2D), and proton photocurrent (I_proton) measured in 135 mM NMDG, pH 6.4 divided by sodium photocurrent (I_sodium) (FIG. 2E), of wild-type ChR2 and mutants with improved ion selectivity identified from FIGS. 2B and 2C, using illumination conditions 470 nm, 1 s, 10 mW/mm$^2$ (n=5-10 HEK293FT cells each). In FIGS. 2D and 2E, peak and steady-state photocurrent ratios for wild-type ChR2 are indicated by dashed lines and dotted lines, respectively.

Figure 4A:
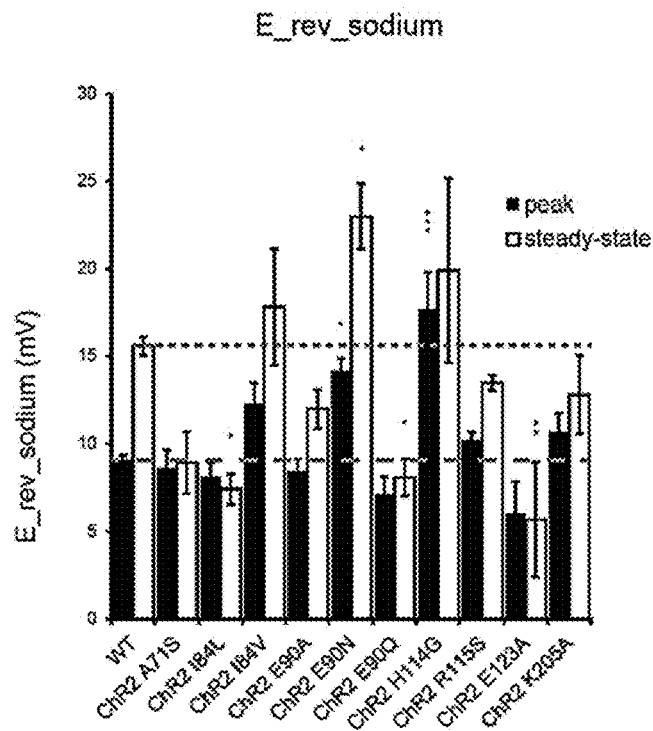
FIGS. 4A-E depict reversal potential measurements for ChR2 mutants with improved ion selectivity.
Figure 5A:
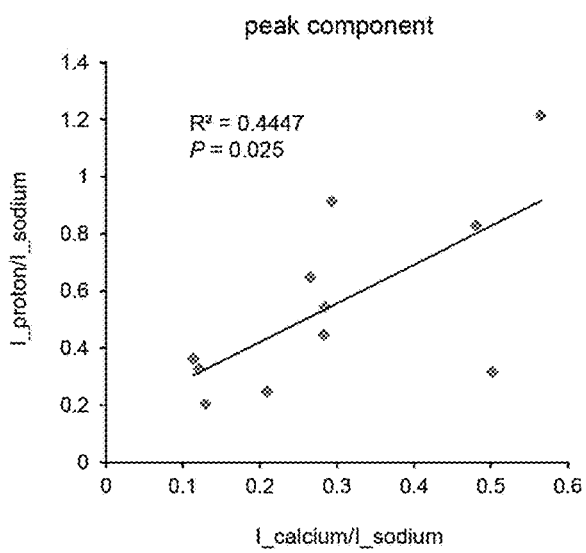
FIGS. 5A-D provide graphs showing correlation between calcium and proton selectivity in ChR2 mutants.
Figure 5B:
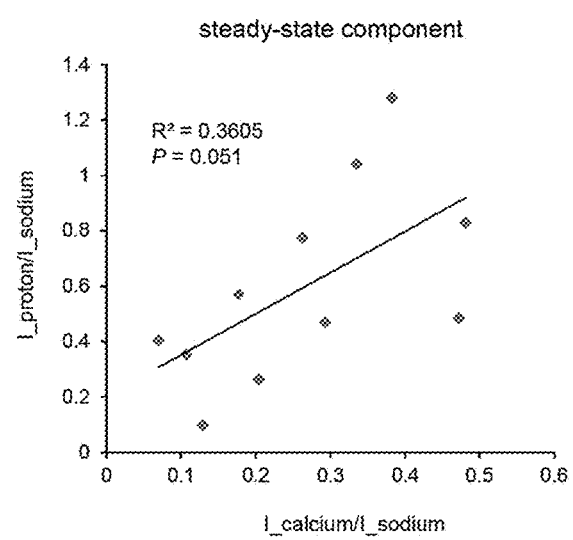

Ten mutants were characterized with either reduced calcium (seven mutants) or proton (five mutants) flux using whole cell patch clamp and ion-specific extracellular solutions, to measure ion-specific photocurrents, as previously done for small numbers of channelrhodopsin mutants [Ruffert, K., et al., Biochem Biophys Res Commun, 2011. 410(4):737-43; Kato, H. E., et al., Nature, 2012. 482(7385): 369-74; Kleinlogel, S., et al., Nat Neurosci, 2011. 14(4):5 13-8; Plazzo, A. P., et al., J Biol Chem, 2012. 287(7):4818-25; and Prigge, M., et al., J Biol Chem, 2012. 287(38): 31804-12; Schneider, F., D. et al., Biophys J, 2013. 105(1): 91-100]. Because ChR2 shows two apparent conducting states, exhibited by peak and steady-state components of its photocurrent [Nagel, G., et al., Proc Natl Acad Sci USA, 2003. 100(24):13940-5; Berndt, A., et al., Biophys J, 2010. 98(5):753-61; and Nikolic, K., et al., Photocycles of channelrhodopsin-2. Photochem Photobiol, 2009. 85(1): p. 400-11], the ion selectivity was characterized for both components. For completeness, in addition to obtaining raw photocurrents (FIGS. 6A-E), ion-specific reversal potentials were additionally characterized, although the interpretation of the reversal potentials in terms of calculated permeabilities may not be accurate due to the assumption of independent movement of multiple different ionic species in the Goldman-Hodgkin-Katz equation, which may not be met for channelrhodopsins [Berndt, A., et al., Biophys J, 2010. 98(5):753-61; Gradmann, D., et al. J Membr Biol, 2002. 189(2): p. 93-104; and Schneider, F., et al., Biophys J, 2013. 105(1): p. 91-100]. For the photocurrents: six of the seven calcium flux-reduced mutants identified in the imaging screen were found to have either reduced peak or steady-state calcium photocurrent ratios (compared to sodium) as measured in patch clamp (FIG. 2D), with mutants E90A and E90Q having the largest reductions of approximately 5-fold compared to wild-type; the seventh mutation, E123A, did not have a reduced calcium flux when examined in the patch clamp condition. Five out of five proton flux-reduced mutants identified in the imaging screen were similarly found to have reduced proton-to-sodium photocurrent ratios in patch clamp (normalized to sodium currents; FIG. 2E), with mutant I84L having the largest reduction of approximately 5-fold compared to wild-type. Interestingly, six out of the seven calcium flux-reduced mutants identified in the imaging screen had reduced proton-to-sodium photocurrent ratios, and four out of the five proton flux-reduced mutants identified in the imaging screen had reduced calcium-to-sodium photocurrent ratios. Indeed, the photocurrents of calcium and proton, normalized to sodium, appeared to be correlated to one another when regressed across the various point mutants ($r(9)=0.67$, $P<0.05$, Pearson's correlation coefficient, FIG. 4A; $r(9)=0.60$, $P<0.06$, Pearson's correlation coefficient, FIG. 5B). Thus, residues that alter ion selectivity for one ion may also alter ion selectivity for a second, independent, ion.

Combinatorial Mutagenesis Yields Highly Ion-Selective Channelrhodopsins.

Figure 3A:
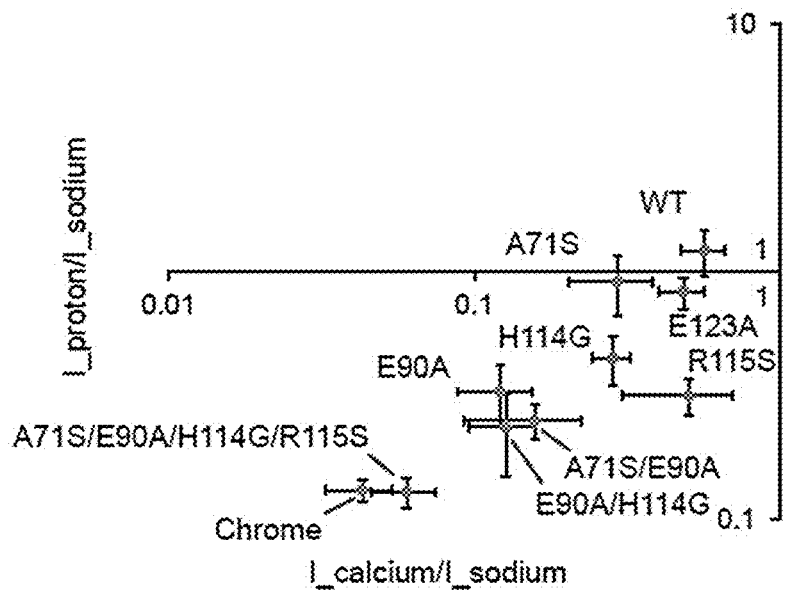
FIGS. 3A-H depict results of testing combinatorial mutations leading to multidimensional molecular optimization.
Figure 3B:
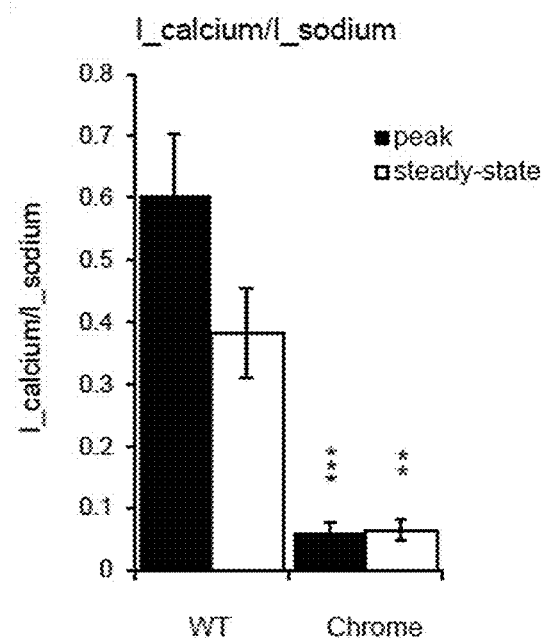
Figure 3C:
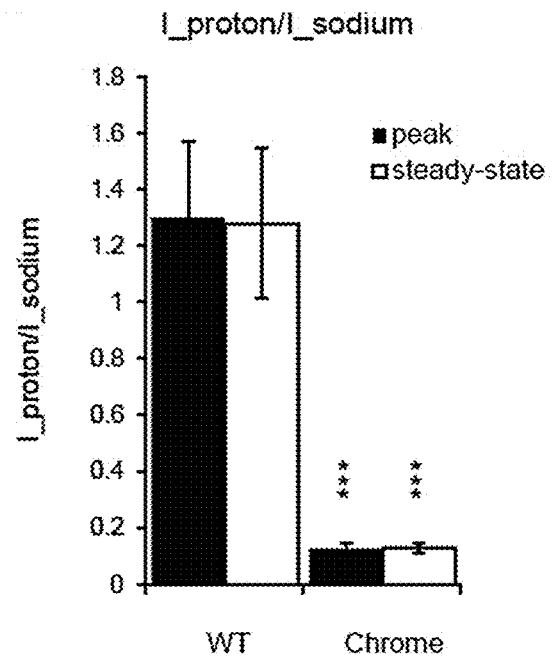
Figure 3D:
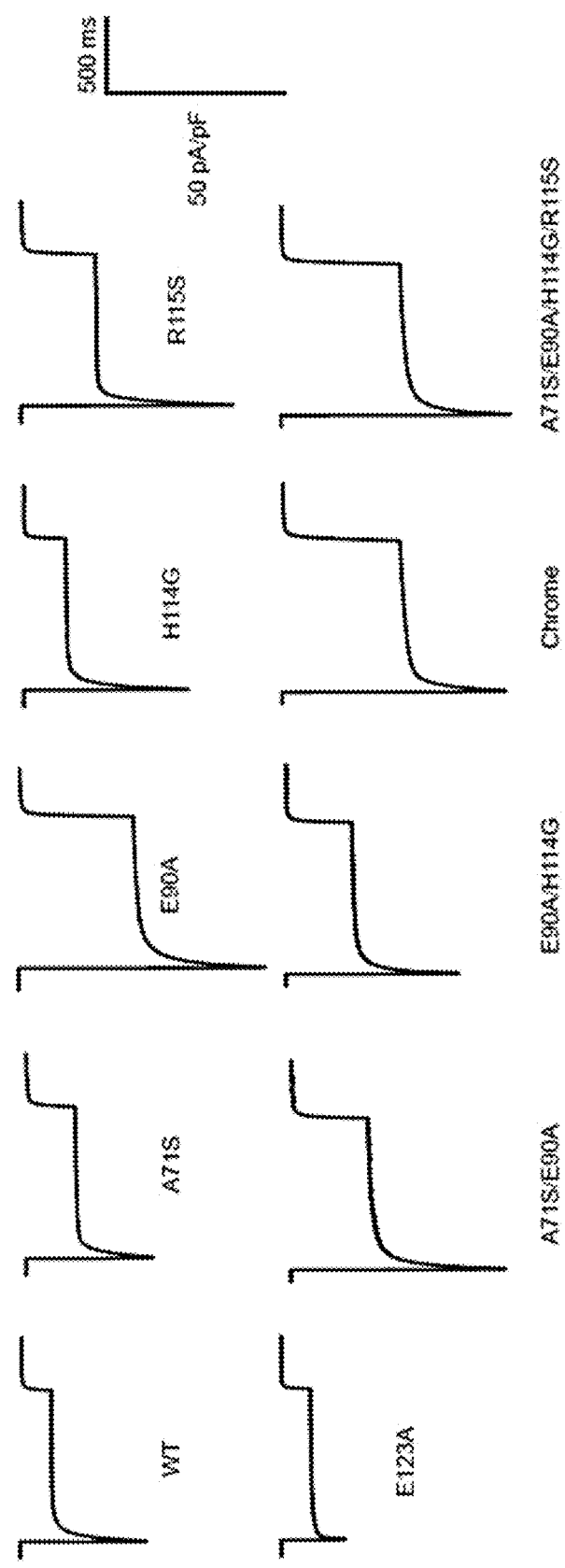
Figure 3E:
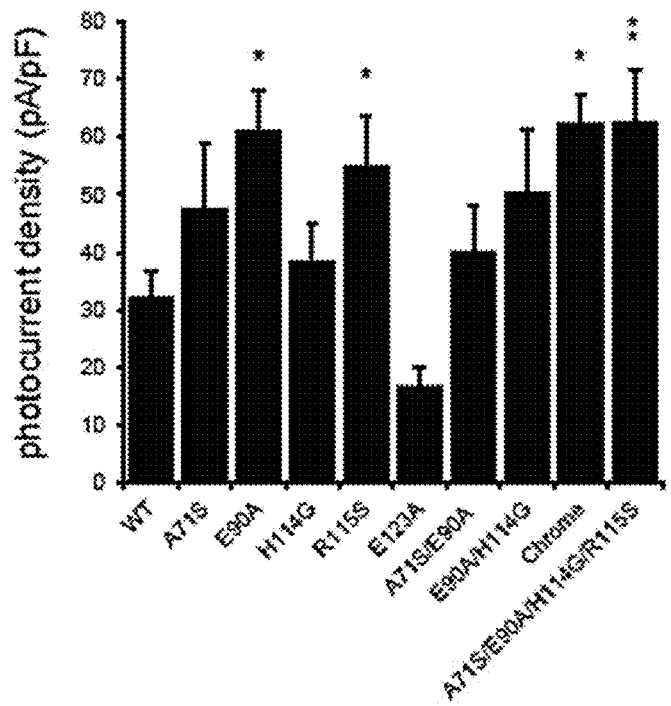
Figure 3F:
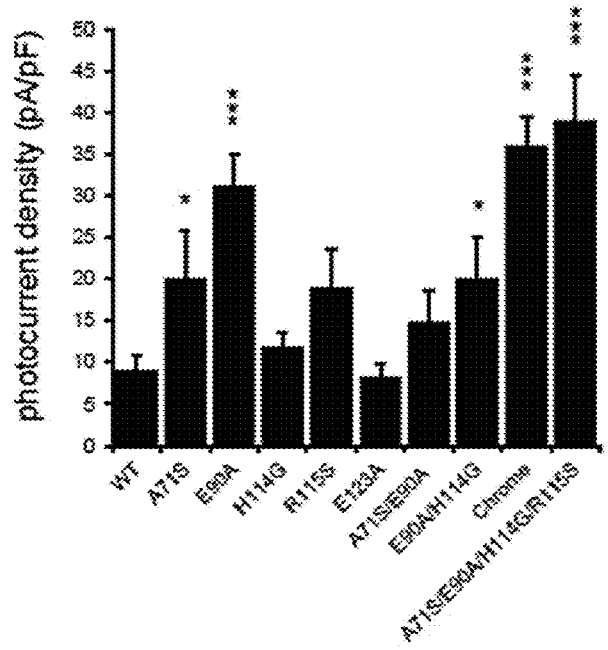
Figure 3G:
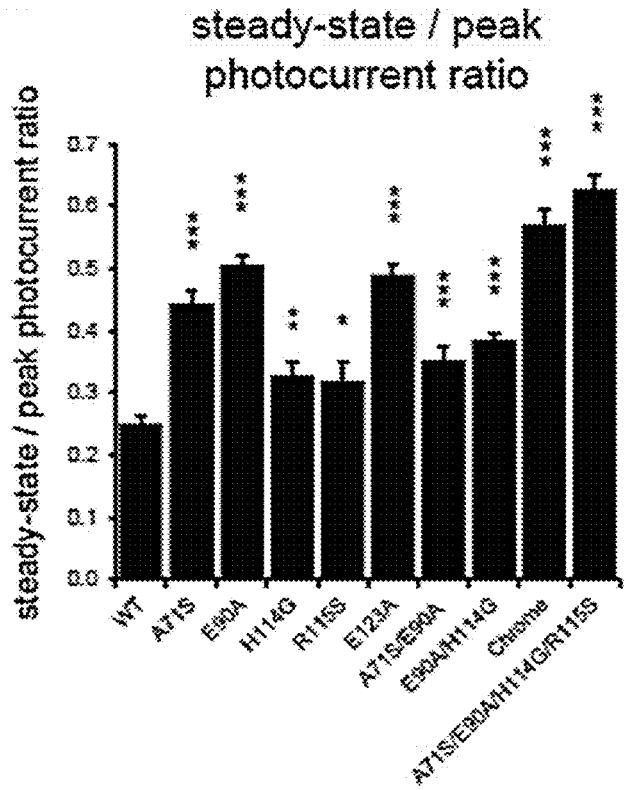
Figure 3H:
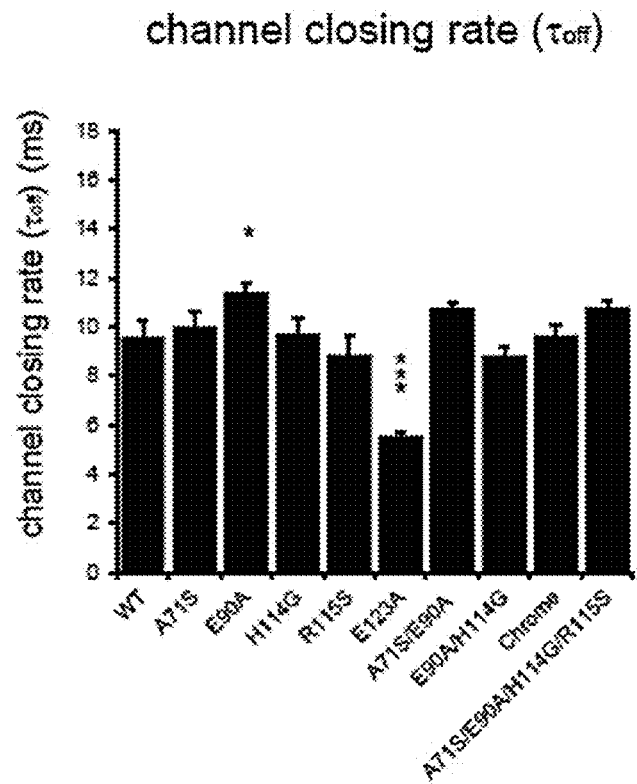
Figure 10A:
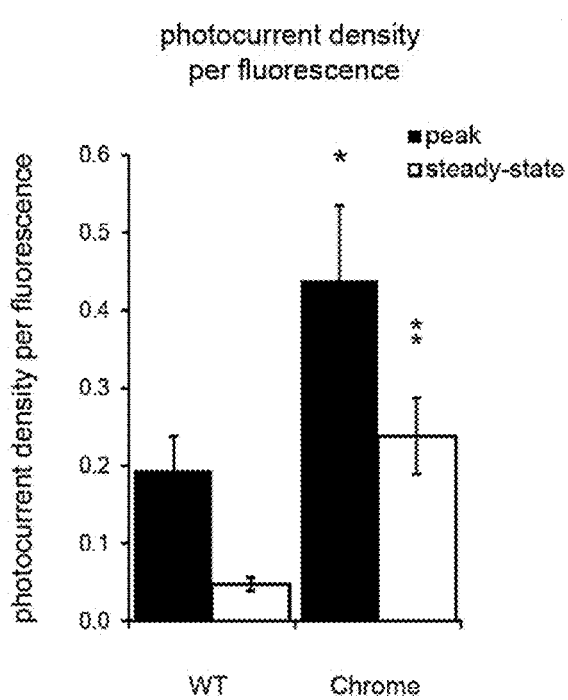
FIGS. 10A-C are graphs depicting the characterization of Chrome.
Figure 10B:
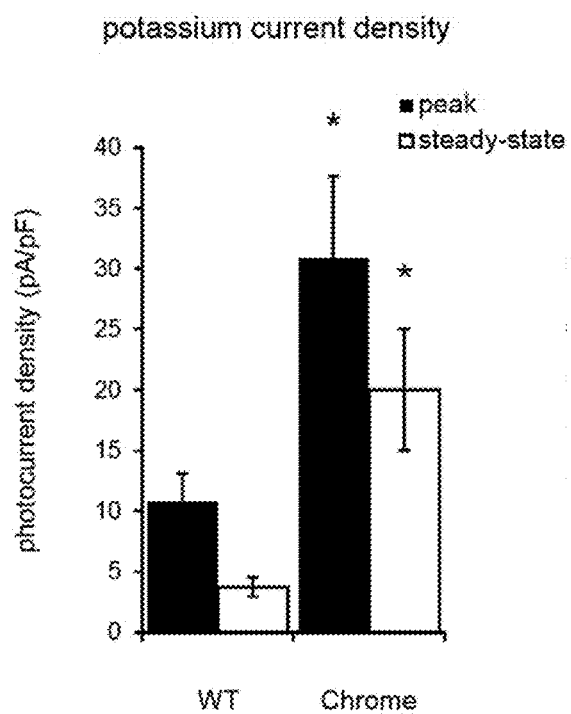
Figure 10C:
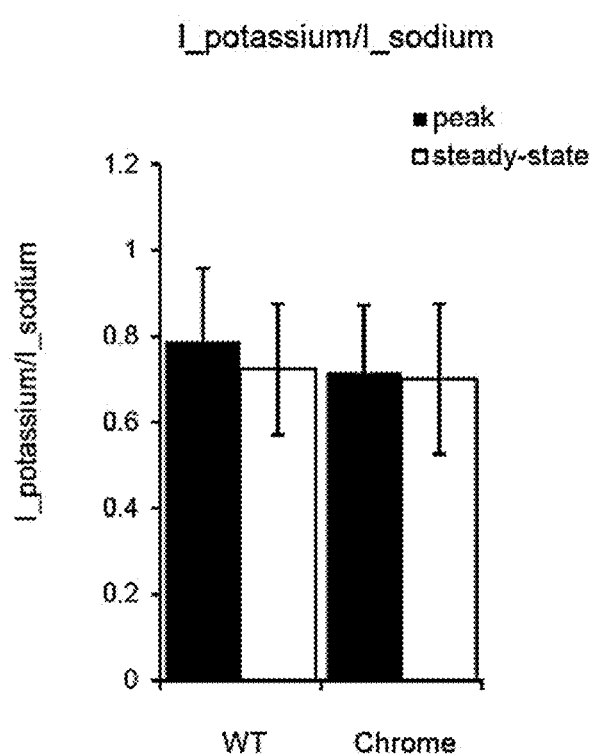

Multiple mutations identified in FIGS. 2D and 2E were combined to see whether ion selectivity could be further improved, i.e. whether the mutations might add synergistically. It was found through making double and triple mutants that the proton-to-sodium and calcium-to-sodium photocurrents could both be shifted down (FIG. 3A; raw photocurrents in FIGS. 7A-E), with the triple mutant A71S/E90A/H114G exhibiting calcium-to-sodium photocurrent ratio reduced 10-fold (n=7-10 HEK293FT cells, $P<0.001$, t-test comparing I_calcium/I_sodium to that of wild-type ChR2; FIG. 3B), and the proton-to-sodium photocurrent ratio reduced 10-fold (n=7 HEK293FT cells, $P<0.001$, t-test comparing I_calcium/I_sodium to that of wild-type ChR2; FIG. 3C). This mutant was named Chrome (Chr+ omitting certain ions). Thus, through this screening methodology, a new channelrhodopsin was created with order of magnitude improvement in its selectivity for two different ions, demonstrating the power of physiological screening. Because the ion selectivity screen was prefaced with a screen for improved photocurrent, Chrome also possessed an increased peak as well as steady-state (FIG. 3D-G) photocurrent density, and unchanged channel closing kinetics (FIG. 3H). Chrome had greater overall photocurrent when normalized to the fluorescence of a fluorophore fused to the C-terminus, a measure of expression level (FIG. 10A), suggesting but not proving an increased overall channel conductance. Chrome also had similar potassium selectivity, compared to sodium, vs. wild-type (FIGS. 10B-C).

FIGS. 3A-H depict combinatorial mutations leading to multidimensional molecular optimization. (FIG. 3A) Population data for proton-to-sodium photocurrent ratio vs. calcium-to-sodium photocurrent ratio of ChR2 mutants, measured using whole-cell patch clamp in HEK cells in ion-selective extracellular solutions (see Methods for details), using 470 nm, 1 s illumination, 10 mW/mm$^2$ irradiance (n=6-12 HEK293FT cells each). (FIGS. 3B-C) Population data for photocurrent density ratios measured using whole-cell patch clamp, for peak (filled bars) and steady-state (open bars) calcium photocurrent (I_calcium) divided by sodium photocurrent (I_sodium) (FIG. 3B), and peak (filled bars) and steady-state (open bars) proton photocurrent (I_proton) divided by sodium photocurrent (I_sodium) (FIG. 3C), of wild-type ChR2 and triple mutant A71S/E90A/H114G (n=7-10 HEK293FT cells each), a.k.a. Chrome, measured using the same illumination as in FIG. 3A. (FIG. 3D) Representative traces of photocurrent density, measured using whole-cell voltage clamp for the mutants in FIG. 3A, using the same illumination conditions. (FIGS. 3E-H) Population data for peak photocurrent density (FIG. 3E), steady-state photocurrent density (FIG. 3F), steady-state to peak photocurrent ratio (FIG. 3G) (measured using 470 nm, 1 s illumination, 10 mW/mm$^2$ irradiance), and channel closing rate $e$ (Toff) (FIG. 3H) (measured using 470 nm, 2 ms illumination, 10 mW/mm$^2$ irradiance), of mutants and mutant combinations in FIG. 3A (n=4-11 HEK293FT cells each).

Reversal Potential Measurements for ChR2 Mutants Characterized Using Patch Clamp.

Figure 4B:
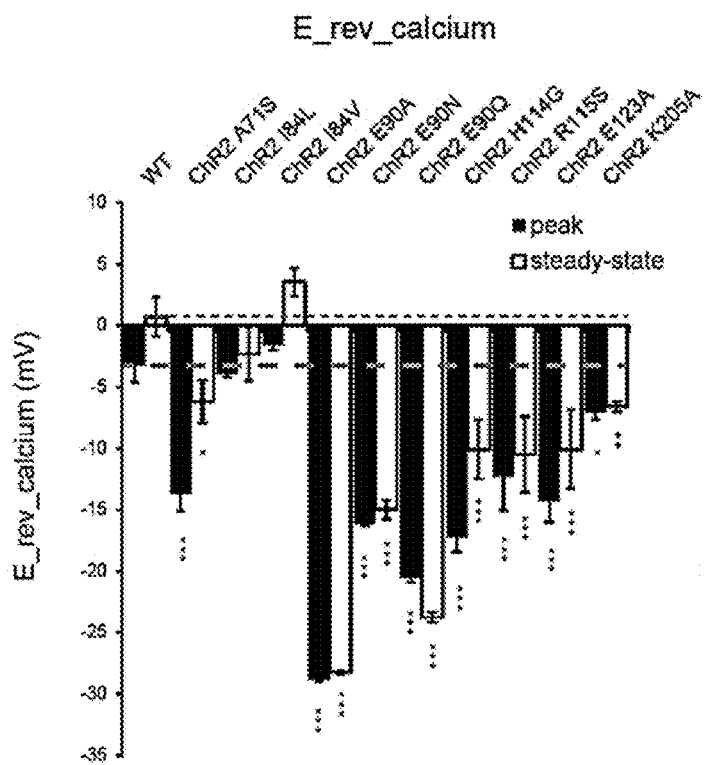
Figure 4C:
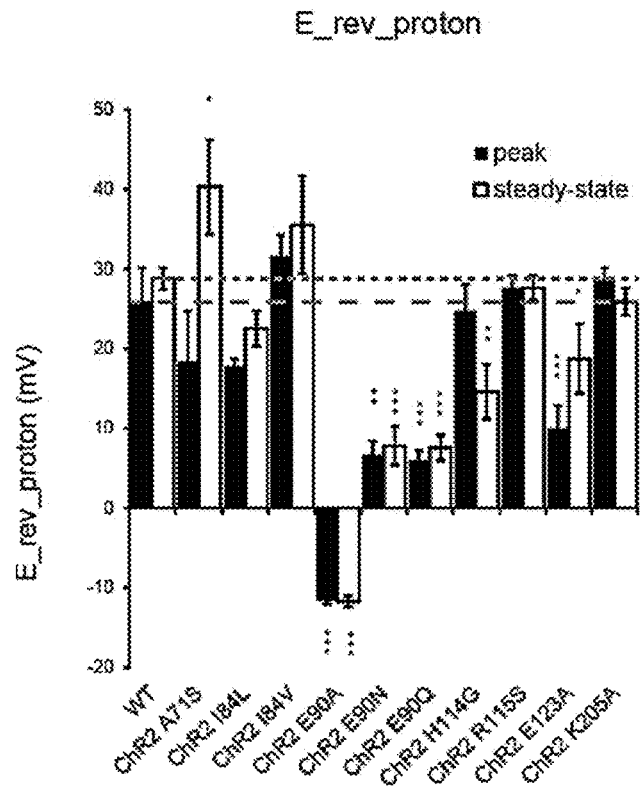
Figure 4D:
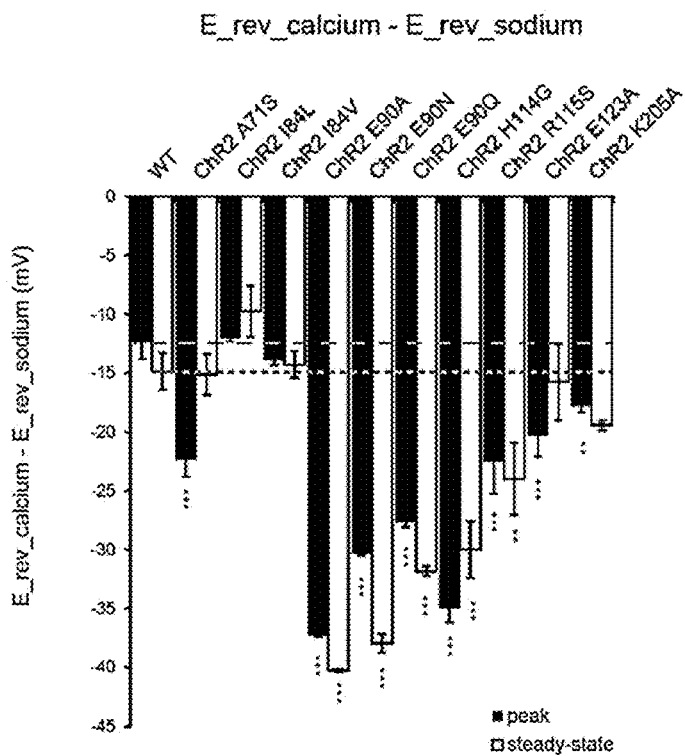
Figure 4E:
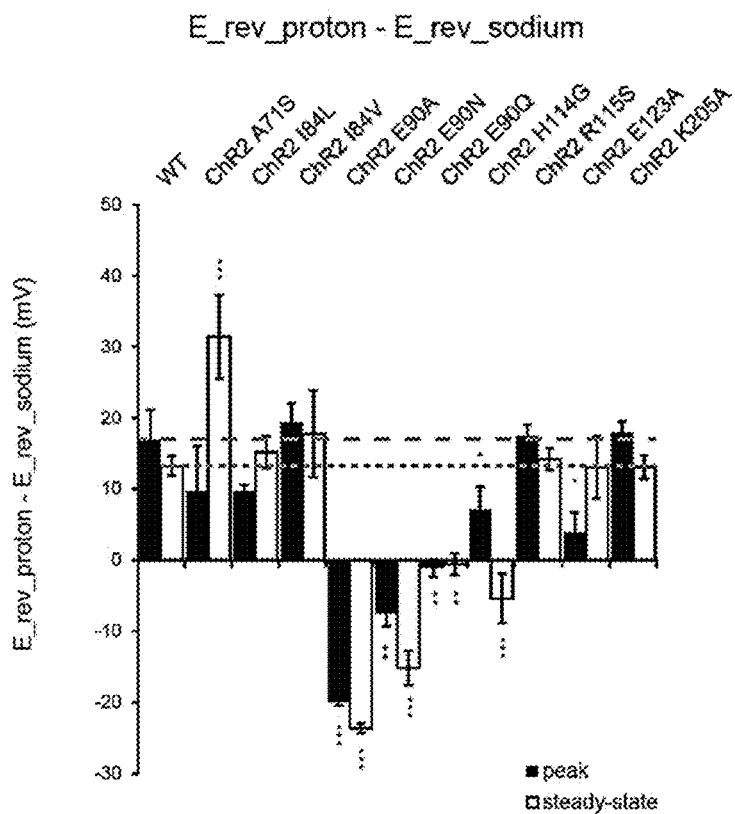
Figure 6A:
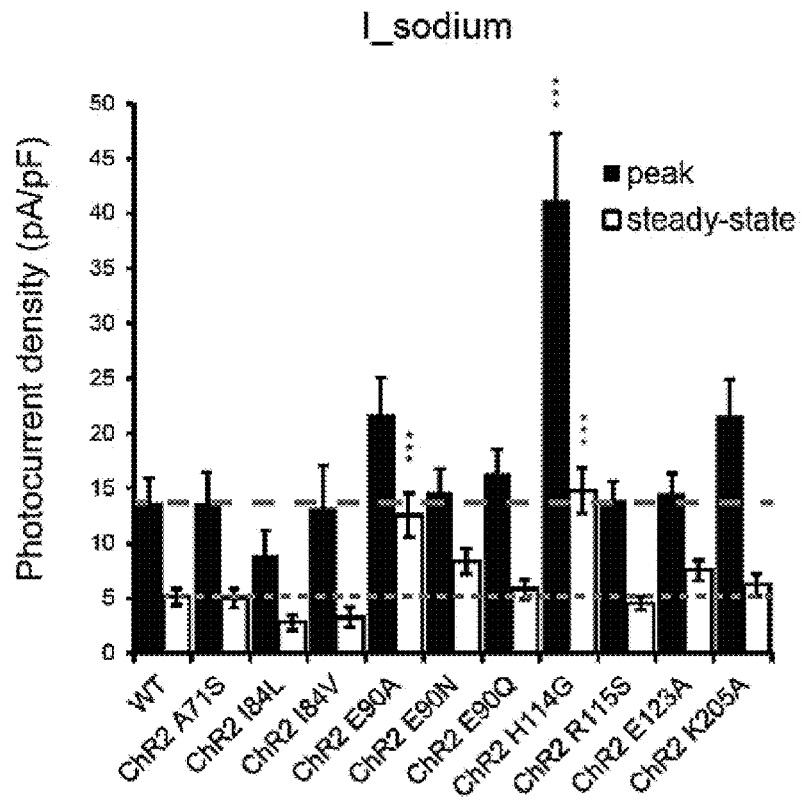
FIGS. 6A-C are graphs showing photocurrent density of ChR2 mutants in ion-selective solutions.

First, the reversal potentials of peak and steady-state components of the ten point mutants electrophysiologically characterized were measured, downstream of the calcium and proton selectivity stage (FIG. 2D, FIG. 2E) for sodium (FIG. 4A), calcium (FIG. 4B), and protons (FIG. 4C). The H114G mutant showed a positive shift in sodium reversal potential (FIG. 4A), consistent with the increase in sodium photocurrent for H114G (FIG. 6A). Many mutants identified in the screen had both decreases in calcium photocurrent (FIG. 6B) and decreases in calcium reversal potential (FIG. 4B). A similar trend held for protons (FIG. 6B; FIG. 4B). A measure of relative selectivity, calcium reversal potential minus that of sodium (FIG. 4D), was calculated and found statistically significant shifts of this value ranging from −10 mV to −25 mV relative to wild-type for most of the mutants. Similarly, half of the mutants had downward shifts in proton reversal potential minus sodium reversal potential (FIG. 4E). The differences between photocurrent measurements (FIG. 2D, FIG. 2E) and reversal potential measurements may be explained by the fact that calcium- and proton-binding sites, as well as potential interactions between multiple ions, may differentially affect photocurrents driven from baseline vs. reversal potential [see Lin, J. Y., et al., Biophys J, 2009. 96(5):1803-14; Nagel, G., et al., Proc Natl Acad Sci USA, 2003. 100(24):13940-5; Gradmann, D., et al. J Membr Biol, 2002. 189(2):93-104; Chow, B. Y., et al., Nature, 2010. 463(7277):98-102; Gradmann, D., et al., Biophys J, 2011. 101(5):1057-68; Eisenman, G. & J. A. Dani, Annu Rev Biophys Biophys Chem, 1987. 16:205-26; and Hess, P., et al., J Gen Physiol, 1986. 88(3):293-3 19], and discussion below about complications using the Goldman-Hodgkin-Katz equation to interpret reversal potentials).

FIGS. 4A-E depict reversal potential measurements for ChR2 mutants with improved ion selectivity. (FIGS. 4A-C) Population data for reversal potentials, measured using whole-cell patch clamp in HEK cells in ion-specific extracellular solutions (see Methods for details), with peak (filled bars) and steady-state (open bars) reversal potentials, for wild-type ChR2 and the 10 ion selectivity mutants shown in FIGS. 2D-E (n=3-6 HEK293FT cells each), for: sodium (E_rev_sodium) measured in 145 mM NaCl, pH 7.4 (FIG. 4A), calcium (E_rev_calcium) measured in 90 mM CaCl2, pH 7.4 (FIG. 4B), and proton (E_rev_proton) measured in 135 mM NMDG, pH 6.4 (FIG. 4C). (FIGS. 4D-E) Population data for peak (filled bars) and steady-state (open bars) reversal potentials, relative to sodium reversal (n=3-6 HEK293FT cells each), for: calcium (E_rev_calcium−E_rev_sodium) (FIG. 4D), and proton (E_rev_proton−E_rev_sodium) (FIG. 4E).

Correlated Effects of Mutations on Calcium and Proton Permeability as Determined by Reversal Potential Measurements.

Figure 5C:
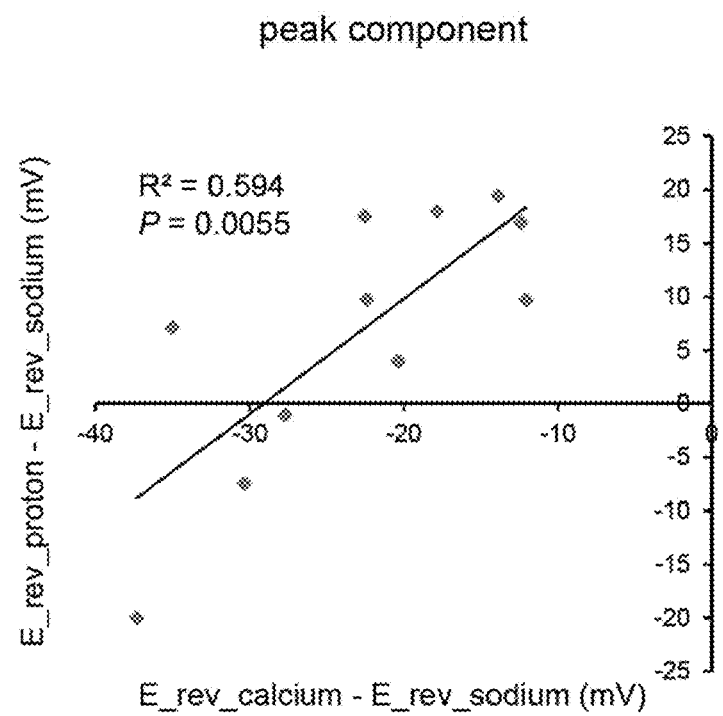
Figure 5D:
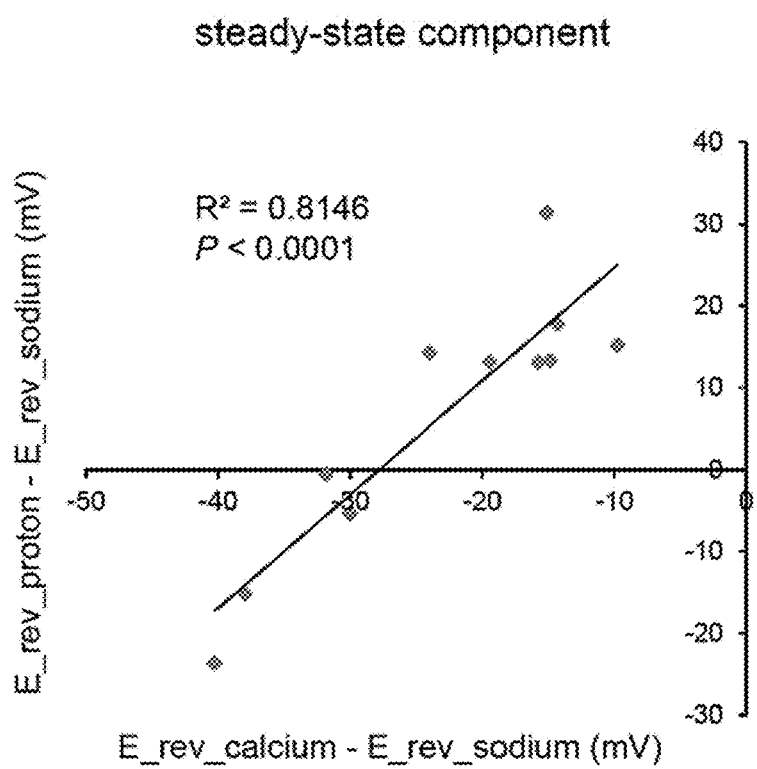

As noted elsewhere herein, there is a correlation between the photocurrents of calcium vs. proton (each divided by that of sodium) (FIGS. 5A-B) for the 10 point mutants electrophysiologically characterized, downstream of the calcium and proton selectivity stage. A significant correlation was also noted in reversal potential measurements for calcium vs. proton (each subtracting off that of sodium) for both peak ($r(9)=0.77$, $P<0.01$, Pearson's correlation coefficient; FIG. 5C) and steady-state ($r(9)=0.90$, $P<0.001$, Pearson's correlation coefficient, FIG. 5D) components.

FIGS. 5A-D depict correlation between calcium and proton selectivity in ChR2 mutants. (FIGS. 5A, 5B) I_proton/I_sodium vs. I_calcium/I_sodium for both peak (FIG. 5A) and steady-state (FIG. 5B) photocurrents, for wild-type ChR2 and 10 mutants with improved ion selectivity shown in FIG. 2D, e (n=5-12 HEK293FT cells each). (FIGS. 5C, 5D) E_rev_proton–E_rev_sodium vs. E_rev_calcium–E_rev_sodium, for both peak (FIG. 5C) and steady-state (FIG. 5D) photocurrents, for wild-type ChR2 and the 10 mutants in FIGS. 5A and 5B. Lines are linear regression fits.

Figure 6B:
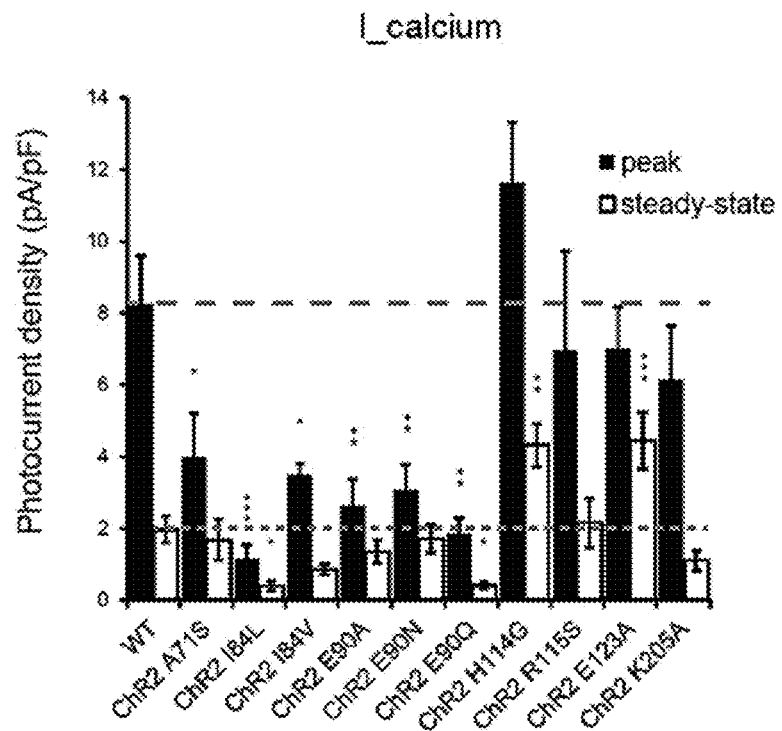
Figure 6C:
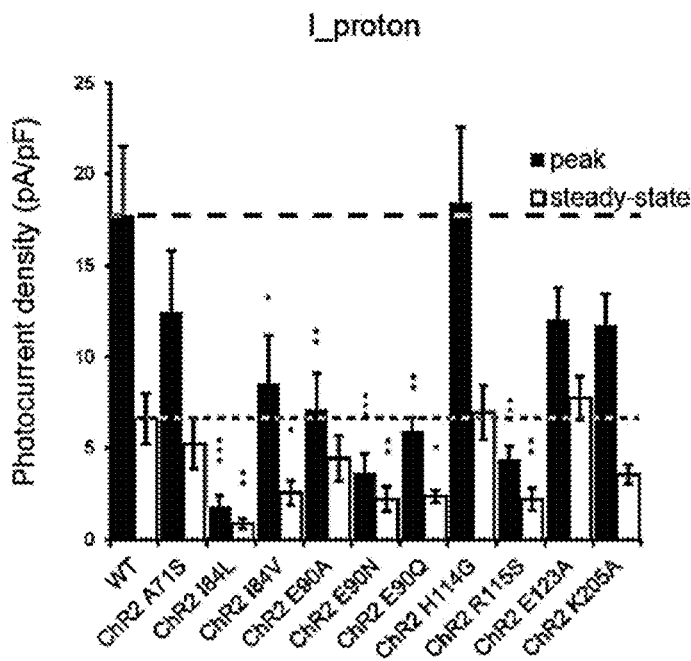

FIGS. 6A-C depict photocurrent density of ChR2 mutants in ion-selective solutions. (FIGS. 6A-C) Population data for peak (filled bars) and steady-state (open bars) photocurrent densities, measured using whole-cell patch clamp in HEK cells in ion-specific extracellular solutions, for wild-type ChR2 and 10 mutants with improved ion selectivity shown in FIGS. 2D, 2E (n=5-12 HEK293FT cells each), for: sodium (I_sodium) measured in 145 mM NaCl, pH 7.4 (FIG. 6A), calcium (I_calcium) measured in 90 mM CaCl$_2$, pH 7.4 (FIG. 6B), and proton (I_proton) measured in 135 mM NMDG, pH 6.4 (FIG. 6C).

Figure 7A:
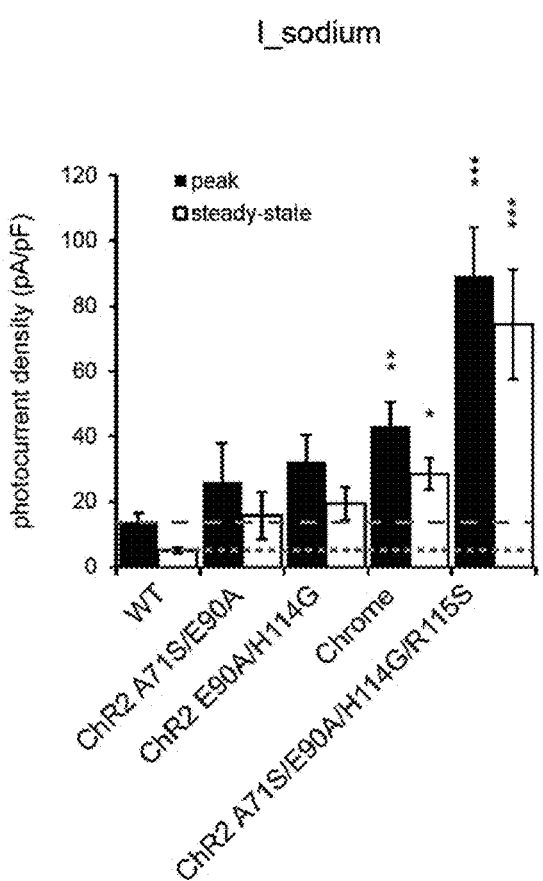
FIGS. 7A-E are graphs showing ion selectivity of ChR2 mutant combinations assessed using photocurrent ratios.
Figure 7B:
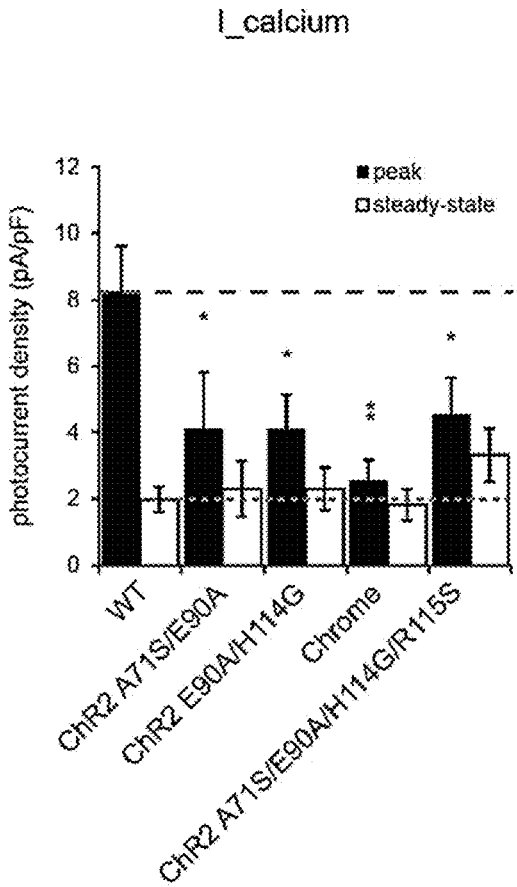
Figure 7C:
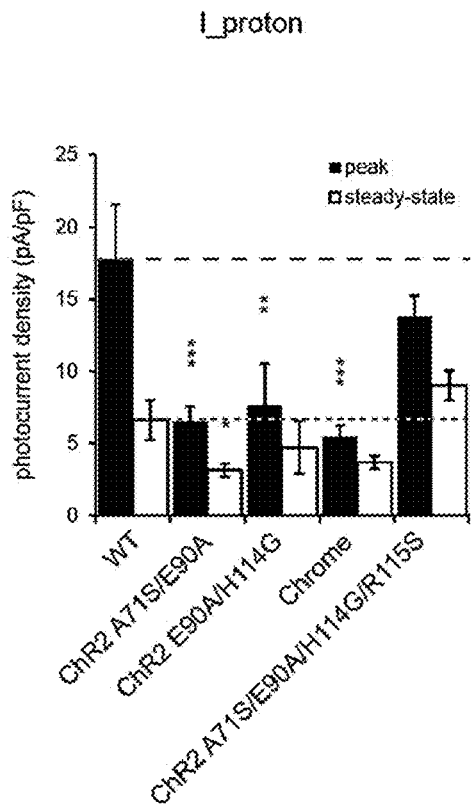
Figure 7D:
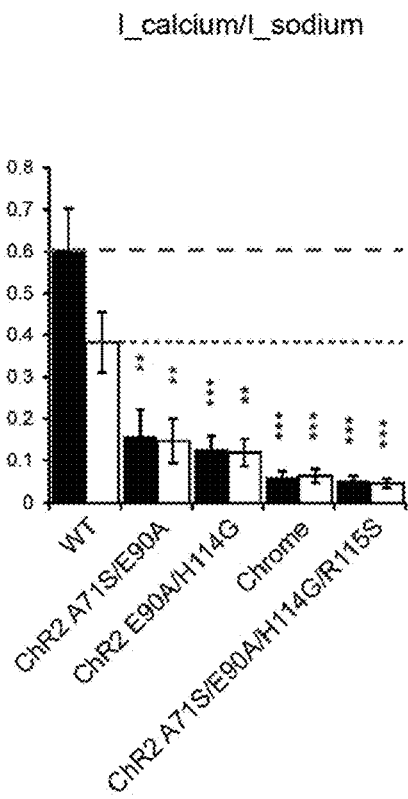
Figure 7E:
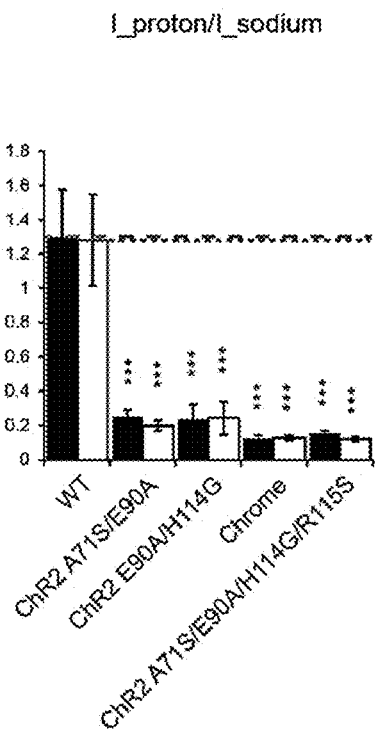

FIGS. 7A-E depict ion selectivity of ChR2 mutant combinations assessed using photocurrent ratios. (FIGS. 7A-C) Population data for peak (filled bars) and steady-state (open bars) photocurrent densities, measured using whole-cell patch clamp in HEK cells in ion-specific extracellular solutions, for wild-type ChR2 and mutant combinations shown in FIG. 3A (n=4-12 HEK293FT cells each), for: sodium (I_sodium) measured in 145 mM NaCl, pH 7.4 (FIG. 7A), calcium (I_calcium) measured in 90 mM CaCl2, pH 7.4 (FIG. 7B), and proton (I_proton) measured in 135 mM NMDG, pH 6.4 (FIG. 7C). (FIGS. 7D-E) Population data for peak (filled bars) and steady-state (open bars) photocurrent density ratios, measured using whole-cell patch clamp in HEK cells in ion-specific extracellular solutions, for wild-type ChR2 and mutant combinations shown in FIGS. 7A-C (n=4-12 HEK293FT cells each), for: calcium photocurrent (I_calcium) divided by sodium photocurrent (I_sodium) (FIG. 7D), and proton photocurrent (I_proton) divided by sodium photocurrent (I_sodium) (FIG. 7E).

Reversal Potential Measurements for ChR2 Mutant Combinations.

Figure 8A:
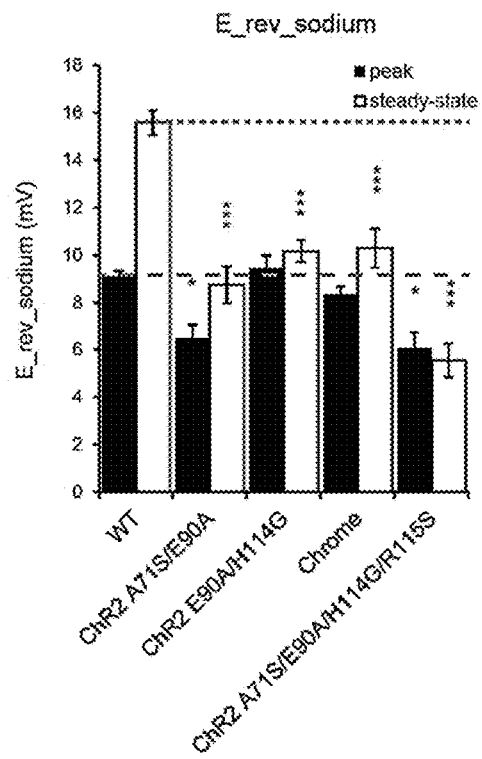
FIGS. 8A-E are graphs depicting reversal potential measurements for ChR2 mutant combinations.
Figure 8B:
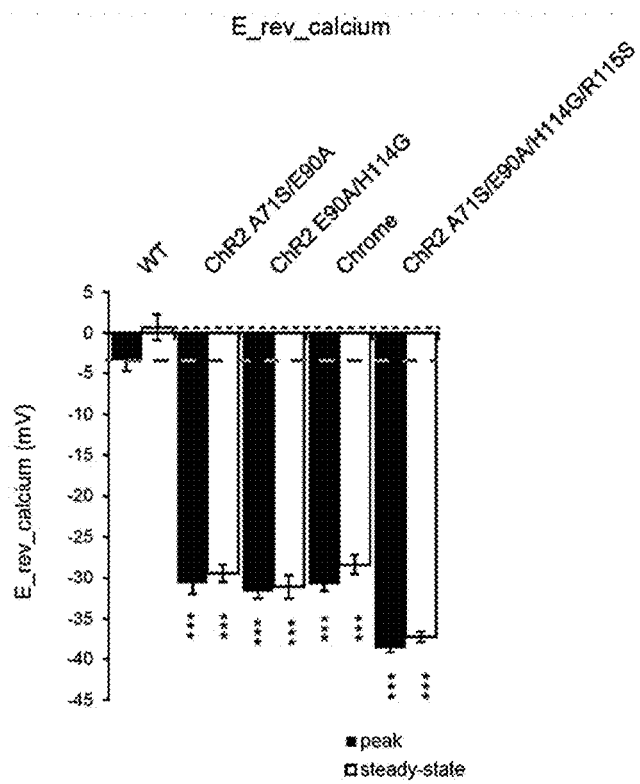
Figure 8C:
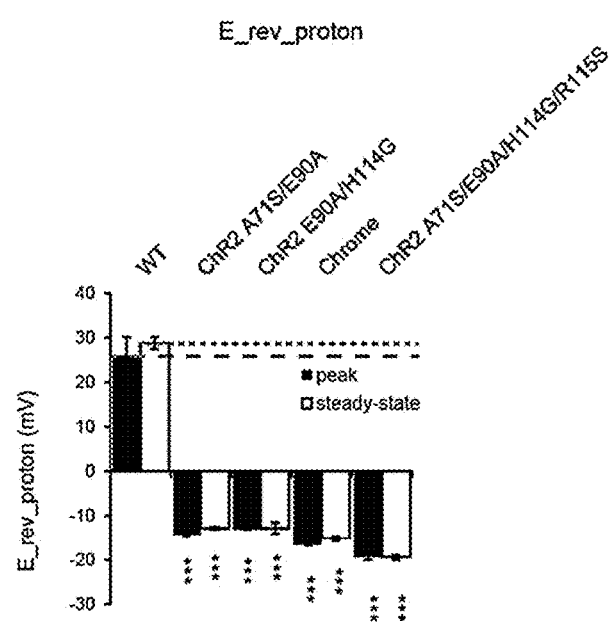
Figure 8D:
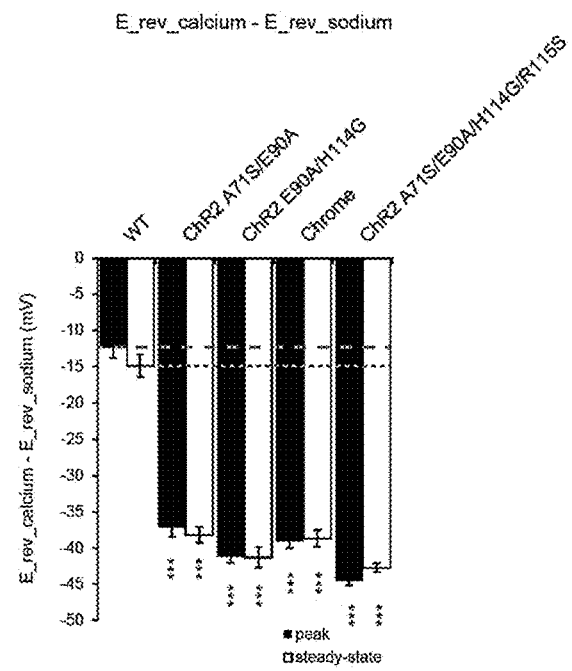
Figure 8E:
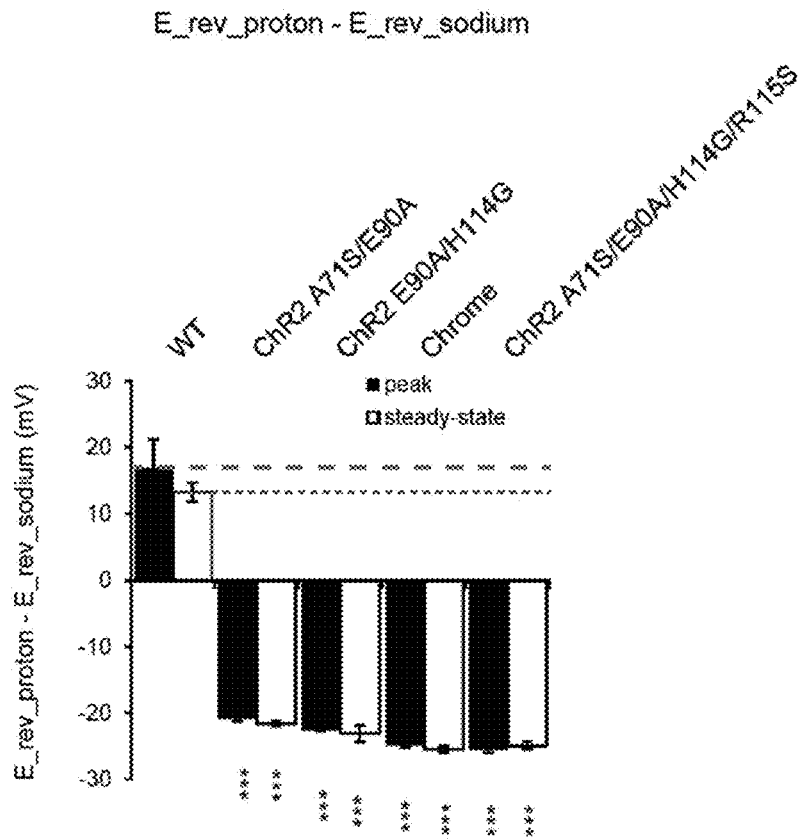

Reversal potentials of ChR2 mutant combinations (double mutants A71S/E90A, E90A/H114G, Chrome, and quadruple mutant A71S/E90A/H114G/R115S) were measured for sodium (FIG. 8A), calcium (FIG. 8B), and protons (FIG. 8C), obtaining strong shifts in calcium and proton for all of the mutants assessed, for both the peak and steady state components, and ~35 mV shifts in calcium reversal potential and ~45 my shifts in proton reversal potential for the quadruple mutant. When relative selectivity, calcium reversal potential minus that of sodium (FIG. 8D) and proton reversal potential minus that of sodium (FIG. 8E) were compared, strong shifts again were again observed. FIGS. 8A-E depict reversal potential measurements for ChR2 mutant combinations. (FIGS. 8A-C) Population data for peak (filled bars) and steady-state (open bars) reversal potentials, measured using whole-cell patch clamp in HEK cells in ion-specific extracellular solutions (see Methods for details), for wild-type ChR2 and mutant combinations shown in FIG. 3A (n=4-8 HEK293FT cells each), for: sodium (E_rev_sodium) measured in 145 mM NaCl, pH 7.4 (FIG. 8A), calcium (E_rev_calcium) measured in 90 mM CaCl$_2$, pH 7.4 (FIG. 8B), and proton (E_rev_proton) measured in 135 mM NMDG, pH 6.4 (FIG. 8C). (FIGS. 8D-E) Population data for peak (filled bars) and steady-state (open bars) reversal potentials, relative to sodium reversal, for ChR2 mutant combinations shown in FIGS. 8A-C (n=4-8 HEK293FT cells each), for: calcium (E_rev_calcium–E_rev_sodium) (FIG. 8D), and proton (E_rev_proton–E_rev_sodium) (FIG. 8E).

Permeability Ratios Estimated from Reversal Potential Measurements.

Channels that transport multiple kinds of ion, and that might possess multiple binding sites, are biophysically complex to model [Gradmann, D., et al., Biophys J, 2011. 101(5):1057-68; Eisenman, G. & J. A. Dani, Annu Rev Biophys Biophys Chem, 1987. 16:205-26; and Hess, P., et al., J Gen Physiol, 1986. 88(3):293-3 19]. Channelrhodopsins may potentially possess such properties [Kato, H. E., et al., Nature, 2012. 482(7385):369-74; Lin, J. Y., et al., Biophys J, 2009. 96(5):1803-14; Nagel, G., et al., Proc Natl Acad Sci USA, 2003. 100(24):13940-5; Gradmann, D., et al., J Membr Biol, 2002. 189(2):93-104; and Chow, B. Y., et al., Nature, 2010. 463(7277):98-102], with four different native ionic species capable of passing through, and the potentiality of one or more binding sites for one or more ions. Accordingly, the focus was placed on analyzing both peak as well as steady-state ion specific photocurrents (FIGS. 2D, 2E), in order to capture real-world performance of the mutants. Other papers have attempted to estimate channelrhodopsin ion permeabilities using the Goldman-Hodgkin-Katz (GHK) equation [Prigge, M., et al., J Biol Chem, 2012. 287(38):31804-12], but there has been controversy about whether the GHK can be used, even in modified form [Lin, J. Y., et al., Biophys J, 2009. 96(5):1803-14], since the assumption of independent movement of different ionic species in the GHK equation may not hold true for channelrhodopsins, potentially due to the complexities discussed above [Nagel, G., et al., Proc Natl Acad Sci USA, 2003. 100(24):13940-5; Gradmann, D., et al., J Membr Biol, 2002. 189(2):93-104; and Chow, B. Y., et al., Nature, 2010. 463(7277):98-102]. Complicating matters further is the fact that no single channel conductances have been measured for any channelrhodopsin, due to their small values, meaning that many key parameters are not known. Thus, ion permeabilities are estimated as in Lin, J. Y., et al., Biophys J, 2009. 96(5):1803-1421 for completeness, with the acknowledgment that while they reflect one potential interpretation of the reversal potential measurements, they may only provide a rough estimate, which is denoted P* in FIGS. 9A-B. The wild-type ChR2 has permeability ratio of calcium vs. sodium of ~0.20, and of proton vs. sodium of ~690,000. The estimated permeability ratios for the 10 point mutants electrophysiologically characterized, downstream of the calcium and proton selectivity stage, as well as the combinatorial mutations, were generally lower than that of the wild-type, and for the combinatorial mutants, greatly lower—the quadruple mutant, for example, had a permeability ratio of calcium vs. sodium of 0.048 and a permeability ratio of proton vs. sodium of 91,000. Thus, while acknowledging that these are estimates, the results are consistent with the photocurrent data obtained.

Figure 9A:
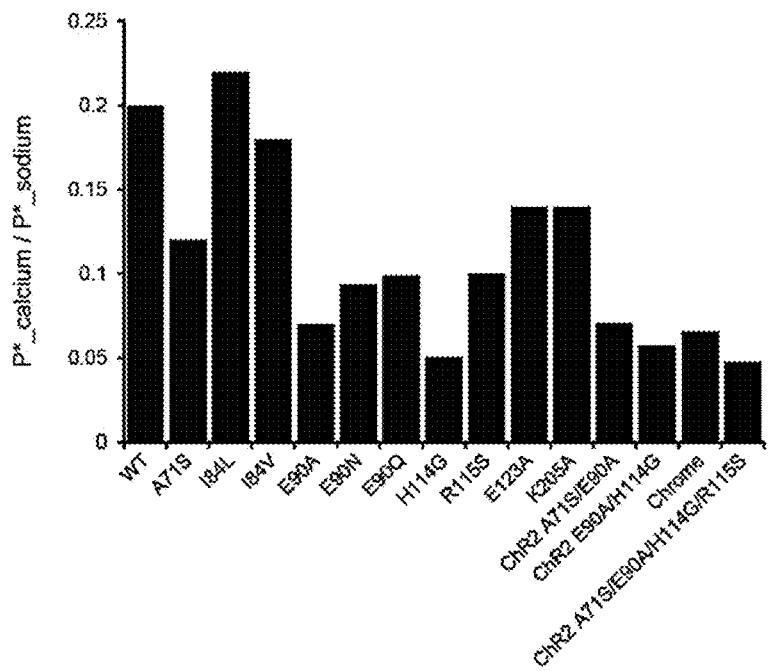
FIGS. 9A and 9B are graphs depicting permeability ratios estimated from reversal potential measurements.
Figure 9B:
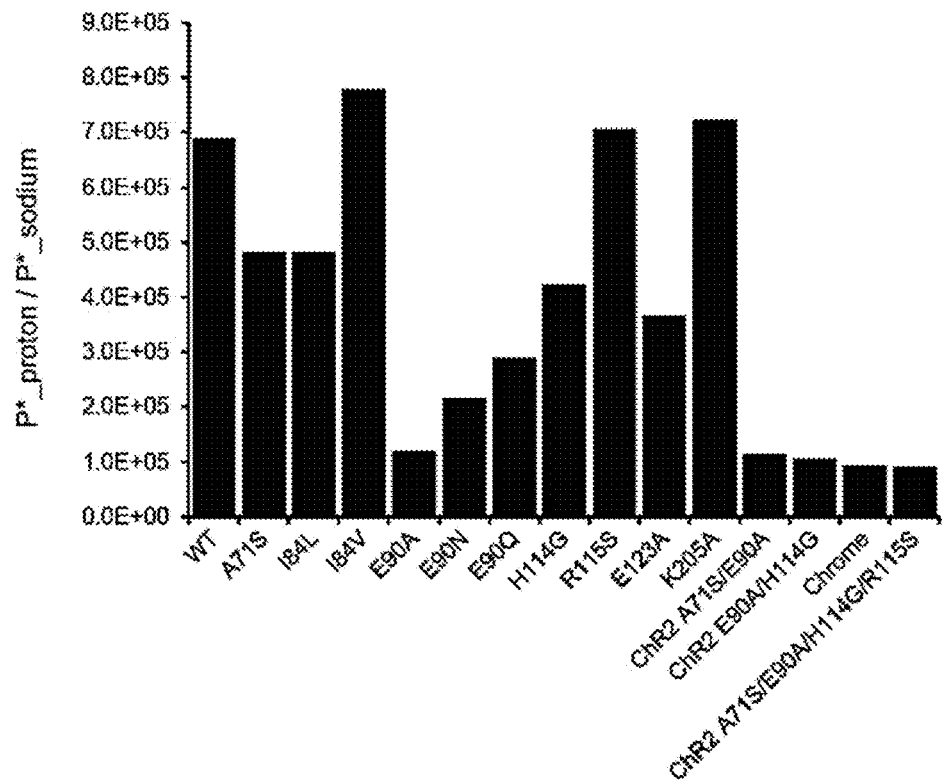

FIGS. 9A-B depict permeability ratios estimated from reversal potential measurements. (FIGS. 9A-B) Estimated permeability ratios, calculated using a modified Goldman-Hodgkin-Katz equation, between calcium and -sodium ($P^*\_calcium/P^*\_sodium$) (FIG. 9A), and between protons and sodium ($P^*\_proton/P^*\_sodium$) (FIG. 9B), for ChR2, and mutants thereof.

Additional Characterization of Chrome.

When the photocurrent of Chrome in Tyrode's solution divided by the total fluorescence of the channelrhodopsin expression levels was compared to wild-type ChR2, there was a 2-fold increase for the peak component (n=6-10 HEK293FT cells, P<0.05 t-test comparing peak photocurrent density divided by the total fluorescence to that of wild-type ChR2; FIG. 10A) and 5-fold increase in the steady-state component (n=6-10 HEK293FT cells, P<0.01 t-test comparing peak photocurrent density divided by the total fluorescence to that of wild-type ChR2; FIG. 10A). Although this measure may reflect other factors such as improved membrane trafficking and folding efficiencies, it suggests that the estimated conductance of Chrome may be significantly higher that the wild-type ChR2.

In addition, when the potassium photocurrent was measured (FIG. 10B), the potassium-to-sodium photocurrent ratio of Chrome was not significantly changed compared to wild-type ChR2, suggesting that the selectivity for potassium over sodium was not significantly altered (n=6 HEK293FT cells, P>0.8 t-test comparing I_potassium/I_sodium to that of wild-type ChR2; FIG. 10C).

FIGS. 10A-C depict the characterization of Chrome. (FIG. 10A) Population data for peak (filled bars) and steady-state (open bars) photocurrent density measured in Tyrode's solution divided by the total fluorescence of each cell, of wild-type ChR2 and Chrome using 470 nm, is illumination, 10 mW/mm$^2$ irradiance (n=6-10 HEK293FT cells each). (FIGS. 10B-C) Population data for peak (filled bars) and steady-state (open bars) potassium photocurrent properties measured using illumination conditions as in (a), including density measured in 145 mM KCl, pH 7.4 (FIG. 10B), as well as peak (filled bars) and steady-state (open bars) potassium photocurrent (I_potassium) divided by sodium photocurrent (I_sodium) (FIG. 10C), of wild-type ChR2 and Chrome (n=6 HEK293FT cells each).

Advantages and Improvements Over Existing Technologies, Methods, Devices or Materials and Commercial Applications.

Mutants were identified of the light-gated cation channel channelrhodopsin-2, here named Chrome and ChromeQ, with order-of-magnitude reduction in calcium and proton photocurrents, compared to wild-type, while preserving overall photocurrent amplitude and kinetics. Given the many roles that calcium ions and protons play in metabolism, cell signaling, gene expression, transmitter release, receptor trafficking, and so forth, Chrome and ChromeQ may be of interest for a variety of experimental paradigms in the biosciences. Given clinical interest in optogenetic tools as part of novel prototyped optical neural control prosthetics and implants [Chow, B. Y. & Boyden, E. S. (2013) Optogenetics and Translational Medicine, Science Translational Medicine 5(177):177ps5], reducing calcium and proton conductances may make for tools with fewer side effects over long durations of use. In addition, insights were discovered into how microbial opsin protein engineering can take place. For example, it was found that mutants that improve photocurrent are distributed throughout significant fractions of the opsin, including practically all transmembrane and extracellular or intracellular loop regions, in contrast to previous studies that have focused on key subdomains of the protein highlighted by homology or structure. In addition, it was found that mutants that improve ion conductance can have additive and synergistic effects upon combination.

Mutations identified and disclosed herein may be used to alter the ion selectivity of other channelrhodopsins, such as Chronos, Chrimson, ChIEF, C1V1, and ReaChR. For example, mutations listed in Table 1 may be applied at homologous amino acid positions in other channelrhodopsins (e.g. Chronos, Chrimson, ChIEF, C1V1, and ReaChR) to alter their ion selectivity.

Earlier reports had identified several point mutations that alter ion-specific photocurrents [Ruffert, K., et al., Biochem Biophys Res Commun, 2011. 410(4):737-43; Kato, H. E., et al., Nature, 2012. 482(7385):369-74; Kleinlogel, S., et al., Nat Neurosci, 2011. 14(4):5 13-8; Plazzo, A. P., et al., J Biol Chem, 2012. 287(7):4818-25; and Eisenhauer, K., et al., J Biol Chem, 2012. 287(9):6904-11], finding mutations that alter ion photocurrents typically by 2-fold to 4-fold. It is hard to quantitatively compare results from these different earlier studies to one another, due to differences in method of assessing ion selectivity (photocurrent ratio vs. reversal potential and peak vs. steady-state component), experimental conditions (ion composition, pH, types of cells used), and also the fact that they often used different channelrhodopsin backbones to explore their respective mutations (and mutations in one channelrhodopsin may not have the same effect in other ones). However, the present study was able to confirm several earlier discoveries, even as it expanded greatly the number of mutants known to alter ion selectivity. For example, several earlier reports have shown that mutations in channelrhodopsin residue E90 alter proton selectivity [Ruffert, K., et al., Biochem Biophys Res Commun, 2011. 410(4):737-43; Kato, H. E., et al., Nature, 2012. 482(7385):369-74; and Eisenhauer, K., et al., J Biol Chem, 2012. 287(9):6904-11], as found in the present study as well. Thus, the screening method not only allows for elucidation of new mutants that affect microbial opsin performance, and the discovery of potential principles of optogenetic protein engineering, but allows for systematic comparison of many mutants in similar and controlled conditions.

EQUIVALENTS

It is to be understood that the methods, molecules, and compositions that have been described above are merely illustrative applications of the principles of the invention. Numerous modifications may be made by those skilled in the art without departing from the scope of the invention.

Although the invention has been described in detail for the purpose of illustration, it is understood that such detail is solely for that purpose and variations can be made by those skilled in the art without departing from the spirit and scope of the invention which is defined by the following claims.

The contents of all literature references, publications, patents, and published patent applications cited throughout this application are incorporated herein by reference in their entirety.

We claim:

1. A light-activated ion channel polypeptide comprising an amino acid sequence set forth as (i) SEQ ID NO: 11 or (ii) the amino acid sequence of SEQ ID NO: 11 with one or more amino acid modifications wherein the amino acids corresponding to positions S71, A90, and G114 of SEQ ID NO: 11 are not modified, and having at least 98% amino acid sequence identity to the amino acid sequence of SEQ ID NO: 11, wherein the light-activated ion channel polypeptide comprises a seven-transmembrane-domain region.

2. The light-activated ion channel polypeptide of claim 1, wherein the amino acid modifications comprise 1, 2, 3, 4, or 5 of I84L, I84V, M91L, R115S, E123A, or K205A amino acid substitutions.

3. The light-activated ion channel polypeptide of claim 1, wherein the light-activated ion channel polypeptide has at least one of a lower level of an ion flux and a lower level of proton flux compared to a control level of the ion flux and proton flux, respectively, when expressed in a cell membrane and contacted with an ion-channel-polypeptide-activating light under suitable conditions for the ion flux and proton flux through the expressed light-activated ion channel polypeptide.

4. The light-activated ion channel polypeptide of claim 3, wherein the control levels of ion flux and proton flux are the levels of ion flux and proton flux, respectively, through a light-activated ion channel polypeptide having an amino acid sequence set forth as SEQ ID NO: 1 expressed in a cell membrane and contacted with the activating light under the suitable conditions for the ion flux and proton flux, respectively.

5. The light-activated ion channel polypeptide of claim 3, wherein the ion flux comprises calcium ion flux.

6. The light-activated ion channel polypeptide of claim 1, wherein the light-activated ion channel polypeptide does not include one or more of the I84L, I84V, M91L, R115S, E123A, and K205A amino acid substitutions in positions corresponding to the sequence set forth as SEQ ID NO: 11.

7. The light-activated ion channel polypeptide of claim 1, wherein the one or more amino acid modifications comprise R115S substitution in the position corresponding to the sequence set forth as SEQ ID NO: 11.

8. The light-activated ion channel polypeptide of claim 1, wherein the polypeptide has the amino acid sequence set forth as SEQ ID NO: 12.

9. A composition comprising a light-activated ion channel polypeptide of claim 1 and a pharmaceutically acceptable carrier, of being activated with light, and the activation alters ion conductivity of the light-activated ion channel polypeptide, with an ion-channel-polypeptide-activating light under conditions suitable for conductivity across the test membrane, and wherein the light-activated ion channel polypeptide has at least one of a lower level of an ion flux and a lower level of proton flux compared to a control level of the ion flux and proton flux, respectively, when expressed in a cell membrane and contacted with an ion-channel-polypeptide-activating light under suitable conditions for the ion flux and proton flux through the expressed light-activated ion channel polypeptide;

(b) contacting the test membrane with a candidate compound;

(c) detecting one or more of the presence and amount of the conductivity across the test membrane contacted with the light and the candidate compound; and (d) comparing the conductivity detected in (c) to the conductivity across a control membrane contacted with the light and not contacted with the candidate compound; wherein a change in one or more of the presence and the amount of the conductivity across the test membrane compared to the control presence and amount of conductivity identifies an effect of the candidate compound on the conductivity across the test membrane.

10. A fusion protein comprising the light-activated ion channel polypeptide of claim 1.

11. The light-activated ion channel polypeptide of claim 1 wherein the light-activated ion channel does not include a substitution of one or more of the amino acids I84, M91, R115, E123, and K205 in positions corresponding to the sequence set forth as SEQ ID NO: 11.

12. The light-activated ion channel polypeptide of claim 1, wherein the light-activated ion channel polypeptide has at least 99% amino acid sequence identity to the corresponding amino acid positions in the sequence set forth as SEQ ID NO: 11.

13. A light-activated ion channel polypeptide comprising an amino acid sequence set forth as (i) SEQ ID NO: 11 or (ii) the amino acid sequence of SEQ ID NO: 11 with one or more amino acid modifications wherein the amino acids corresponding to positions S71, A90, and G114 of SEQ ID NO: 11 are not modified, and having at least 90% amino acid sequence identity to the amino acid sequence of SEQ ID NO: 11, wherein the light-activated ion channel polypeptide comprises a seven-transmembrane-domain region and wherein the light-activated ion channel polypeptide has at least one of a lower level of an ion flux and a lower level of proton flux compared to a control level of the ion flux and proton flux, respectively, when expressed in a cell membrane and contacted with an ion-channel-polypeptide-activating light under suitable conditions for the ion flux and proton flux through the expressed light-activated ion channel polypeptide.

14. The light-activated ion channel polypeptide of claim 13, wherein the amino acid modifications comprise 1, 2, 3, 4, or 5 of I84L, I84V, M91L, R115S, E123A, or K205A amino acid substitutions.

15. The light-activated ion channel polypeptide of claim 13, wherein the control levels of ion flux and proton flux are the levels of ion flux and proton flux, respectively, through a light-activated ion channel polypeptide having an amino acid sequence set forth as SEQ ID NO: 1 expressed in a cell membrane and contacted with the activating light under the suitable conditions for the ion flux and proton flux, respectively.

16. The light-activated ion channel polypeptide of claim 13, wherein the ion flux comprises calcium ion flux.

17. A fusion protein comprising the light-activated ion channel polypeptide of claim 13.

18. The light-activated ion channel polypeptide of claim 13, comprising the amino acid sequence of SEQ ID NO: 11 with one or more amino acid modifications wherein the amino acids corresponding to positions S71, A90, and G114 of SEQ ID NO: 11 are not modified, and having at least 95% amino acid sequence identity to the amino acid sequence of SEQ ID NO: 11.

19. The light-activated ion channel polypeptide of claim 13 wherein the light-activated ion channel does not include a substitution of one or more of the amino acids I84, M91, R115, E123, and K205 in positions corresponding to the sequence set forth as SEQ ID NO: 11.

* * * * *

SEQUENCE LISTING

<160> NUMBER OF SEQ ID NOS: 12

<210> SEQ ID NO 1
<211> LENGTH: 310
<212> TYPE: PRT
<213> ORGANISM: Chlamydomonas reinhardtii

<400> SEQUENCE: 1

| Met | Asp | Tyr | Gly | Gly | Ala | Leu | Ser | Ala | Val | Gly | Arg | Glu | Leu | Leu | Phe |
|---|---|---|---|---|---|---|---|---|---|---|---|---|---|---|---|
| 1 | | | | 5 | | | | | 10 | | | | | 15 | |

| Val | Thr | Asn | Pro | Val | Val | Asn | Gly | Ser | Val | Leu | Val | Pro | Glu | Asp |
|---|---|---|---|---|---|---|---|---|---|---|---|---|---|---|
| | | | 20 | | | | | 25 | | | | | 30 | |

| Gln | Cys | Tyr | Cys | Ala | Gly | Trp | Ile | Glu | Ser | Arg | Gly | Thr | Asn | Gly | Ala |
|---|---|---|---|---|---|---|---|---|---|---|---|---|---|---|---|
| | | | 35 | | | | | 40 | | | | | 45 | | |

| Gln | Thr | Ala | Ser | Asn | Val | Leu | Gln | Trp | Leu | Ala | Ala | Gly | Phe | Ser | Ile |
|---|---|---|---|---|---|---|---|---|---|---|---|---|---|---|---|
| | 50 | | | | | 55 | | | | | 60 | | | | |

| Leu | Leu | Leu | Met | Phe | Tyr | Ala | Tyr | Gln | Thr | Trp | Lys | Ser | Thr | Cys | Gly |
|---|---|---|---|---|---|---|---|---|---|---|---|---|---|---|---|
| 65 | | | | | 70 | | | | | 75 | | | | | 80 |

| Trp | Glu | Glu | Ile | Tyr | Val | Cys | Ala | Ile | Glu | Met | Val | Lys | Val | Ile | Leu |
|---|---|---|---|---|---|---|---|---|---|---|---|---|---|---|---|
| | | | | 85 | | | | | 90 | | | | | 95 | |

| Glu | Phe | Phe | Phe | Glu | Phe | Lys | Asn | Pro | Ser | Met | Leu | Tyr | Leu | Ala | Thr |
|---|---|---|---|---|---|---|---|---|---|---|---|---|---|---|---|
| | | | | 100 | | | | | 105 | | | | | 110 | |

| Gly | His | Arg | Val | Gln | Trp | Leu | Arg | Tyr | Ala | Glu | Trp | Leu | Leu | Thr | Cys |
|---|---|---|---|---|---|---|---|---|---|---|---|---|---|---|---|
| | | | 115 | | | | | 120 | | | | | 125 | | |

| Pro | Val | Ile | Leu | Ile | His | Leu | Ser | Asn | Leu | Thr | Gly | Leu | Ser | Asn | Asp |
|---|---|---|---|---|---|---|---|---|---|---|---|---|---|---|---|
| | 130 | | | | | 135 | | | | | 140 | | | | |

| Tyr | Ser | Arg | Arg | Thr | Met | Gly | Leu | Leu | Val | Ser | Asp | Ile | Gly | Thr | Ile |
|---|---|---|---|---|---|---|---|---|---|---|---|---|---|---|---|
| 145 | | | | | 150 | | | | | 155 | | | | | 160 |

| Val | Trp | Gly | Ala | Thr | Ser | Ala | Met | Ala | Thr | Gly | Tyr | Val | Lys | Val | Ile |
|---|---|---|---|---|---|---|---|---|---|---|---|---|---|---|---|
| | | | | 165 | | | | | 170 | | | | | 175 | |

| Phe | Phe | Cys | Leu | Gly | Leu | Cys | Tyr | Gly | Ala | Asn | Thr | Phe | Phe | His | Ala |
|---|---|---|---|---|---|---|---|---|---|---|---|---|---|---|---|
| | | | 180 | | | | | 185 | | | | | 190 | | |

| Ala | Lys | Ala | Tyr | Ile | Glu | Gly | Tyr | His | Thr | Val | Pro | Lys | Gly | Arg | Cys |
|---|---|---|---|---|---|---|---|---|---|---|---|---|---|---|---|
| | | | 195 | | | | | 200 | | | | | 205 | | |

| Arg | Gln | Val | Val | Thr | Gly | Met | Ala | Trp | Leu | Phe | Phe | Val | Ser | Trp | Gly |
|---|---|---|---|---|---|---|---|---|---|---|---|---|---|---|---|
| | 210 | | | | | 215 | | | | | 220 | | | | |

| Met | Phe | Pro | Ile | Leu | Phe | Ile | Leu | Gly | Pro | Glu | Gly | Phe | Gly | Val | Leu |
|---|---|---|---|---|---|---|---|---|---|---|---|---|---|---|---|
| 225 | | | | | 230 | | | | | 235 | | | | | 240 |

| Ser | Val | Tyr | Gly | Ser | Thr | Val | Gly | His | Thr | Ile | Ile | Asp | Leu | Met | Ser |
|---|---|---|---|---|---|---|---|---|---|---|---|---|---|---|---|
| | | | | 245 | | | | | 250 | | | | | 255 | |

| Lys | Asn | Cys | Trp | Gly | Leu | Leu | Gly | His | Tyr | Leu | Arg | Val | Leu | Ile | His |
|---|---|---|---|---|---|---|---|---|---|---|---|---|---|---|---|
| | | | 260 | | | | | 265 | | | | | 270 | | |

| Glu | His | Ile | Leu | Ile | His | Gly | Asp | Ile | Arg | Lys | Thr | Thr | Lys | Leu | Asn |
|---|---|---|---|---|---|---|---|---|---|---|---|---|---|---|---|
| | 275 | | | | | 280 | | | | | 285 | | | | |

| Ile | Gly | Gly | Thr | Glu | Ile | Glu | Val | Glu | Thr | Leu | Val | Glu | Asp | Glu | Ala |
|---|---|---|---|---|---|---|---|---|---|---|---|---|---|---|---|
| | | | 290 | | | | | 295 | | | | | 300 | | |

| Glu | Ala | Gly | Ala | Val | Pro |
|---|---|---|---|---|---|
| 305 | | | | | 310 |

<210> SEQ ID NO 2
<211> LENGTH: 927
<212> TYPE: DNA
<213> ORGANISM: Artificial sequence
<220> FEATURE:
<223> OTHER INFORMATION: Synthetic polynucleotide

<400> SEQUENCE: 2

-continued

```
atggactatg gcggcgcttt gtctgccgtc ggacgcgaac ttttgttcgt tactaatcct      60
gtggtggtga acgggtccgt cctggtccct gaggatcaat gttactgtgc cggatggatt     120
gaatctcgcg gcacgaacgg cgctcagacc gcgtcaaatg tcctgcagtg cttgcagca     180
ggattcagca ttttgctgct gatgttctat gcctaccaaa cctggaaatc tacatgcggc    240
tgggaggaga tctatgtgtg cgccattgaa atggttaagg tgattctcga gttctttttt    300
gagtttaaga atccctctat gctctacctt gccacaggac accgggtgca gtggctgcgc    360
tatgcagagt ggctgctcac ttgtcctgtc atccttatcc acctgagcaa cctcaccggc    420
ctgagcaacg actacagcag gagaaccatg ggactccttg tctcagacat cgggactatc    480
gtgtgggggg ctaccagcgc catggcaacc ggctatgtta aagtcatctt cttttgtctt    540
ggattgtgct atggcgcgaa cacattttt cacgccgcca agcatatat cgagggttat     600
catactgtgc caaagggtcg gtgccgccag gtcgtgaccg gcatggcatg gctgttttc    660
gtgagctggg gtatgttccc aattctcttc attttggggc cgaaggtttt ggcgtcctg    720
agcgtctatg gctccaccgt aggtcacacg attattgatc tgatgagtaa aaattgttgg    780
gggttgttgg gacactacct gcgcgtcctg atccacgagc acatattgat tcacggagat    840
atccgcaaaa ccaccaaact gaacatcggc ggaacggaga tcgaggtcga gactctcgtc    900
gaagacgaag ccgaggccgg agccgtg                                         927
```

<210> SEQ ID NO 3
<211> LENGTH: 254
<212> TYPE: PRT
<213> ORGANISM: Chlamydomonas reinhardtii

<400> SEQUENCE: 3

```
Gly Trp Ile Glu Ser Arg Gly Thr Asn Gly Ala Gln Thr Ala Ser Asn
1               5                   10                  15

Val Leu Gln Trp Leu Ala Ala Gly Phe Ser Ile Leu Leu Leu Met Phe
            20                  25                  30

Tyr Ala Tyr Gln Thr Trp Lys Ser Thr Cys Gly Trp Glu Glu Ile Tyr
        35                  40                  45

Val Cys Ala Ile Glu Met Val Lys Val Ile Leu Glu Phe Phe Phe Glu
    50                  55                  60

Phe Lys Asn Pro Ser Met Leu Tyr Leu Ala Thr Gly His Arg Val Gln
65                  70                  75                  80

Trp Leu Arg Tyr Ala Glu Trp Leu Leu Thr Cys Pro Val Ile Leu Ile
                85                  90                  95

His Leu Ser Asn Leu Thr Gly Leu Ser Asn Asp Tyr Ser Arg Arg Thr
            100                 105                 110

Met Gly Leu Leu Val Ser Asp Ile Gly Thr Ile Val Trp Gly Ala Thr
        115                 120                 125

Ser Ala Met Ala Thr Gly Tyr Val Lys Val Ile Phe Phe Cys Leu Gly
    130                 135                 140

Leu Cys Tyr Gly Ala Asn Thr Phe Phe His Ala Ala Lys Ala Tyr Ile
145                 150                 155                 160

Glu Gly Tyr His Thr Val Pro Lys Gly Arg Cys Arg Gln Val Val Thr
                165                 170                 175

Gly Met Ala Trp Leu Phe Phe Val Ser Trp Gly Met Phe Pro Ile Leu
            180                 185                 190

Phe Ile Leu Gly Pro Glu Gly Phe Gly Val Leu Ser Val Tyr Gly Ser
        195                 200                 205
```

Thr Val Gly His Thr Ile Ile Asp Leu Met Ser Lys Asn Cys Trp Gly
            210                 215                 220

Leu Leu Gly His Tyr Leu Arg Val Leu Ile His Glu His Ile Leu Ile
225                 230                 235                 240

His Gly Asp Ile Arg Lys Thr Thr Lys Leu Asn Ile Gly Gly
            245                 250

<210> SEQ ID NO 4
<211> LENGTH: 266
<212> TYPE: PRT
<213> ORGANISM: Chlamydomonas reinhardtii

<400> SEQUENCE: 4

Ser Arg Gly Thr Asn Gly Ala Gln Thr Ala Ser Asn Val Leu Gln Trp
1               5                   10                  15

Leu Ala Ala Gly Phe Ser Ile Leu Leu Met Phe Tyr Ala Tyr Gln
            20                  25                  30

Thr Trp Lys Ser Thr Cys Gly Trp Glu Ile Tyr Val Cys Ala Ile
            35                  40                  45

Glu Met Val Lys Val Ile Leu Glu Phe Phe Phe Glu Phe Lys Asn Pro
50                  55                  60

Ser Met Leu Tyr Leu Ala Thr Gly His Arg Val Gln Trp Leu Arg Tyr
65                  70                  75                  80

Ala Glu Trp Leu Leu Thr Cys Pro Val Ile Leu Ile His Leu Ser Asn
                85                  90                  95

Leu Thr Gly Leu Ser Asn Asp Tyr Ser Arg Arg Thr Met Gly Leu Leu
            100                 105                 110

Val Ser Asp Ile Gly Thr Ile Val Trp Gly Ala Thr Ser Ala Met Ala
            115                 120                 125

Thr Gly Tyr Val Lys Val Ile Phe Phe Cys Leu Gly Leu Cys Tyr Gly
130                 135                 140

Ala Asn Thr Phe Phe His Ala Ala Lys Ala Tyr Ile Glu Gly Tyr His
145                 150                 155                 160

Thr Val Pro Lys Gly Arg Cys Arg Gln Val Val Thr Gly Met Ala Trp
                165                 170                 175

Leu Phe Phe Val Ser Trp Gly Met Phe Pro Ile Leu Phe Ile Leu Gly
            180                 185                 190

Pro Glu Gly Phe Gly Val Leu Ser Val Tyr Gly Ser Thr Val Gly His
            195                 200                 205

Thr Ile Ile Asp Leu Met Ser Lys Asn Cys Trp Gly Leu Leu Gly His
            210                 215                 220

Tyr Leu Arg Val Leu Ile His Glu His Ile Leu Ile His Gly Asp Ile
225                 230                 235                 240

Arg Lys Thr Thr Lys Leu Asn Ile Gly Gly Thr Glu Ile Glu Val Glu
                245                 250                 255

Thr Leu Val Glu Asp Glu Ala Glu Ala Gly
            260                 265

<210> SEQ ID NO 5
<211> LENGTH: 350
<212> TYPE: PRT
<213> ORGANISM: Chlamydomonas noctigama

<400> SEQUENCE: 5

Met Ala Glu Leu Ile Ser Ser Ala Thr Arg Ser Leu Phe Ala Ala Gly
1               5                   10                  15

Gly Ile Asn Pro Trp Pro Asn Pro Tyr His His Glu Asp Met Gly Cys
            20                  25                  30

Gly Gly Met Thr Pro Thr Gly Glu Cys Phe Ser Thr Glu Trp Trp Cys
        35                  40                  45

Asp Pro Ser Tyr Gly Leu Ser Asp Ala Gly Tyr Gly Tyr Cys Phe Val
 50                  55                  60

Glu Ala Thr Gly Gly Tyr Leu Val Val Gly Val Glu Lys Lys Gln Ala
 65                  70                  75                  80

Trp Leu His Ser Arg Gly Thr Pro Gly Glu Lys Ile Gly Ala Gln Val
                 85                  90                  95

Cys Gln Trp Ile Ala Phe Ser Ile Ala Ile Ala Leu Leu Thr Phe Tyr
            100                 105                 110

Gly Phe Ser Ala Trp Lys Ala Thr Cys Gly Trp Glu Glu Val Tyr Val
        115                 120                 125

Cys Cys Val Glu Val Leu Phe Val Thr Leu Glu Ile Phe Lys Glu Phe
130                 135                 140

Ser Ser Pro Ala Thr Val Tyr Leu Ser Thr Gly Asn His Ala Tyr Cys
145                 150                 155                 160

Leu Arg Tyr Phe Glu Trp Leu Leu Ser Cys Pro Val Ile Leu Ile Lys
                165                 170                 175

Leu Ser Asn Leu Ser Gly Leu Lys Asn Asp Tyr Ser Lys Arg Thr Met
            180                 185                 190

Gly Leu Ile Val Ser Cys Val Gly Met Ile Val Phe Gly Met Ala Ala
        195                 200                 205

Gly Leu Ala Thr Asp Trp Leu Lys Trp Leu Leu Tyr Ile Val Ser Cys
    210                 215                 220

Ile Tyr Gly Gly Tyr Met Tyr Phe Gln Ala Ala Lys Cys Tyr Val Glu
225                 230                 235                 240

Ala Asn His Ser Val Pro Lys Gly His Cys Arg Met Val Val Lys Leu
                245                 250                 255

Met Ala Tyr Ala Tyr Phe Ala Ser Trp Gly Ser Tyr Pro Ile Leu Trp
            260                 265                 270

Ala Val Gly Pro Glu Gly Leu Leu Lys Leu Ser Pro Tyr Ala Asn Ser
        275                 280                 285

Ile Gly His Ser Ile Cys Asp Ile Ile Ala Lys Glu Phe Trp Thr Phe
    290                 295                 300

Leu Ala His His Leu Arg Ile Lys Ile His Glu His Ile Leu Ile His
305                 310                 315                 320

Gly Asp Ile Arg Lys Thr Thr Lys Met Glu Ile Gly Gly Glu Glu Val
                325                 330                 335

Glu Val Glu Glu Phe Val Glu Glu Asp Glu Asp Thr Val
            340                 345                 350

<210> SEQ ID NO 6
<211> LENGTH: 1050
<212> TYPE: DNA
<213> ORGANISM: Artificial sequence
<220> FEATURE:
<223> OTHER INFORMATION: Synthetic polynucleotide

<400> SEQUENCE: 6
atggctgagc tgatcagcag cgccaccaga tctctgtttg ccgccggagg catcaaccct    60
tggcctaacc cctaccacca cgaggacatg ggctgtggag gaatgacacc tacaggcgag   120
tgcttcagca ccgagtggtg gtgtgaccct tcttacggac tgagcgacgc cggatacgga   180

```
tattgcttcg tggaggccac aggcggctac ctggtcgtgg gagtggagaa gaagcaggct      240
tggctgcaca gcagaggcac accaggagaa aagatcggcg cccaggtctg ccagtggatt      300
gctttcagca tcgccatcgc cctgctgaca ttctacggct tcagcgcctg gaaggccact      360
tgcggttggg aggaggtcta cgtctgttgc gtcgaggtgc tgttcgtgac cctggagatc      420
ttcaaggagt tcagcagccc cgccacagtg tacctgtcta ccggcaacca cgcctattgc      480
ctgcgctact tcgagtggct gctgtcttgc cccgtgatcc tgatcaagct gagcaacctg      540
agcggcctga agaacgacta cagcaagcgg accatgggcc tgatcgtgtc ttgcgtggga      600
atgatcgtgt tcggcatggc cgcaggactg gctaccgatt ggctcaagtg gctgctgtat      660
atcgtgtctt gcatctacgg cggctacatg tacttccagg ccgccaagtg ctacgtggaa      720
gccaaccaca gcgtgcctaa aggccattgc cgcatggtcg tgaagctgat ggcctacgct      780
tacttcgcct cttggggcag ctacccaatc ctctgggcag tgggaccaga aggactgctg      840
aagctgagcc cttacgccaa cagcatcggc cacagcatct cgacatcat  cgccaaggag      900 ttttggacct tcctggccca ccacctgagg atcaagatcc acgagcacat cctgatccac      960
ggcgacatcc ggaagaccac caagatggag atcggaggcg aggaggtgga agtggaagag      1020
ttcgtggagg aggaggacga ggacacagtg                                       1050
```

<210> SEQ ID NO 7
<211> LENGTH: 254
<212> TYPE: PRT
<213> ORGANISM: Artificial Sequence
<220> FEATURE:
<223> OTHER INFORMATION: Synthetic polypeptide
<400> SEQUENCE: 7

```
Ala Trp Leu His Ser Arg Gly Thr Pro Gly Glu Lys Ile Gly Ala Gln
1               5                   10                  15

Val Cys Gln Trp Ile Ala Phe Ser Ile Ala Ile Ala Leu Leu Thr Phe
            20                  25                  30

Tyr Gly Phe Ser Ala Trp Lys Ala Thr Cys Gly Trp Glu Glu Val Tyr
        35                  40                  45

Val Cys Cys Val Glu Val Leu Phe Val Thr Leu Glu Ile Phe Lys Glu
    50                  55                  60

Phe Ser Ser Pro Ala Thr Val Tyr Leu Ser Thr Gly Asn His Ala Tyr
65                  70                  75                  80

Cys Leu Arg Tyr Phe Glu Trp Leu Leu Ser Cys Pro Val Ile Leu Ile
                85                  90                  95

Lys Leu Ser Asn Leu Ser Gly Leu Lys Asn Asp Tyr Ser Lys Arg Thr
            100                 105                 110

Met Gly Leu Ile Val Ser Cys Val Gly Met Ile Val Phe Gly Met Ala
        115                 120                 125

Ala Gly Leu Ala Thr Asp Trp Leu Lys Trp Leu Leu Tyr Ile Val Ser
    130                 135                 140

Cys Ile Tyr Gly Gly Tyr Met Tyr Phe Gln Ala Ala Lys Cys Tyr Val
145                 150                 155                 160

Glu Ala Asn His Ser Val Pro Lys Gly His Cys Arg Met Val Val Lys
                165                 170                 175

Leu Met Ala Tyr Ala Tyr Phe Ala Ser Trp Gly Ser Tyr Pro Ile Leu
            180                 185                 190

Trp Ala Val Gly Pro Glu Gly Leu Leu Lys Leu Ser Pro Tyr Ala Asn
        195                 200                 205
```

```
Ser Ile Gly His Ser Ile Cys Asp Ile Ile Ala Lys Glu Phe Trp Thr
    210                 215                 220

Phe Leu Ala His His Leu Arg Ile Lys Ile His Glu His Ile Leu Ile
225                 230                 235                 240

His Gly Asp Ile Arg Lys Thr Thr Lys Met Glu Ile Gly Gly
                245                 250

<210> SEQ ID NO 8
<211> LENGTH: 325
<212> TYPE: PRT
<213> ORGANISM: Stigeoclonuim helveticum

<400> SEQUENCE: 8

Met Glu Thr Ala Ala Thr Met Thr His Ala Phe Ile Ser Ala Val Pro
1               5                   10                  15

Ser Ala Glu Ala Thr Ile Arg Gly Leu Leu Ser Ala Ala Ala Val Val
                20                  25                  30

Thr Pro Ala Ala Asp Ala His Gly Glu Thr Ser Asn Ala Thr Thr Ala
            35                  40                  45

Gly Ala Asp His Gly Cys Phe Pro His Ile Asn His Gly Thr Glu Leu
    50                  55                  60

Gln His Lys Ile Ala Val Gly Leu Gln Trp Phe Thr Val Ile Val Ala
65                  70                  75                  80

Ile Val Gln Leu Ile Phe Tyr Gly Trp His Ser Phe Lys Ala Thr Thr
                85                  90                  95

Gly Trp Glu Glu Val Tyr Val Cys Val Ile Glu Leu Val Lys Cys Phe
            100                 105                 110

Ile Glu Leu Phe His Glu Val Asp Ser Pro Ala Thr Val Tyr Gln Thr
        115                 120                 125

Asn Gly Gly Ala Val Ile Trp Leu Arg Tyr Ser Met Trp Leu Leu Thr
130                 135                 140

Cys Pro Val Ile Leu Ile His Leu Ser Asn Leu Thr Gly Leu His Glu
145                 150                 155                 160

Glu Tyr Ser Lys Arg Thr Met Thr Ile Leu Val Thr Asp Ile Gly Asn
                165                 170                 175

Ile Val Trp Gly Ile Thr Ala Ala Phe Thr Lys Gly Pro Leu Lys Ile
            180                 185                 190

Leu Phe Phe Met Ile Gly Leu Phe Tyr Gly Val Thr Cys Phe Phe Gln
        195                 200                 205

Ile Ala Lys Val Tyr Ile Glu Ser Tyr His Thr Leu Pro Lys Gly Val
    210                 215                 220

Cys Arg Lys Ile Cys Lys Ile Met Ala Tyr Val Phe Phe Cys Ser Trp
225                 230                 235                 240

Leu Met Phe Pro Val Met Phe Ile Ala Gly His Glu Gly Leu Gly Leu
                245                 250                 255

Ile Thr Pro Tyr Thr Ser Gly Ile Gly His Leu Ile Leu Asp Leu Ile
            260                 265                 270

Ser Lys Asn Thr Trp Gly Phe Leu Gly His His Leu Arg Val Lys Ile
        275                 280                 285

His Glu His Ile Leu Ile His Gly Asp Ile Arg Lys Thr Thr Thr Ile
    290                 295                 300

Asn Val Ala Gly Glu Asn Met Glu Ile Glu Thr Phe Val Asp Glu Glu
305                 310                 315                 320

Glu Glu Gly Gly Val
```

<210> SEQ ID NO 9
<211> LENGTH: 975
<212> TYPE: DNA
<213> ORGANISM: Artificial sequence
<220> FEATURE:
<223> OTHER INFORMATION: Synthetic polynucleotide

<400> SEQUENCE: 9

```
atggaaacag ccgccacaat gacccacgcc tttatctcag ccgtgcctag cgccgaagcc      60
acaattagag gcctgctgag cgccgcagca gtggtgacac cagcagcaga cgctcacgga     120
gaaacctcta acgccacaac agccggagcc gatcacggtt gcttccccca catcaaccac     180
ggaaccgagc tgcagcacaa gatcgcagtg ggactccagt ggttcaccgt gatcgtggct     240
atcgtgcagc tcatcttcta cggttggcac agcttcaagg ccacaaccgg ctgggaggag     300
gtctacgtct gcgtgatcga gctcgtcaag tgcttcatcg agctgttcca cgaggtcgac     360
agcccagcca cagtgtacca gaccaacgga ggagccgtga tttggctgcg gtacagcatg     420
tggctcctga cttgccccgt gatcctgatc cacctgagca acctgaccgg actgcacgaa     480
gagtacagca agcggaccat gaccatcctg gtgaccgaca tcggcaacat cgtgtggggg     540
atcacagccg cctttacaaa gggccccctg aagatcctgt tcttcatgat cggcctgttc     600
tacggcgtga cttgcttctt ccagatcgcc aaggtgtata tcgagagcta ccacaccctg     660
cccaaaggcg tctgccggaa gatttgcaag atcatggcct acgtcttctt ctgctcttgg     720
ctgatgttcc ccgtgatgtt catcgccgga cacgagggac tgggcctgat cacaccttac     780
accagcggaa tcggccacct gatcctggat ctgatcagca agaacacttg gggcttcctg     840
ggccaccacc tgagagtgaa gatccacgag cacatcctga tccacggcga catccggaag     900
acaaccacca tcaacgtggc cggcgagaac atggagatcg agaccttcgt cgacgaggag     960
gaggagggag gagtg                                                      975
```

<210> SEQ ID NO 10
<211> LENGTH: 266
<212> TYPE: PRT
<213> ORGANISM: Stigeoclonium helveticum

<400> SEQUENCE: 10

```
Asn His Gly Thr Glu Leu Gln His Lys Ile Ala Val Gly Leu Gln Trp
1               5                   10                  15

Phe Thr Val Ile Val Ala Ile Val Gln Leu Ile Phe Tyr Gly Trp His
            20                  25                  30

Ser Phe Lys Ala Thr Thr Gly Trp Glu Glu Val Tyr Val Cys Val Ile
        35                  40                  45

Glu Leu Val Lys Cys Phe Ile Glu Leu Phe His Glu Val Asp Ser Pro
    50                  55                  60

Ala Thr Val Tyr Gln Thr Asn Gly Gly Ala Val Ile Trp Leu Arg Tyr
65                  70                  75                  80

Ser Met Trp Leu Leu Thr Cys Pro Val Ile Leu Ile His Leu Ser Asn
                85                  90                  95

Leu Thr Gly Leu His Glu Glu Tyr Ser Lys Arg Thr Met Thr Ile Leu
            100                 105                 110

Val Thr Asp Ile Gly Asn Ile Val Trp Gly Ile Thr Ala Ala Phe Thr
        115                 120                 125

Lys Gly Pro Leu Lys Ile Leu Phe Phe Met Ile Gly Leu Phe Tyr Gly
```

```
            130                 135                 140
Val Thr Cys Phe Phe Gln Ile Ala Lys Val Tyr Ile Glu Ser Tyr His
145                 150                 155                 160

Thr Leu Pro Lys Gly Val Cys Arg Lys Ile Cys Lys Ile Met Ala Tyr
                165                 170                 175

Val Phe Phe Cys Ser Trp Leu Met Phe Pro Val Met Phe Ile Ala Gly
                180                 185                 190

His Glu Gly Leu Gly Leu Ile Thr Pro Tyr Thr Ser Gly Ile Gly His
                195                 200                 205

Leu Ile Leu Asp Leu Ile Ser Lys Asn Thr Trp Gly Phe Leu Gly His
                210                 215                 220

His Leu Arg Val Lys Ile His Glu His Ile Leu Ile His Gly Asp Ile
225                 230                 235                 240

Arg Lys Thr Thr Thr Ile Asn Val Ala Gly Glu Asn Met Glu Ile Glu
                245                 250                 255

Thr Phe Val Asp Glu Glu Glu Gly Gly
                260                 265
```

<210> SEQ ID NO 11
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 11

```
Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
                35                  40                  45

Gln Thr Ala Ser Asn Val Leu Gln Trp Leu Ala Ala Gly Phe Ser Ile
            50                  55                  60

Leu Leu Leu Met Phe Tyr Ser Tyr Gln Thr Trp Lys Ser Thr Cys Gly
65                  70                  75                  80

Trp Glu Glu Ile Tyr Val Cys Ala Ile Ala Met Val Lys Val Ile Leu
                85                  90                  95

Glu Phe Phe Phe Glu Phe Lys Asn Pro Ser Met Leu Tyr Leu Ala Thr
                100                 105                 110

Gly Gly Arg Val Gln Trp Leu Arg Tyr Ala Glu Trp Leu Leu Thr Cys
                115                 120                 125

Pro Val Ile Leu Ile His Leu Ser Asn Leu Thr Gly Leu Ser Asn Asp
                130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
                180                 185                 190

Ala Lys Ala Tyr Ile Glu Gly Tyr His Thr Val Pro Lys Gly Arg Cys
                195                 200                 205

Arg Gln Val Val Thr Gly Met Ala Trp Leu Phe Phe Val Ser Trp Gly
                210                 215                 220

Met Phe Pro Ile Leu Phe Ile Leu Gly Pro Glu Gly Phe Gly Val Leu
```

```
                225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
                275                 280                 285

Ile Gly Gly Thr Glu Ile Glu Val Glu Thr Leu Val Glu Asp Glu Ala
        290                 295                 300

Glu Ala Gly Ala Val Pro
305                 310

<210> SEQ ID NO 12
<211> LENGTH: 310
<212> TYPE: PRT
<213> ORGANISM: Artificial sequence
<220> FEATURE:
<223> OTHER INFORMATION: Synthetic polypeptide

<400> SEQUENCE: 12

Met Asp Tyr Gly Gly Ala Leu Ser Ala Val Gly Arg Glu Leu Leu Phe
1               5                   10                  15

Val Thr Asn Pro Val Val Asn Gly Ser Val Leu Val Pro Glu Asp
                20                  25                  30

Gln Cys Tyr Cys Ala Gly Trp Ile Glu Ser Arg Gly Thr Asn Gly Ala
            35                  40                  45

Gln Thr Ala Ser Asn Val Leu Gln Trp Leu Ala Ala Gly Phe Ser Ile
        50                  55                  60

Leu Leu Leu Met Phe Tyr Ser Tyr Gln Thr Trp Lys Ser Thr Cys Gly
65                  70                  75                  80

Trp Glu Glu Ile Tyr Val Cys Ala Ile Ala Met Val Lys Val Ile Leu
                85                  90                  95

Glu Phe Phe Phe Glu Phe Lys Asn Pro Ser Met Leu Tyr Leu Ala Thr
            100                 105                 110

Gly Gly Ser Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
                260                 265                 270

Glu His Ile Leu Ile His Gly Asp Ile Arg Lys Thr Thr Lys Leu Asn
```

```
                    275                 280                 285
Ile Gly Gly Thr Glu Ile Glu Val Glu Thr Leu Val Glu Asp Glu Ala
        290                 295                 300

Glu Ala Gly Ala Val Pro
305                 310
```